United States Patent
Bhyri et al.

(10) Patent No.: US 12,416,010 B2
(45) Date of Patent: Sep. 16, 2025

(54) PLANT TERMINATOR SEQUENCES

(71) Applicant: CORTEVA AGRISCIENCE LLC, Indianapolis, IN (US)

(72) Inventors: Priyanka Bhyri, Johnston, IA (US); Nandini Krishnamurthy, Grimes, IA (US); Eswar Narayanan, Grimes, IA (US); Ajit Nott, Johnston, IA (US); Rinku Ranjan Sarangi, Andhra Pradesh (IN)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 279 days.

(21) Appl. No.: 17/646,887

(22) Filed: Jan. 4, 2022

(65) Prior Publication Data

US 2022/0119831 A1    Apr. 21, 2022

Related U.S. Application Data

(62) Division of application No. 16/032,228, filed on Jul. 11, 2018, now Pat. No. 11,248,233, which is a division of application No. 14/129,551, filed as application No. PCT/US2012/046686 on Jul. 13, 2012, now Pat. No. 10,059,953.

(60) Provisional application No. 61/557,433, filed on Nov. 9, 2011.

(30) Foreign Application Priority Data

Jul. 15, 2011 (IN) ............ 2001/DEL/2011

(51) Int. Cl.
C12N 15/82    (2006.01)

(52) U.S. Cl.
CPC ..... *C12N 15/8216* (2013.01); *C12N 15/8222* (2013.01)

(58) Field of Classification Search
None
See application file for complete search history.

(56) References Cited

U.S. PATENT DOCUMENTS

| | | | |
|---|---|---|---|
| 10,059,953 B2 | 8/2018 | Bhyri et al. | |
| 11,248,233 B2 | 2/2022 | Bhyri et al. | |
| 2003/0049814 A1* | 3/2003 | Andrews | C12N 9/1092 800/278 |
| 2006/0123505 A1 | 6/2006 | Kikuchi et al. | |
| 2007/0214517 A1 | 9/2007 | Alexandrov | |
| 2008/0263722 A1 | 10/2008 | Hu | |
| 2009/0093620 A1 | 4/2009 | Kovalic | |
| 2009/0320160 A1 | 12/2009 | Li | |
| 2010/0255584 A1 | 10/2010 | Yongwei | |

FOREIGN PATENT DOCUMENTS

| | | |
|---|---|---|
| WO | 20000020613 A1 | 4/2000 |
| WO | 2006013072 A2 | 9/2006 |
| WO | WO-2010077816 A1 | 7/2010 |
| WO | WO-2010124953 A1 | 11/2010 |

OTHER PUBLICATIONS

Mignone and Pesole, 2011, mRNA Untranslated Regions (UTRs), In: eLS, John Wiley & Sons, pp. 1-5. (Year: 2011).*
Bieri, et al "Geminivirus sequences as bidirectional transcription termination/polyadenylation signals for economic construction of stably expressed transgenes" Molecular Breeding, 2002, vol. 10: 107-117.
Gilmartin, G., "Eukaryotic mRNA 3' processing: a common means to different ends" Genes and Development, 2005, vol. 19: 2517-2521.
Ingelbrecht, I. et al., "Different 3' End Regions Strongly Influence the Level of Gene Expression in Plant Cells" The Plant Cell, 1989, vol. 1: 671-680.
Kobayashi et al "Evidence for an evolutionary force that prevents epigenetic silencing between tail-to-tail rice genes with a short spacer" Gene, 2005, vol. 346:231-240.
Lin, Chi-Hui, et al "A conserved inverted repeat from rice plastome functions as an intrinsic transcription terminator" Chinese Science Bulletin, 2005, vol. 50:15, 1669-1672.
Mette, M.F. et al, "Production of aberrant promoter transcripts contributes to methylation and silencing of unlinked homologous promoters in trans" The EMBO Journal, 1999, vol. 18:1, 241-248.
Mette, M.F. et al, "Transcriptional silencing and promoter methylation triggered by double-stranded RNA" The EMBO Journal, 2000, vol. 19:19, 5194-5201.
Mourrain, P. et al, "A single transgene locus triggers both transcriptional and post-transcriptional silencing through double-stranded RNA production" Planta, 2007, vol. 225:365-379.
Peremarti, A. et al, "Promoter diversity in multigene transformation" Plant Molecular Biology, 2010, vol. 73:363-378.
Proudfoot, N. "New perspectives on connecting messenger RNA 3' end formation to transcription" Current Opinion in Cell Biology, 2004, vol. 16:272-278.
Genbank Accession No. AC135594 2003.
Genbank EBI Accession No. CW845633 2004.
International Search Report and Written Opinion, International Application No. PCT/US2012/046686 mailed Feb. 1, 2013.
Hartl DL, Nurminsky DI, Jones RW, and Lozovskaya ER. (1995). 'Structure and Evolution in *Drosophila*: Applications of the Framework P1 Map.' Tempo and Mode in Evolution: Genetics and Paleontology 50 Years After Simpson. Washington, DC: The National Academies Press. p. 299-312.
Liu, Y., Mitsukawa N., Vazquez-Tello A., Whittier RF. (1995). "Generation of a high-quality P1 library of *Arabidopsis* suitable for chromosome walking." The Plant Journal. 7()2):351-358.
Sternberg N., 1990, Bacteriophage P1 cloning system for the isolation, amplification, and recovery of DNA fragments as large as 100 kilobase pairs, Proc. Natl. Acad. Sci. USA 87: 103-107.

(Continued)

*Primary Examiner* — Cynthia E Collins

(57) ABSTRACT

This invention relates to gene expression regulatory sequences, specifically transcription terminator sequences. Plant transcription terminator sequences are described herein. Methods for identifying novel plant transcription terminator sequences that can terminate transcription in one orientation or in a bidirectional manner and methods of using these terminator sequences to generate transgenic plants are described herein.

7 Claims, 3 Drawing Sheets

Specification includes a Sequence Listing.

(56) References Cited

OTHER PUBLICATIONS

*Arabidopsis thaliana* genomic DNA, chromosome 3, P1 clone: MDC8, Gen Bank accession No. AP000373, published Feb. 14, 2004.
Kaneko et al., 2000, Structural analysis of *Arabidopsis thaliana* chromosome 3. II. Sequence features of the 4,251,695 op regions covered by 90 P1, TAC and BAC clones, DNA Research 7: 217-221.
*Arabidopsis thaliana* mRNA for a mannose-binding lectin superfamily protein (JR1), GenBank accession No. NM_001202984, version NM_001202984.2, published Feb. 14, 2019.
Maize Streak Virus (MSV) DNA sequence, GenBank accession No. X01633, published Apr. 18, 2005.
Mignone and Pesole, 2011, mRNA Untranslated Regions (UTRs), In: eLS, John Wiley & Sons, pp. 1-5.
Bevan M., et al., "*Arabidopsis thaliana* DNA Chromosome 4, BAC clone F27G19ESSA project," GenbBank.
International Preliminary Report on Patentability for International Application No. PCT/US2012/046686, mailed Jan. 30, 2014, 09 Pages.
Nagaya S., et al., "The HSP Terminator of *Arabidopsis thaliana* Increases Gene Expression in Plant Cells." Plant and Cell Physiology.
Olsen A.N., et al., "NAC Transcription Factors: Structurally Distinct, Functionally Diverse," Trends in Plant Science, Feb. 2005, vol. 10, No. 2, Feb. 2005, pp. 79-87.

\* cited by examiner

SEQUENCE LISTING

```
<160> NUMBER OF SEQ ID NOS: 162

<210> SEQ ID NO 1
<211> LENGTH: 16437
<212> TYPE: DNA
<213> ORGANISM: Artificial sequence
<220> FEATURE:
<223> OTHER INFORMATION: Vector sequence
```

<400> SEQUENCE: 1

```
gtttacccgc caatatatcc tgtcaaacac tgatagttta aactgaaggc gggaaacgac      60
aatctgatca tgagcggaga attaagggag tcacgttatg accccgccg atgacgcggg     120
acaagccgtt ttacgtttgg aactgacaga accgcaacgt tgaaggagcc actcagcaag     180
ctggtacgat tgtaatacga ctcactatag ggcgaattga gcgctgttta acgctcttc     240
aactggaaga gcggttacca gagctggtca cctttgtcca ccaagatgga actgcggcct     300
cgaagctggc gcgccgtgca gcgtgacccg tcgtgcccc tctctagaga taatgagcat     360
tgcatgtcta agttataaaa aattaccaca tattttttt gtcacacttg tttgaagtgc     420
agtttatcta tctttataca tatatttaaa ctttactcta cgaataatat aatctatagt     480
actacaataa tatcagtgtt ttagagaatc atataaatga acagttagac atggtctaaa     540
ggacaattga gtattttgac aacaggactc tacagtttta tcttttagt gtgcatgtgt     600
tctccttttt ttttgcaaat agcttcacct atataatact tcatccattt tattagtaca     660
tccatttagg gtttagggtt aatggttttt atagactaat ttttttagta catctatttt     720
attctatttt agcctctaaa ttaagaaaac taaaactcta ttttagtttt tttatttaat     780
aatttagata taaaatagaa taaaataaag tgactaaaaa ttaaacaaat ccctttaag     840
aaattaaaaa aactaaggaa acattttct tgtttcgagt agataatgcc agcctgttaa     900
acgccgtcga cgagtctaac ggacaccaac cagcgaacca gcagcgtcgc gtcgggccaa     960
gcgaagcaga cggcacggca tctctgtcgc tgcctctgga ccctctcga gagttccgct    1020
ccaccgttgg acttgctccg ctgtcggcat ccagaaattg cgtggcggag cggcagacgt    1080
gagccggcac ggcaggcggc ctcctcctcc tctcacggca ccggcagcta cggggattc    1140
ctttcccacc gctccttcgc tttcccttcc tcgcccgccg taataaatag acaccccctc    1200
cacccctct ttccccaacc tcgtgttgtt cggagcgcac acacacacaa ccagatctcc    1260
cccaaatcca cccgtcggca cctccgcttc aaggtacgcc gctcgtcctc ccccccccc    1320
ctctctacct tctctagatc ggcgttccgg tccatgcatg gttagggccc ggtagttcta    1380
cttctgttca tgtttgtgtt agatccgtgt ttgtgttaga tccgtgctgc tagcgttcgt    1440
acacggatgc gacctgtacg tcagacacgt tctgattgct aacttgccag tgtttctctt    1500
tggggaatcc tgggatggct ctagccgttc cgcagacggg atcgatttca tgattttttt    1560
tgtttcgttg catagggttt ggtttgccct tttcctttat ttcaatatat gccgtgcact    1620
tgtttgtcgg gtcatctttt catgcttttt tttgtcttgg ttgtgatgat gtggtctggt    1680
tgggcggtcg ttctagatcg gagtagaatt ctgtttcaaa ctacctggtg gatttattaa    1740
ttttggatct gtatgtgtgt gccatacata ttcatagtta cgaattgaag atgatggatg    1800
gaaatatcga tctaggatag gtatacatgt tgatgcgggt tttactgatg catatacaga    1860
gatgcttttt gttcgcttgg ttgtgatgat gtggtgtggt tgggcggtcg ttcattcgtt    1920
ctagatcgga gtagaatact gtttcaaact acctggtgta tttattaatt ttggaactgt    1980
atgtgtgtgt catacatctt catagttacg agtttaagat ggatggaaat atcgatctag    2040
gataggtata catgttgatg tgggttttac tgatgcatat acatgatggc atatgcagca    2100
tctattcata tgctctaacc ttgagtacct atctattata ataaacaagt atgttttata    2160
attatttga tcttgatata cttggatgat ggcatatgca gcagctatat gtggattttt    2220
ttagccctgc cttcatacgc tatttatttg cttggtactg tttcttttgt cgatgctcac    2280
```

```
cctgttgttt ggtgttactt ctgcaggtcg actttaactt agcctaggat ccacacgaca      2340
ccatggtccg tcctgtagaa accccaaccc gtgaaatcaa aaaactcgac ggcctgtggg      2400
cattcagtct ggatcgcgaa aactgtggaa ttgatcagcg ttggtgggaa agcgcgttac      2460
aagaaagccg ggcaattgct gtgccaggca gttttaacga tcagttcgcc gatgcagata      2520
ttcgtaatta tgcgggcaac gtctggtatc agcgcgaagt ctttataccg aaaggttggg      2580
caggccagcg tatcgtgctg cgtttcgatg cggtcactca ttacggcaaa gtgtgggtca      2640
ataatcagga agtgatggag catcagggcg gctatacgcc atttgaagcc gatgtcacgc      2700
cgtatgttat tgcccgggaaa agtgtacgta agtttctgct tctacctttg atatatatat      2760
aataattatc attaattagt agtaatataa tatttcaaat attttttttca aaataaaaga      2820 atgtagtata tagcaattgc ttttctgtag tttataagtg tgtatatttt aatttataac      2880
ttttctaata tatgaccaaa atttgttgat gtgcaggtat caccgtttgt gtgaacaacg      2940
aactgaactg gcagactatc ccgccgggaa tggtgattac cgacgaaaac ggcaagaaaa      3000
agcagtctta cttccatgat ttctttaact atgccggaat ccatcgcagc gtaatgctct      3060
acaccacgcc gaacacctgg gtggacgata tcaccgtggt gacgcatgtc gcgcaagact      3120
gtaaccacgc gtctgttgac tggcaggtgg tggccaatgg tgatgtcagc gttgaactgc      3180
gtgatgcgga tcaacaggtg gttgcaactg gacaaggcac tagcgggact ttgcaagtgg      3240
tgaatccgca cctctggcaa ccgggtgaag gttatctcta tgaactgtgc gtcacagcca      3300
aaagccagac agagtgtgat atctacccgc ttcgcgtcgg catccggtca gtggcagtga      3360
agggcgaaca gttcctgatt aaccacaaac cgttctactt tactggcttt ggtcgtcatg      3420
aagatgcgga cttgcgtggc aaaggattcg ataacgtgct gatggtgcac gaccacgcat      3480
taatggactg gattggggcc aactcctacc gtacctcgca ttacccttac gctgaagaga      3540
tgctcgactg ggcagatgaa catggcatcg tggtgattga tgaaactgct gctgtcggct      3600
ttaacctctc tttaggcatt ggtttcgaag cgggcaacaa gccgaaagaa ctgtacagcg      3660
aagaggcagt caacggggaa actcagcaag cgcacttaca ggcgattaaa gagctgatag      3720
cgcgtgacaa aaaccaccca agcgtggtga tgtggagtat tgccaacgaa ccggatcccc      3780
gtccgcaagg tgcacgggaa tatttcgcgc cactggcgga agcaacgcgt aaactcgacc      3840
cgacgcgtcc gatcacctgc gtcaatgtaa tgttctgcga cgctcacacc gataccatca      3900
gcgatctctt tgatgtgctg tgcctgaacc gttattacgg atggtatgtc caaagcggcg      3960
atttggaaac ggcagagaag gtactggaaa aagaacttct ggcctggcag agaaactgc      4020 atcagccgat tatcatcacc gaatacggcg tggatacgtt agccgggctg cactcaatgt      4080
acaccgacat gtggagtgaa gagtatcagt gtgcatggct ggatatgtat caccgcgtct      4140
ttgatcgcgt cagcgccgtc gtcggtgaac aggtatggaa tttcgccgat tttgcgacct      4200
cgcaaggcat attgcgcgtt ggcggtaaca agaaagggat cttcactcgc gaccgcaaac      4260
cgaagtcggc ggcttttctg ctgcaaaaac gctggactgg catgaacttc ggtgaaaaac      4320
cgcagcaggg aggcaaacaa ggtaccgatc catggcctcc tccgaggacg tcatcaagga      4380
gttcatgcgc ttcaaggtgc gcatggaggg ctccgtgaac ggccacgagt tcgagatcga      4440
gggcgagggc gagggccgcc cctacgaggg cacccagacc gccaagctga aggtgaccaa      4500
gggcggcccc ctgcccttcg cctgggacat cctgtccccc cagttccagt acggctccaa      4560
ggtgtacgtg aagcacccccg ccgacatccc cgactacaag aagctgtcct tcccgagggg      4620
cttcaagtgg gagcgcgtga tgaacttcga ggacggcggc gtggtgaccg tgacccagga      4680
```

```
ctcctccctg caggacggct ccttcatcta caaggtgaag ttcatcggcg tgaacttccc    4740
ctccgacggc cccgtaatgc agaagaagac tatgggctgg gaggcctcca ccgagcgcct    4800 gtaccccgc gacggcgtgc tgaagggcga gatccacaag gccctgaagc tgaaggacgg     4860
cggccactac ctggtggagt tcaagtccat ctacatggcc aagaagcccg tgcagctgcc    4920
cggctactac tacgtggact ccaagctgga catcacctcc cacaacgagg actacaccat    4980
cgtggagcag tacgagcgcg ccgagggccg ccaccacctg ttcctgtagg gccggccatc    5040
aacaactctc ctggcgcacc atcgtcggct acagcctcgg tgacgtgggg caacctagac    5100
ttgtccatct tctggattgg ccaacttaat taatgtatga aataaaagga tgcacacata    5160
gtgacatgct aatcactata atgtgggcat caaagttgtg tgttatgtgt aattactagt    5220
tatctgaata aaagagaaag agatcatcca tatttcttat cctaaatgaa tgtcacgtgt    5280
ctttataatt ctttgatgaa ccagatgcat ttcattaacc aaatccatat acatataaat    5340
attaatcata tataattaat atcaattggg ttagcaaaac aaatctagtc taggtgtgtt    5400
ttgcgaattg cggccgcgat ctgagcttct agaggatccc catcgatggg ccccggccga    5460
agcttgcatg cctgcagtgc agcgtgaccc ggtcgtgccc ctctctagag ataatgagca    5520
ttgcatgtct aagttataaa aaattaccac atattttttt tgtcacactt gtttgaagtg    5580
cagtttatct atctttatac atatatttaa actttactct acgaataata taatctatag    5640
tactacaata atatcagtgt tttagagaat catataaatg aacagttaga catggtctaa    5700
aggacaattg agtattttga caacaggact ctacagtttt atcttttag tgtgcatgtg     5760 ttctcctttt tttttgcaaa tagcttcacc tatataatac ttcatccatt ttattagtac    5820
atccatttag ggtttagggt taatggtttt tatagactaa ttttttttagt acatctattt    5880 tattctattt tagcctctaa attaagaaaa ctaaaactct attttagttt ttttatttaa    5940
taatttagat ataaaataga ataaaataaa gtgactaaaa attaaacaaa taccctttaa    6000
gaaattaaaa aaactaagga aacattttc ttgtttcgag tagataatgc cagcctgtta     6060
aacgccgtcg acgagtctaa cggacaccaa ccagcgaacc agcagcgtcg cgtcgggcca    6120
agcgaagcag acggcacggc atctctgtcg ctgcctctgg acccctctcg agagttccgc    6180
tccaccgttg gacttgctcc gctgtcggca tccagaaatt gcgtggcgga gcggcagacg    6240
tgagccggca cggcaggcgg cctcctcctc ctctcacggc accggcagct acggggatt     6300 cctttcccac cgctccttcg ctttcccttc ctcgcccgcc gtaataaata gacaccccct    6360
ccacaccctc tttcccaac ctcgtgttgt tcggagcgca cacacacaca accagatctc     6420
ccccaaatcc acccgtcggc acctccgctt caaggtacgc cgctcgtcct ccccccccc    6480 cctctctacc ttctctagat cggcgttccg gtccatgcat ggttagggcc cggtagttct    6540
acttctgttc atgtttgtgt tagatccgtg tttgtgttag atccgtgctg ctagcgttcg    6600
tacacggatg cgacctgtac gtcagacacg ttctgattgc taacttgcca gtgtttctct    6660
ttggggaatc ctgggatggc tctagccgtt ccgcagacgg gatcgatttc atgatttttt    6720
ttgtttcgtt gcatagggtt tggtttgccc ttttccttta tttcaatata tgccgtgcac    6780
ttgtttgtcg gtcatctttt tcatgctttt ttttgtcttg gttgtgatga tgtggtctgg    6840
ttgggcggtc gttctagatc ggagtagaat tctgtttcaa actacctggt ggatttatta    6900
attttggatc tgtatgtgtg tgccatacat attcatagtt acgaattgaa gatgatggat    6960
ggaaatatcg atctaggata ggtatacatg ttgatgcggg ttttactgat gcatatacag    7020
```

```
agatgctttt tgttcgcttg gttgtgatga tgtggtgtgg ttgggcggtc gttcattcgt    7080
tctagatcgg agtagaatac tgtttcaaac tacctggtgt atttattaat tttggaactg    7140
tatgtgtgtg tcatacatct tcatagttac gagtttaaga tggatggaaa tatcgatcta    7200
ggataggtat acatgttgat gtgggtttta ctgatgcata tacatgatgg catatgcagc    7260
atctattcat atgctctaac cttgagtacc tatctattat aataaacaag tatgttttat    7320
aattattttg atcttgatat acttggatga tggcatatgc agcagctata tgtgattttt    7380
tttagccctg ccttcatacg ctatttattt gcttggtact gtttcttttg tcgatgctca    7440
ccctgttgtt tggtgttact tctgcaggtc gactttaact tagcctagga tccacacgac    7500
accatgtccc ccgagcgccg ccccgtcgag atccgcccgg ccaccgccgc cgacatggcc    7560
gccgtgtgcg acatcgtgaa ccactacatc gagacctcca ccgtgaactt ccgcaccgag    7620
ccgcagaccc cgcaggagtg gatcgacgac ctggagcgcc tccaggaccg ctaccgtggg    7680
ctcgtggccg aggtggaggg cgtggtggcc ggcatcgcct acgccggccc gtggaaggcc    7740
cgcaacgcct acgactggac cgtggagtcc accgtgtacg tgtcccaccg ccaccagcgc    7800
ctcggcctcg gctccaccct ctacacccac ctcctcaaga gcatggaggc ccagggcttc    7860
aagtccgtgg tggccgtgat cggcctcccg aacgacccgt ccgtgcgcct ccacgaggcc    7920
ctcggctaca ccgcccgcgg caccctccgc gccgccggct acaagcacgg cggctggcac    7980
gacgtcggct tctggcagcg cgacttcgag ctgccggccc cgccgcgccc ggtgcgcccg    8040
gtgacgcaga tctgagtcga aacctagact tgtccatctt ctggattggc caacttaatt    8100
aatgtatgaa ataaaaggat gcacacatag tgacatgcta atcactataa tgtgggcatc    8160
aaagttgtgt gttatgtgta attactagtt atctgaataa aagagaaaga gatcatccat    8220
atttcttatc ctaaatgaat gtcacgtgtc tttataattc tttgatgaac cagatgcatt    8280
tcattaacca aatccatata catataaata ttaatcatat ataattaata tcaattgggt    8340
tagcaaaaca aatctagtct aggtgtgttt tgcgaatgcg ccgccaccg cggtggagct    8400 cgaattcatt ccgattaatc gtggcctctt gctcttcagg atgaagagct atgtttaaac    8460
gtgcaagcgc tactagacaa ttcagtacat taaaaacgtc cgcaatgtgt tattaagttg    8520
tctaagcgtc aatttgttta caccacaata tatcctgcca ccagccagcc aacagctccc    8580
cgaccggcag ctcggcacaa aatcaccact cgatacaggc agcccatcag tccgggacgg    8640
cgtcagcggg agagccgttg taaggcggca gactttgctc atgttaccga tgctattcgg    8700
aagaacggca actaagctgc cgggtttgaa acacggatga tctcgcggag ggtagcatgt    8760
tgattgtaac gatgacagag cgttgctgcc tgtgatcaaa tatcatctcc ctcgcagaga    8820
tccgaattat cagccttctt attcatttct cgcttaaccg tgacaggctg tcgatcttga    8880
gaactatgcc gacataatag gaaatcgctg gataaagccg ctgaggaagc tgagtggcgc    8940
tatttcttta gaagtgaacg ttgacgatcg tcgggcccag gtagaatccg cctgagtcgc    9000
aagggtgact tcgcctatat tggacgacgg cgcgcagagg gcgacctctt tttgggttac    9060
gattgtagga ttatcactaa aacaatacat gaacatattc aaatggcaat ctctctaagg    9120
cattggaaat aaatacaaat aacagttggg tggagttttt cgacctgagg gcgttaacct    9180
tctgttaacc taaaagctct tgcccaaaca gcagaatcgg cgctaattgc cagcggcgga    9240
acttttccag tttcgcgaaa aatatcgcca ctggcaagga atgggtttga gatggcgaag    9300
tctgtcctaa aagcagcgcc tgtagttgta gggttgacgg ccttgatgga gcgtcatgcc    9360
gatgccctct cgagccaact tcaagcacat catcttaagg ttttcccgcc gcattccgag    9420
```

```
aagggcattc gaacattcgg gccatcggag gcgtccaagc tgctcggcgt tggcgagtca   9480
tatttacggc agaccgcgtc tgagatgcca gagttgaatg ttagcatgag cccgggtggc   9540
aggcgaatgt tctcaattga agatatccat gtgattcgga agtatatgga tcaggtcggc   9600
cgcgggaacc ggcgctacct gccacatcgt cgaggcggcg agcagcttca ggttatctct   9660
gtgatgaatt tcaaaggtgg gtcgggtaag accaccaccg ccgcgcatct ggcgcagtac   9720
ctcgctatgc gcggatatcg agtcttggcc attgatctcg atcctcaagc gagcctttct   9780
gcactctttg ggagccaacc ggagacggac gttggcccga acgaaacgct ctacggcgct   9840
ataaggtatg atgatgagca ggtggcaatc gaacgagtcg tccgagggac ttacattccc   9900
gacctccacc tgattcctgg taaccttgag ctgatggagt ttgaacacga tacgccacgc   9960
gcgctgatga accgcaaaga gggcgacacg ctctttttatg gtcgcatcag ccaagtaatt   10020
gaagatatcg cggataacta tgacgtcgtg gtcatcgact gccctcccca gcttgggtat   10080
ctcacgctat ccgcattgac tgcggcgacg tccattcttg tcacggtcca tccgcagatg   10140
ctggatgtga tgtcgatgaa ccagtttctg gcaatgacat cgaaccttt gcgtgaaatc   10200
gagaatgctg gcgccaagtt caagtttaat tggatgcgct atctgataac ccgtttcgaa   10260
ccgagcgacg gaccacagaa ccaaatggta ggttatctgc ggtcgatttt tggcgaaaat   10320
gtcctcaatt ttccgatgct taaaaccacc gcggtttcgg acgctggcct gacaaaccag   10380
actctattcg aagtggagcg tggcctgttc acgcgctcga cctatgatcg agccttggag   10440
gcgatgaacg ccgtcaacga cgagatcgaa acactgatca aaaagcatg gggtaggccc   10500
acatgagccg gaagcacatc cttggcgtct caactgacgc ccctgagacg tcgcccgccg   10560
acaataggac ggcaaagaac cgctccatgc cgctcctcgg cgtaacaagg aaggagcgcg   10620
atccggcaac gaagctcaca gcgaacattg gtaacgcact gcgagagcaa aacgatcgtc   10680
ttagccgtgc cgaagagatc gagcggcgtc tcgctgaagg tcaggcagtg atagagttgg   10740
atgcctcgtc aatagaaccg tctttcgtgc aggatcgtat gcgagggagc attgacgggc   10800
tccttacttc gatccgggaa caaggacagc aagtcccaat ccttgtgcga ccgcatccga   10860
gccagccggg ccgatatcag gttgccttcg gccaccgccg gctacgcgcc gtttcagaac   10920
tcggacttcc ggtcagagcg gtcgttcgcg aactgacgga cgagcaagtg gtcgtagcac   10980
agggtcagga aaacaatgag cgcgaagatc ttaccttcat cgaaaaggcg cgcttcgcac   11040
atcgcctgaa caggcagttt tctcgagaga ttgtcatcgc cgcgatgtcg atcgacaaga   11100
gcaatttgtc caagatgctt ctgctcgttg acgccctccc ctctgaactg accgatgcta   11160
ttggtgccgc tcctggtgtt ggacggccga gttggcaaca acttgccgag ctgattgaga   11220
aagtttcttc accggccgac gtggctaaat atgctatgtc ggaggaagtt caagcgctgc   11280
catcggcaga acgattcaag gcggtgatcg ctagtctgaa gcccagtcgg gttgcgcgtg   11340
gacttcccga ggtcatggcc accccagacg gcaccgaaat tgcacaggtg acgcagagca   11400
aggccaaact ggaaatcacg attgacagga aggcgacgcc cgattttgcg accttcgtgc   11460
tcgatcatgt gccagcgctg tatcaagcgt accacgctga gaaccaacgg aaacggggag   11520
agtaaaccgc aaaagaaaag agcccccctca acgtcgccgt cgcggaagcc cttctgtctc   11580
tctagcgcga acagaatcgc atttcctcga atcctcgtca agagttttta gcgccgtttt   11640
ggtgagctga tttcctttgc ctgctgaaag gtgaaagatg atgcagacag gaagtgtaac   11700
gacgccattc gggcggcggc caatgacgct tgcgcttgtg cggcgccaga cggcgctggc   11760
```

```
cgatatcaaa caaggcaaga cagcggacaa gtggaaggtc tttagagacg cgtccgcggc   11820
tatgaaacta cttggaatcc agtccaacag tcttgccgtc cttgatgcgc tattgagctt   11880
tcacccggaa acggagttgc gtcaggaggc acagctgatc gtcttcccgt cgaatgctca   11940
gcttgcccct cgggcgcatg ggatggctgg cgcgactttg cgtaggcaca tcgccatgct   12000
cgtggagtca ggcttgatcg tccggaagga tagcgccaac ggaaagcgtt acgtcgtaa    12060
ggatggcgct ggtcagatcg agcgcgcgtt tggcttcgat ttgtctccgc ttctcgcgcg   12120
gtccgaagag ctagcgatga tggcacagca ggtgatggcc gatcgagcag cattcaggat   12180
ggccaaagaa agtctgacga tttgccgacg ggacgttcgg aagctaatta cggcagctat   12240
ggaagaggga gcggagggcg actggcaagc tgtcgaggaa gtctatgtgg aacttgtggg   12300
tagaattcca cgcgccccga cgcttgctga tgtagagtca attctcgaag agatgtggat   12360
gctccaggaa gagataatca accggttgga aattagagac aattcagaaa ataatagcac   12420
caatgctgcc cagagcgagc agcacataca gaattcaaaa cccgaatccg ttaatgaact   12480
tgaacctcgc tctgaaaagg agcagggcgc taagccgagt gaaatagacc gggcaaggag   12540
cgagccgata aaagcgttcc ccctcgggat gatcctgaaa gcatgcccga ccattggcaa   12600
ttatgggccg agcggtgcgg ttgctagctg gcgtgacctc atgtcggctg cggtggtggt   12660
tcggtctatg ctgggggtca gcccgtcggc ttaccaagac gcgtgtgagg caatgggacc   12720
ggagaatgcg gcagcagcga tggcgtgcat tttggagcga gcgaacttca tcaattcgcc   12780
cgggggctat ctccgagatc tgacacggcg gagcgagctt gggaagtttt cacttggccc   12840
gatgataatg gcgctcttga aggctagcgg gcaggggacg ttgcggtttg gctagaatta   12900
gcgagtatgg agcaggatgg tctgtggtca gctgaccaca gacctaatag gttgaaaaca   12960
tgagcgtttt ttggatgatc gacagaccat ccgattcccg gagtaccaag cgtgctctga   13020
tgggagcgat aacattactc aacaagcacg aaggccccat gccgatcgtt gatcgtgaag   13080
gagagcctgc tctacatgcg gcggtatttt gccggccgag gcatgtagtc gcggagcact   13140
gcctatttac tgccctaggc acaaacgttg actcttggat cgagctggca gacaaagcaa   13200
taacccacac agaggacgat taatggctga cgaagagatc cagaatccgc cggacggtac   13260
tgctgctgcc gaagttgagc cggctgctcc tagaggtaga agagcaaaga aagcaccagc   13320
cgaaacagcc cgcacgggat cgttcaaatc cgtgaagccg aaaacccgcg gcctcagcaa   13380
ccgagaaaaa ctggagaaga tcggtcaaat cgaagctcag gtcgctggcg gcgcaacctt   13440
gaaggacgcc gttaagatcg tgggtatttc cgttcagacc tattatcaat ggaagagagc   13500
tgcggttcaa cctgtctcac agaatccggc cgtgtctgtt tcagttgacg atgaactcgg   13560
cgagttcatc caactcgagg aggaaaatat gcatggcatg cccgttccat acagaagctg   13620
ggcgaacaaa cgatgctcgc cttccagaaa accgaggatg cgaaccactt catccggggt   13680
cagcaccacc ggcaagcgcc gcgacggccg aggtcttccg atctcctgaa gccagggcag   13740
atccgtgcac agcaccttgc cgtagaagaa cagcaaggcc gccaatgcct gacgatgcgt   13800
ggagaccgaa accttgcgct cgttcgccag ccaggacaga aatgcctcga cttcgctgct   13860
gcccaaggtt gccgggtgac gcacaccgtg gaaacggatg aaggcacgaa cccagtggac   13920
ataagcctgt tcggttcgta agctgtaatg caagtagcgt atgcgctcac gcaactggtc   13980
cagaaccttg accgaacgca gcggtggtaa cggcgcagtg gcggttttca tggcttgtta   14040
tgactgtttt tttggggtac agtctatgcc tcgggcatcc aagcagcaag cgcgttacgc   14100
cgtgggtcga tgtttgatgt tatggagcag caacgatgtt acgcagcagg gcagtcgccc   14160
```

```
taaaacaaag ttaaacatca tgagggaagc ggtgatcgcc gaagtatcga ctcaactatc   14220
agaggtagtt ggcgtcatcg agcgccatct cgaaccgacg ttgctggccg tacatttgta   14280
cggctccgca gtggatggcg gcctgaagcc acacagtgat attgatttgc tggttacggt   14340
gaccgtaagg cttgatgaaa caacgcggcg agctttgatc aacgaccttt tggaaacttc   14400
ggcttcccct ggagagagcg agattctccg cgctgtagaa gtcaccattg ttgtgcacga   14460
cgacatcatt ccgtggcgtt atccagctaa gcgcgaactg caatttggag aatggcagcg   14520
caatgacatt cttgcaggta tcttcgagcc agccacgatc gacattgatc tggctatctt   14580
gctgacaaaa gcaagagaac atagcgttgc cttggtaggt ccagcggcgg aggaactctt   14640
tgatccggtt cctgaacagg atctatttga ggcgctaaat gaaaccttaa cgctatggaa   14700
ctcgccgccc gactgggctg gcgatgagcg aaatgtagtg cttacgttgt cccgcatttg   14760
gtacagcgca gtaaccggca aaatcgcgcc gaaggatgtc gctgccgact gggcaatgga   14820
gcgcctgccg gcccagtatc agcccgtcat acttgaagct agacaggctt atcttggaca   14880
agaagaagat cgcttggcct cgcgcgcaga tcagttggaa gaatttgtcc actacgtgaa   14940
aggcgagatc accaaggtag tcggcaaata atgtctaaca attcgttcaa gccgacgccg   15000
cttcgcggcg cggcttaact caagcgttag atgcactata cgtaaccaac tagtgcgctc   15060
ttccgcttcc tcgctcactg actcgctgcg ctcggtcgtt cggctgcggc gagcggtatc   15120
agctcactca aaggcggtaa tacggttatc cacagaatca ggggataacg caggaaagaa   15180
catgtgagca aaaggccagc aaaaggccag gaaccgtaaa aaggccgcgt tgctggcgtt   15240
tttccatagg ctccgccccc ctgacgagca tcacaaaaat cgacgctcaa gtcagaggtg   15300
gcgaaacccg acaggactat aaagatacca ggcgtttccc cctggaagct ccctcgtgcg   15360
ctctcctgtt ccgaccctgc cgcttaccgg atacctgtcc gcctttctcc cttcgggaag   15420
cgtggcgctt tctcatagct cacgctgtag gtatctcagt tcggtgtagg tcgttcgctc   15480
caagctgggc tgtgtgcacg aaccccccgt tcagcccgac cgctgcgcct tatccggtaa   15540
ctatcgtctt gagtccaacc cggtaagaca cgacttatcg ccactggcag cagccactgg   15600
taacaggatt agcagagcga ggtatgtagg cggtgctaca gagttcttga agtggtggcc   15660
taactacggc tacactagaa ggacagtatt tggtatctgc gctctgctga agccagttac   15720
cttcggaaaa agagttggta gctcttgatc cggcaaacaa accaccgctg gtagcggtgg   15780
tttttttgtt tgcaagcagc agattacgcg cagaaaaaaa ggatctcaag aagatccttt   15840
gatcttttct acggggtctg acgctcagtg gaacgaaaac tcacgttaag ggattttggt   15900
catgagatta tcaaaaagga tcttcaccta gatccttttt aattaaaaat gaagcgtacc   15960
gacgatcttg ctgcgttcgg atattttcgt ggagttcccg ccacagaccc ggattgaagg   16020
cgagatccag caactcgcgc cagatcatcc tgtgacggaa cttggcgcg tgatgactgg   16080 ccaggacgtc ggccgaaaga gcgacaagca gatcacgctt ttcgacagcg tcggatttgc   16140
gatcgaggat ttttcggcgc tgcgctacgt ccgcgaccgc gttgagggat caagccacag   16200
cagcccactc gaccttctag ccgacccaga cgagccaagg gatcttttg gaatgctgct   16260 ccgtcgtcag gctttccgac gtttgggtgg ttgaacagaa gtcattatcg cacggaatgc   16320
caagcactcc cgaggggaac cctgtggttg gcatgcacat acaaatggac gaacggataa   16380
accttttcac gccctttta atatccgatt attctaataa acgctctttt ctcttag     16437
```

<210> SEQ ID NO 2

<211> LENGTH: 557
<212> TYPE: DNA
<213> ORGANISM: Arabidopsis thaliana

<400> SEQUENCE: 2

```
taaacttgaa gtctgttaaa tttgatgaca cctctcggta ccaatcgaag aaatctagtg     60
aatttccggg attttagat atctgattct gttgcgaagt tttttatcc ttattagtgt     120
ctgttgagtg tagattgctt ggcgagtagc ccacaataaa gaataaaaa tggcgaatct     180
ttagctttat ttactctgtt tttcatcgaa acagattcag taatatatac tctgtttttt     240
catcttacat ttgtttgcaa aaccgatatt atcaacttct cagtaacaca attcgttcct     300
gaaagagtgc aaaaaaatg ttcctctaca acaccagaag tgttaagagc atcaatcata     360
cactgaaggc caaggattca tgatcacaag tgttaaaagt ttattgtctg acttaaagta     420
agaaacagaa cattaaaagc tttattattc acagttttat tcatggcaag cttaggaaca     480
gtccataact aagatgaaag cggagaagaa gcacaagtgc gaaaaagaaa ccaaattgaa     540
agtgttatta aaagtat                                                   557
```

<210> SEQ ID NO 3
<211> LENGTH: 573
<212> TYPE: DNA
<213> ORGANISM: Arabidopsis thaliana

<400> SEQUENCE: 3

```
ttatggagat tttaagtatc ttttgatgat agtttacaca ctttgaataa gctgattcta     60
ctttatttct ctctgtttgt ttactgcttc agtgttttaa gtcttctctt tgtgtttgtt    120
gctgttgtgt ctttgatgga ttttttgtgat ccgatttaat aaaagaagtg tgttcaaagt    180
aattctctag tctcttttatt tgaaattccg gggatagcag attggtttcc gcaacattga    240
ctccaagttt ataatgatct tgatgatggt ctaaaagttt tgaataagct gactctaatt    300
tactaggttc tgtttgttta tacccttca gagagtttca agtcttctcg ttgtggtctt    360
gttctgttttt cttgatgtga tttcttattc attttaacaa agaagtttg tgcaaagtca    420
caatgcagaa acccactta tttagatttt agataagcaa agcacacaga tgcattatcc    480
ttaagaaaaa caaaatacaa cactagacca caacttcata aactcacaac ataaccttat    540
tcaaatttca gggatatcca gattggttc aca                                  573
```

<210> SEQ ID NO 4
<211> LENGTH: 633
<212> TYPE: DNA
<213> ORGANISM: Arabidopsis thaliana

<400> SEQUENCE: 4

```
gagatgaaga aattgctctt atggttctga aaacttctaa tatgtcgagt tgttctgagt     60
ttaagatttt tccaaaatgt cttttgtcttt tttttatat ctttagagtt acttgaacat    120
tgtgactact tctagggttg ggtttgtgtc aggtctgtta tatcgtgtgg tgggtctgtc    180
taatactgat tcaagttttt gttattcagc taaggaactt ttcttgtttc tgaacaaatc    240
ttttggttcc ctagagtaaa acttgacttc aaaagatag acttcctaag atcactggaa    300
tagataggag tgacaacttg acgtgaaagg tagcttggct atagtaattt tagatctgac    360
aaaacgagat caagaagtta ataatttttca caacaccaat ttgttatcgc ttaaaggttg    420
attgatttgt tcaatagggg gaatcatatt ctcgcatgct cgaaagggg agagaagatg    480
gaatgaacat aacttaaat cggatgtttg attcaacaac aaaactaaac tcagatagag    540
```

| | |
|---|---|
| attatgaagg attccggaat ctgaattaca aaagcaaaat ttaaagctga aaactcctcc | 600 |
| atggtcttac tgtcacctaa agacatttct ttt | 633 |

<210> SEQ ID NO 5
<211> LENGTH: 639
<212> TYPE: DNA
<213> ORGANISM: Arabidopsis thaliana

<400> SEQUENCE: 5

| | |
|---|---|
| aactgagatg gaagaagaag ttgcaatagt ttttttaaac tagtttcttt ctacgtactc | 60 |
| tgttttttct ctgcttggtt catggtttga gtgggcaact actgatcttt cccatttttcc | 120 |
| tgccggattt gtagaagaat aaaaaggttg aaaatgatca tcttgagatg gtgatgaaac | 180 |
| tcttaagatc ctcctcttct gcttctcttt ttatttgccg tgtcataatg aaaattgcat | 240 |
| attcagatgg gcctgtgtgt tgagtaagtg gacctgtgtc cagagagttg attgagatgg | 300 |
| gcttcatttt aggcccacat gtttatcgat caggttcatt ctcttcatta tatgaaagtg | 360 |
| tcctatatcg caacattctc ttcattaatc attatattag tttatcgcca caaagttcac | 420 |
| tattcaaaga ttcgattttt ctctcgcaaa cagaaattta tattgacttt taagaaaaaa | 480 |
| tacaaagtat atctatcaca caactcacaa aagagatagg tacaaacata atgacaaatc | 540 |
| acaataagca caccattata ttaaaagtca aatttacctt tttaataaga agatacaaaa | 600 |
| atatataaag agacgaccaa gacaatttga cttgagtga | 639 |

<210> SEQ ID NO 6
<211> LENGTH: 685
<212> TYPE: DNA
<213> ORGANISM: Arabidopsis thaliana

<400> SEQUENCE: 6

| | |
|---|---|
| tgcggtatac ttggcatttg gttttgctgt acccttttcga aatctttatg tcgttgttta | 60 |
| gtttgttgta ttcgactatc ttcttagact ttgctgaaat tctcaagaga tttttttact | 120 |
| caaacatcag tccacttgtg attggcattt atatttcaaa ctattgcctt agttacatct | 180 |
| tcaatagtcc acttatgaac gatctttagt aaattctctt attcactcgc ttactaagaa | 240 |
| ttaaacctaa agagaataca gaagaattcc ctagagtaag gatttggtgt agtgtaaaac | 300 |
| agactcttcc ctctttgtat tgttcagatt ctggaaacat aagatatgtg aatccaatca | 360 |
| acacagtact cgagatatgt tctgataaaa aaaatgttgg tactaacaat ttcagtttgg | 420 |
| atgggaagga ttatccgaat aaagatatac ctaattctga tcaaaagaga gcgaaaataa | 480 |
| gtctctggag tttagattga gaaactaaat gtcaacaaac cggaaacaaa aaaaaactgt | 540 |
| gtcaagtaac aaaaacaaaa gaaaagactc aagagagta gcagcaacgt aagatttgat | 600 |
| tccaaagtgt ctcacaaggg aggaatgagt aatgctactc cctgttttat tcactcatca | 660 |
| caagtccatc aatcaatcta tctct | 685 |

<210> SEQ ID NO 7
<211> LENGTH: 411
<212> TYPE: DNA
<213> ORGANISM: Arabidopsis thaliana

<400> SEQUENCE: 7

| | |
|---|---|
| gttggtttca tcttatttc tgcgattttt gtacttgctg gatttggaat ccatttgttt | 60 |
| tagctctctc gtataagatt gtctcatctt tgcttgttaa ctctatattt tgaatcatca | 120 |

| | |
|---|---|
| agatatggtt ttgctgttaa tcattgacct tcgatatttt tttgccaatc cgttctctct | 180 |
| accaacctaa gaaaaaatca ctaatatctc acattagagg gtgcaaaatt tggaaggtct | 240 |
| atatcattgt ccaattttct gagtcataca aattctttca tatgattcat tgaacaagac | 300 |
| actcatttac ttataaagcg catttatatg ttcacatgat ttgtacaaaa ctcatgagac | 360 |
| tgcatcaagc agaaagtatt tatttatctt tacatgtcaa agctttgaga a | 411 |

<210> SEQ ID NO 8
<211> LENGTH: 457
<212> TYPE: DNA
<213> ORGANISM: Arabidopsis thaliana

<400> SEQUENCE: 8

| | |
|---|---|
| taacatcaaa gagcaggaag ttttttaacaa ggaatctggt cgagacatcc atgttctgga | 60 |
| ccagacagtt ttttggttta gccttaaaat tccaaggttg tataagaaga acacactgtt | 120 |
| tgttattctt tgcggttggt aaccaatata gtaatatcag tatttcgtct caatctctct | 180 |
| tgttcttata ataatagaat gagaaatcga atggaatttt catgtgaag tggattagta | 240 |
| acattatcac aattgataaa acatttgtaa ataactagac aagctttctc ggctatcagt | 300 |
| taaaatagaa gttgaattaa cctcacaatt cgttttgtac ggaactaaga gatcacaaat | 360 |
| gaaaacggaa acaacaaca aaaatgaaaa agcgatactt ttttaaacca ccctgtcatc | 420 |
| ctcatctcaa agagcttctt gacttccatg agtgcta | 457 |

<210> SEQ ID NO 9
<211> LENGTH: 557
<212> TYPE: DNA
<213> ORGANISM: Arabidopsis thaliana

<400> SEQUENCE: 9

| | |
|---|---|
| atacttttaa taacactttc aatttggttt cttttttcgca cttgtgcttc ttctccgctt | 60 |
| tcatcttagt tatggactgt tcctaagctt gccatgaata aaactgtgaa taataaagct | 120 |
| tttaatgttc tgtttcttac tttaagtcag acaataaact tttaacactt gtgatcatga | 180 |
| atccttggcc ttcagtgtat gattgatgct cttaacactt ctggtgttgt agaggaacat | 240 |
| tttttttgca ctctttcagg aacgaattgt gttactgaga agttgataat atcggttttg | 300 |
| caaacaaatg taagatgaaa aaacagagta tatattactg aatctgtttc gatgaaaaac | 360 |
| agagtaaata aagctaaaga ttcgccattt ttatttcttt attgtgggct actcgccaag | 420 |
| caatctacac tcaacagaca ctaataagga taaaaaaact tcgcaacaga atcagatatc | 480 |
| taaaaatccc ggaaattcac tagatttctt cgattggtac cgagaggtgt catcaaattt | 540 |
| aacagacttc aagttta | 557 |

<210> SEQ ID NO 10
<211> LENGTH: 573
<212> TYPE: DNA
<213> ORGANISM: Arabidopsis thaliana

<400> SEQUENCE: 10

| | |
|---|---|
| tgtgaaacca atctggatat ccctgaaatt tgaataaggt tatgttgtga gtttatgaag | 60 |
| ttgtggtcta gtgttgtatt tgttttttct taaggataat gcatctgtgt gctttgctta | 120 |
| tctaaaatct aaataaagtg ggtttctgca ttgtgacttt gcacaaactt cttttgttaa | 180 |
| aatgaataag aaatcacatc aagaaaacag aacaagacca caacgagaag acttgaaact | 240 |
| ctctgaaggt atataaacaa acagaaccta gtaaattaga gtcagcttat tcaaaacttt | 300 |

```
tagaccatca tcaagatcat tataaacttg gagtcaatgt tgcggaaacc aatctgctat      360
ccccggaatt tcaaataaag agactagaga attactttga acacacttct tttattaaat      420
cggatcacaa aaatccatca aagacacaac agcaacaaac acaaagagaa gacttaaaac      480
actgaagcag taaacaaaca gagagaaata agtagaatc agcttattca aagtgtgtaa      540
actatcatca aaagatactt aaaatctcca taa                                   573
```

```
<210> SEQ ID NO 11
<211> LENGTH: 633
<212> TYPE: DNA
<213> ORGANISM: Arabidopsis thaliana

<400> SEQUENCE: 11
aaaagaaatg tctttaggtg acagtaagac catggaggag ttttcagctt taaattttgc       60
ttttgtaatt cagattccgg aatccttcat aatctctatc tgagtttagt tttgttgttg      120
aatcaaacat ccgatttaaa gttatgttca ttccatcttc tctcccctt tcgagcatgc       180 gagaatatga ttccccctat tgaacaaatc aatcaacctt aagcgataa caaattggtg       240 ttgtgaaaat tattaacttc ttgatctcgt tttgtcagat ctaaaattac tatagccaag      300
ctacctttca cgtcaagttg tcactcctat ctattccagt gatcttagga agtctatctt      360
ttggaagtca agttttactc tagggaacca aaagatttgt tcagaaacaa gaaaagttcc      420
ttagctgaat aacaaaaact tgaatcagta ttagacagac ccaccacacg atataacaga      480
cctgacacaa acccaaccct agaagtagtc acaatgttca gtaactcta aagatataaa      540 aaaaaagaca agacatttt ggaaaatctt aaaactcaga acaactcgac atattagaag      600
ttttcagaac cataagagca atttcttcat ctc                                   633
```

```
<210> SEQ ID NO 12
<211> LENGTH: 639
<212> TYPE: DNA
<213> ORGANISM: Arabidopsis thaliana

<400> SEQUENCE: 12
tcactcaagt caaattgtct tggtcgtctc tttatatatt tttgtatctt cttattaaaa       60
aggtaaattt gacttttaat ataatggtgt gcttattgtg atttgtcatt atgtttgtac      120
ctatctcttt tgtgagttgt gtgatagata tactttgtat tttttcttaa aagtcaatat      180
aaatttctgt ttgcgagaga aaaatcgaat cttgaatag tgaactttgt ggcgataaac      240
taatataatg attaatgaag agaatgttgc gatataggac actttcatat aatgaagaga      300
atgaacctga tcgataaaca tgtgggccta aaatgaagcc catctcaatc aactctctgg      360
acacaggtcc acttactcaa cacacaggcc catctgaata tgcaattttc attatgacac      420
ggcaaataaa aagagaagca gaagaggagg atcttaagag tttcatcacc atctcaagat      480
gatcattttc aacctttta ttcttctaca aatccggcag gaaatggga agatcagta       540 gttgcccact caaaccatga accaagcaga gaaaaacag agtacgtaga aagaaactag      600
tttaaaaaaa ctattgcaac ttcttcttcc atctcagtt                             639
```

```
<210> SEQ ID NO 13
<211> LENGTH: 685
<212> TYPE: DNA
<213> ORGANISM: Arabidopsis thaliana

<400> SEQUENCE: 13
```

```
agagatagat tgattgatgg acttgtgatg agtgaataaa acagggagta gcattactca      60
ttcctcccct tgtgagacact ttggaatcaa atcttacgtt gctgctactc tctttgagtc    120
ttttcttttg ttttttgttac ttgacacagt ttttttttgt ttccggtttg ttgacattta   180
gtttctcaat ctaaactcca gagacttatt ttcgctctct tttgatcaga attaggtata    240
tctttattcg gataatcctt cccatccaaa ctgaaattgt tagtaccaac atttttttta    300
tcagaacata tctcgagtac tgtgttgatt ggattcacat atcttatgtt tccagaatct    360
gaacaataca aagagggaag agtctgtttt acactacacc aaatccttac tctagggaat    420
tcttctgtat tctctttagg tttaattctt agtaagcgag tgaataagag aatttactaa    480
agatcgttca taagtggact attgaagatg taactaaggc aatagtttga aatataaatg    540
ccaatcacaa gtggactgat gtttgagtaa aaaaatctct tgagaatttc agcaaagtct    600
aagaagatag tcgaatacaa caaactaaac aacgacataa agatttcgaa agggtacagc    660
aaaaccaaat gccaagtata ccgca                                          685

<210> SEQ ID NO 14
<211> LENGTH: 411
<212> TYPE: DNA
<213> ORGANISM: Arabidopsis thaliana

<400> SEQUENCE: 14
ttctcaaagc tttgacatgt aaagataaat aaatactttc tgcttgatgc agtctcatga      60
gttttgtaca aatcatgtga acatataaat gcgctttata agtaaatgag tgtcttgttc    120
aatgaatcat atgaaagaat ttgtatgact cagaaaattg gacaatgata tagaccttcc    180
aaattttgca ccctctaatg tgagatatta gtgattttt cttaggttgg tagagagaac     240
ggattggcaa aaaatatcg aaggtcaatg attaacagca aaaccatatc ttgatgattc     300
aaaatataga gttaacaagc aaagatgaga caatcttata cgagagagct aaaacaaatg    360
gattccaaat ccagcaagta caaaaatcgc agaaaataag atgaaaccaa c             411

<210> SEQ ID NO 15
<211> LENGTH: 457
<212> TYPE: DNA
<213> ORGANISM: Arabidopsis thaliana

<400> SEQUENCE: 15
tagcactcat ggaagtcaag aagctctttg agatgaggat gacagggtgg tttaaaaaag      60
tatcgctttt tcattttgt tgttgttttc cgttttcatt tgtgatctct tagttccgta     120
caaaacgaat tgtgaggtta attcaacttc tattttaact gatagccgag aaagcttgtc    180
tagttattta caaatgtttt atcaattgtg ataatgttac taatccactt cacatgaaaa    240
ttccatttcg atttctcatt ctattattat aagaacaaga gagattgaga cgaaatactg    300
atattactat attggttacc aaccgcaaag aataacaaac agtgtgttct tcttatacaa    360
ccttggaatt ttaaggctaa accaaaaaac tgtctggtcc agaacatgga tgtctcgacc    420
agattccttg ttaaaaactt cctgctcttt gatgtta                             457

<210> SEQ ID NO 16
<211> LENGTH: 782
<212> TYPE: DNA
<213> ORGANISM: Oryza Sativa

<400> SEQUENCE: 16
gcattgtttt gatgctgcta cctataaaag tatgagcttc agatgagaat ttagagagct      60
```

```
cccctgaggc aatgggttat gactttgtta tcatcttagt actactccta tctaagggac      120
ggtgtaaggc tgtaatctat gtgcggtgca atgataaggc tatcctttct gcgtttgatc      180
atgacatctc atcgctgttc gattctttct cgctggcgtc tgttatgttg aatgatgcaa      240
ttcttctgta agattccgcc tttaccgaaa tatctctagt atcaaattta aattggagta      300
cggatcctct ttgaacatac ggatctattt gagataattt tgtctgatca tcaacgagaa      360
ctcggaagcg tgccaacctt gtgggtcaat tgtaacgata aagcagggag aatatagttc      420 ccccttttc ctctgatgat gaaatggcag agaagtgta gttgagcctg ctgttttggt        480
gaagactgaa atggtatcag aaagtcagaa tccactataa ccaatacaac agcagctgat      540
atataatcat tgatcaagga aaacaactgc agctcataga ttaatgctta ctagctttgt      600
ccatcaatac atcaaaaac cagtccaaca gtcatggtaa ctgctccaaa tcaaagcacg       660
ccagaagttc tcttaacgcc tcacacagca ggaaacacaa caacaaactg gattttattt     720
atctacacat ccatcatatt tacataccaa gggagaatcc gcaggactca ttttcctttc     780
tt                                                                     782

<210> SEQ ID NO 17
<211> LENGTH: 825
<212> TYPE: DNA
<213> ORGANISM: Oryza Sativa

<400> SEQUENCE: 17
aggcagcagc agtatccaac tagtcatgta tccagcctaa attgaaaagt cagatcatgt       60
gtaacatggc cctcaatatt tcgatgttgc cttgtggaaa aatagctgg tattggtact       120 gtgttttta ctccttccag ctaccgacgt tcagtgttag tgcacaaaat gttcatccat       180
ggtagtttgt ctacattgca gtcatgtaaa gttaaacatt cacgatttct gtacttttgc      240
atgtgtaact aaatgaaatg gtgtgttaca ttcattcctt caatcaaata atccatagaa      300
acaaactggt ttgtaactat tgtaactagt cgctagtgtc catggtattt tcgattgtgg      360
aacataatta gttaatctg cttcagtata acttaagccg ctttatcct gtgtatgcat        420 cagcttcgct ccattgaaca tccaaacatc agtataagca ttttgtggcg actaatcatc      480
cggagatagg gcaatgcttt ctaccaactg aagagtagag acgtgatgct gtgagatgga     540
atgcaaattt cgcatattag taagaagttg gggaaggatt cgaccactca ctgagaagct     600
agagcatcat ggcacagtaa ttacaatgta acgtagcata ttcttgaaca agaacatctg     660
gtcaaatacc aaccgggaaa aaatccacat cgataaagag gtgccgagtg cttacatcaa     720
cgtctttgcc ataatcagaa cactactccg tacaagctaa cacgagagca gagattacat    780
ttgcacggat gcaaagtttt ccaagatagg gaactggagt gaagc                      825

<210> SEQ ID NO 18
<211> LENGTH: 791
<212> TYPE: DNA
<213> ORGANISM: Oryza Sativa

<400> SEQUENCE: 18
actgagcttt taaagagtg aggtctaggt tctgttgtct gtctgtccat catccatgtg       60
ttgactgttg agggaactcg tttcttcttt tcttcacgag atgagttttt gtgtgcctgt     120
aatactagtt tgtagcaaag gctgcgttac ataaggtgat gagaattgag gtaaaatgag    180
atctgtacac taaattcatt cagactgttt tggcataaag aataatttgg ccttctgcga    240
```

```
tttcagaagc tataaattgc catctcacta aattctcctt ggtcctcatg gcaatgcaac       300
gacagtgtga agcactgaag cccgtaatgc tctatcacca ccatgtacaa cagaaccata       360
tatgtccata tgtacaactc gagtgttgtt tgagtggcca gcaaactggc tgaccaagcc       420
acacgagaga gaatactata aactcaatca tacataacaa gcccaagcaa cagaagacag       480
aacacaacaa cactcgagtc tgggaacagc aacgccgata cactacagca tactgcaacg       540
acacaaagga attggtaagg aaatggcacc aaaatcttgt agatctttag cgagtcattc       600
atttatagca tatgttggaa cagacatgag tcacaagatt tatgatagct tagataacag       660
atggtcggaa ttaaccgccg agagcctata gatgaacaaa aactctgttc caccagtgtt       720
ctcatgctaa aaactttctg aaataccctc ccctgttcac cgaatttctc cacctgttgg       780
atagcagcat t                                                           791

<210> SEQ ID NO 19
<211> LENGTH: 881
<212> TYPE: DNA
<213> ORGANISM: Oryza Sativa

<400> SEQUENCE: 19
ggtgacggcg acgcgatcga acaggtggtg atcgatgctg caacgtgtgt aaatatacag        60
cgccggctgg gtcaagagat ggctcgggtg acgcgcgcgc ggcgtgtcct ggcgttggcg       120
ccggggcatt ctttagtttt tcatcttttc atcatctcag atggtagata caaaacagtg       180
tatgtatgta gctctgtttc tctctataga accccaacaa attttgttgt tgatgttgtt       240
tatcttcata tgctttgatc ttgaaatcgt ctaccttact actgccgatc gttgctcaaa       300
agtgtggaag tttgaagcat cttccacggg cgttgctcta ctcccatctc gtttcaccac       360
gaaatcccct tcgcatagag gcatctcagc cgtacatctc caaacccacg ttctggattc       420
agcaaacgga cggcatatgc cagcggactg actaggattt gtggttcaga ataaaaatat       480
ggtttgcagt gtcaattttc caggagagtg actatgtcat actaacttca tactccaata       540
atgaagctaa gctatctcca tgtacatatc aaatacgaaa tcatatccaa gggaactaac       600
acagtcacaa acaacaggta cacagacaat tacagcacaa gcgcaggagg gaaataattt       660
taactgaact aggaagaaag gaaacacaac tcattttta ttgatatatg ttggatgaat       720
ccaataaaac cgatacaagt cacgaaaaat cagactagat gaatccttcg agatcacatg       780
agcaaaagct ttcgacgaaa gctgtcctat agtcgtggaa gcaataacac ttgataaaga       840
taggaattca gacacgagag gttgcagact ataagatgtc a                          881

<210> SEQ ID NO 20
<211> LENGTH: 772
<212> TYPE: DNA
<213> ORGANISM: Oryza Sativa

<400> SEQUENCE: 20
ccgtggcaat ggctgtcatg ctttggcaca tactaatagc aaggtagaat ggtacagcta        60
tttcattatt tttgcccttg tatatttgta tcactacatg agtaaacgac gtttagttat       120
cgatagtttt gttatgagtg atgaatgatc tgcatcgtac tgccaatgcc ttgcattctc       180
aaatggttgc acacttgcac tcatacaaag ttagtacact ccatcatatt ataaattact       240 ttttttcaa gttaaatttc ctgaaagttt gataaaattt atagaaaaaa tataacgacg       300 cttataaacac taaattaatt tcattacatc taacattaaa catattttga ttttttttg       360 ttttgtgtta aatatattac tatgttttc tataaacttg attaaacata taaagtttta       420
```

| | |
|---|---:|
| acttcaaaaa aaagttaaaa tgacttgtaa tataaaacgt aggcagtaca atgcgaatgt | 480 |
| agggtactcc atccagctga ggtaaaccaa ctccaatata tatacaaaca caaacaacgt | 540 |
| acccaatttt tactgttaaa atacaggcac aatgcctggt atcacacgtt attaagtaga | 600 |
| cagactcgat aaccatgaca cggacaggga cttcttgcca ctggtttacg cacggttaat | 660 |
| attacagacc acacatagag agacggctta gctatttgca ataagcttg acaagataga | 720 |
| tgatgctcca aaaggatgcg atctcagcag ttgagtactt acgctggttc at | 772 |

<210> SEQ ID NO 21
<211> LENGTH: 827
<212> TYPE: DNA
<213> ORGANISM: Oryza Sativa

<400> SEQUENCE: 21

| | |
|---|---:|
| acaccacctg ctgtctgcgc ttgtttgttg ccacggctgc gctacaaaca caagccgtat | 60 |
| catctgccga acagctccat cgttagcttc ttttgatgcc ttacatctat cgctggacgt | 120 |
| ttatcgtgcg tacttgtccc atacagggat gtgtttgga tgatttgtag agagggtact | 180 |
| gtatggcata agatccttca tattaatgtt ctgtgggtca catatcaact tgctattatt | 240 |
| gtattcagcg gttctctctc tattttgcct taagctgtgg taccatttta agtccagtgc | 300 |
| ttgcttttga ttgcttttct gagctttcca ggacatggaa tcgagcctgt gaatgtcgtc | 360 |
| ggccggttta ccttttcgac taataattta aattgtccag tgttggttag aatggagta | 420 |
| tcagattctg gcggtttgca tgctgtttgg tcggcgacgt gccttatcct gaagatttat | 480 |
| atatagtact ttgattgatg tcaagaagga aatttcttta agaaactttt tacaaatagc | 540 |
| gattggtaga actgattaac aacatccacg gctcagaaaa ggaacgcaaa catatttgat | 600 |
| tcttccctaa attaatttgc cattgttatt tttacttgac catccgtcaa aatttacatg | 660 |
| aatacacaac gcacggacga acgatttatt catgtgaagg catgatttac atccttaaaa | 720 |
| ttctctcgca tctagatata gctagagagt ggccagctgc tgactatgca tggagctggc | 780 |
| acggcagtag tgtacaatgc tactgtaatt ttgtattgct acaagta | 827 |

<210> SEQ ID NO 22
<211> LENGTH: 770
<212> TYPE: DNA
<213> ORGANISM: Oryza Sativa

<400> SEQUENCE: 22

| | |
|---|---:|
| gctgaaattt ggttatctgt tatgagcata tctgatttcg atacccactg ttatgaaact | 60 |
| gaataaaccg cattcctgta tgctgggaat tttctcgtta gtgtacgctc caatactcgt | 120 |
| gccgttttca aagacaagca gtgatatgca aagcaatgct gtgtatcttg tgtgttacat | 180 |
| caggagtttt ttttaatggt gatttcgttc atagttttca gacatctgtt tccgtcacac | 240 |
| gttcgtggga atgacttttt tcatatgaaa tgcgcccatg gctgcgcctg aaataatttt | 300 |
| acttgtcccg tttgggatga atgaattctt ttcctgttcg ttgttcagta attcacacag | 360 |
| agtcataaac ataccggtgg aaacatgctc acaagaaaag aaacatcatg aagtcaggct | 420 |
| aaggataaga atagccagca cacctagagc aaaattttac taacatcaga tgcaagaaag | 480 |
| tctacatgag ttctaaaaag gaaactgggg aaaactaatt tacaccaatt atcactaata | 540 |
| gtacactaaa tataaacgac caagaagggc tctaggaacc catttgtat ctagcacccg | 600 |
| aacgttgaac cttctccccg ataaaagagg gatcaggcgt gcaacagact ggctctcacg | 660 |

| ccagggaaac cacaggtaca aaagaggcag cgaaagaaga aacaaaactt ttcctccggg | 720 |
| gcgaacatat acaacttgag aggaaaaata cacaatggcc gagagacaaa | 770 |

<210> SEQ ID NO 23
<211> LENGTH: 814
<212> TYPE: DNA
<213> ORGANISM: Oryza Sativa

<400> SEQUENCE: 23

| agtgttactt attgttgcta ctatccatat tcgctaccat gcttatcatc gctagattaa | 60 |
| aggacatgta ttccagtatg gtcgtgcttt ttgcttggta ctctggtcac atttgtgatg | 120 |
| aatgttcgca gttttcgtgg tcatggtctg gattctacat tccacctaaa gaagttttta | 180 |
| cctggttatt taatccttga gttgttgaat tagctcatgg taattgtcag tagtcttcca | 240 |
| cttggttctc tctgtggatg atcgttcttg ttctctgttt gcgctgtggc tgattgttct | 300 |
| catgttttta aggttttttgg gttagtcact ggtcgcttcg tcactgtgag ccaaaccata | 360 |
| tgccggtagt tttcttcttc accatcatcc gtttgatcct gactcgcgga tctcctaatc | 420 |
| caacttctct cttttttttt tttaatccaa actcacccaa cgttggaaac atagcttgga | 480 |
| acccccttgaa attgaacaga atttatagca ggcaaaaatg taagaaacca cgctagtgta | 540 |
| gcaggcttac agcggggcaa agcagctttt gttaagcaac cacttacgtt agagattcag | 600 |
| agataagcga tgttactttg tttttaccaa catttacata caagcggtac aacacatatt | 660 |
| gccagaaacc acttggtttt ccagccataa ttttttgacaa ttcatgacgc gcgcgcgcac | 720 |
| acacaatgct ggattcacag ggtcacacag ccatgagcca tcagactgga agggctctgt | 780 |
| ttgttcatca catagtcaca gatcgccttg gcct | 814 |

<210> SEQ ID NO 24
<211> LENGTH: 834
<212> TYPE: DNA
<213> ORGANISM: Oryza Sativa

<400> SEQUENCE: 24

| ttggcagcct acccactctg gtaggaaaaa tggaaggggc aagaagatac agtcgatgat | 60 |
| atttgatgtg ctacatacca attgtaatat ttcattcata tctagagcta gaaggatatt | 120 |
| cacttgtatt tcagactctg gttcacggtt taaattgata ttgtggtaga atgctttctt | 180 |
| ggatgggtat atagtgtgac tcgttaaaaa tatgacaaaa cggttcagct actctttaca | 240 |
| agtggtacgg caaattgtag acccaattgc acttggcggt gagctgcttt gttggagcaa | 300 |
| cagggcactg tctgcttgcg tggatgaaaa gctgagtcat ctgaagctag tgaacatttt | 360 |
| ttcgctggct cgctgcgtgt gttttttctc tgattgtggc ccggttgatt atgaaaatga | 420 |
| ccagtaagta aagtcatccg accctgctga tttgtttgtt ttgcctaacc tagctcatgc | 480 |
| tcggggtcgt gaatcgtgct acacttgttg cagctttcgt tttcttgaag agttggaagg | 540 |
| tgtcagctta gcttcctgtg cgtactagta ttgcagaaga aaacgtaaaa ctgtaccaga | 600 |
| gcaagaagac tttgacataa atttgtaaca aggcagatag gtggtacaaa tcaaggcact | 660 |
| cagctgaaca gctcaactga aatgcagaac tgaattgaag agtaaaaatg atccatgcat | 720 |
| gacagacaaa ccagtggaca ctgactgaag atggagcaat gaacaaaata aaatcaagac | 780 |
| ttgttttttat tggcgcatgc atatttaggg tgatatgatg catgacgaaa tgaa | 834 |

<210> SEQ ID NO 25
<211> LENGTH: 740

```
<212> TYPE: DNA
<213> ORGANISM: Oryza Sativa

<400> SEQUENCE: 25
ggtgttccat atagatgatc agatttctat aaccacatga gtacaatgta gagaattcaa      60
atgttttgta accacgtgag ctttgtacgc tatttgcacc acagttctcc ctgtatgttg     120
ttggctcttt tacaattaag aataatgcat gttgaagtat gagtcttcct gtttgcttct     180
ccttgatgat gaaacgctgc tgcatcaact gattattttt cagagaataa acgataaaca     240
aagcacggtg aagtatcgtg taacccacca taagtggtag agccgtagag gtaggactgt     300
gcatgctgaa ttgtaattac catggttagt tcagcagaat ttgcaaaaag gaggacaacag    360
aattagacca tcgtcatgaa ttaatcaagg tacaaaccaa tggttgctgg tacatcagta     420
gcaaatggct gtagcactag cgtgcccata tttatattcc aagcctccaa ggtatacaat     480
acatatttga tgtaccgaac aactgaaaaa ggcgcttggt ttggaagcgc actattttta     540
aatttatagg ataacttctg acagcctttc ttctaaatga acttttggca accgctctga     600
agccgtgtaa cacaatccaa caaagcaatt tgcagtcaaa atttcgggca tgtgccgttc     660
tagttagaat ttaggatgtg actcactaag taattgtgat tgtttctcta tgcaaacacc     720
agccaacagt attgatttca                                                 740

<210> SEQ ID NO 26
<211> LENGTH: 782
<212> TYPE: DNA
<213> ORGANISM: Oryza Sativa

<400> SEQUENCE: 26
aagaaaggaa aatgagtcct gcggattctc ccttggtatg taaatatgat ggatgtgtag      60
ataaataaaa tccagtttgt tgttgtgttt cctgctgtgt gaggcgttaa gagaacttct     120
ggcgtgcttt gatttggagc agttaccatg actgttggac tggttttgt atgtattgat      180
ggacaaagct agtaagcatt aatctatgag ctgcagttgt tttccttgat caatgattat     240
atatcagctg ctgttgtatt ggttatagtg gattctgact ttctgatacc atttcagtct     300
tcaccaaaac agcaggctca actacacttc tcctgccatt tcatcatcag aggaaaaagg     360
gggaactata ttctcccctgc tttatcgtta caattgaccc acaaggttgg cacgcttccg     420
agttctcgtt gatgatcaga caaaattatc tcaaatagat ccgtatgttc aaagaggatc     480
cgtactccaa tttaaatttg atactagaga tatttcggta aaggcggaat cttacagaag     540
aattgcatca ttcaacataa cagacgccag cgagaaagaa tcgaacagcg atgagatgtc     600
atgatcaaac gcagaaagga tagccttatc attgcaccgc acatagatta cagccttaca     660
ccgtccctta gataggagta gtactaagat gataacaaag tcataaccca ttgcctcagg     720
ggagctctct aaattctcat ctgaagctca tactttttata ggtagcagca tcaaaacaat     780
gc                                                                    782

<210> SEQ ID NO 27
<211> LENGTH: 825
<212> TYPE: DNA
<213> ORGANISM: Oryza Sativa

<400> SEQUENCE: 27
gcttcactcc agttccctat cttggaaact tttgcatccg tgcaaatgta atctctgctc      60
tcgtgttagc ttgtacggag tagtgttctg attatggcaa agacgttgat gtaagcactc     120
```

```
ggcacctctt tatcgatgtg attttttcc cggttggtat ttgaccagat gttcttgttc      180
aagaatatgc tacgttacat tgtaattact gtgccatgat gctctagctt ctcagtgagt      240
ggtcgaatcc ttccccaact tcttactaat atgcgaaatt tgcattccat ctcacagcat      300
cacgtctcta ctcttcagtt ggtagaaagc attgccctat ctccggatga ttagtcgcca      360
caaaatgctt atactgatgt ttggatgttc aatggagcga agctgatgca tacacaggat      420
aaagccggct taagttatac tgaagcagat taaactaatt atgttccaca atcgaaaata      480
ccatggacac tagcgactag ttacaatagt tacaaaccag tttgtttcta tggattattt      540
gattgaagga atgaatgtaa cacaccattt catttagtta cacatgcaaa agtcagaaaa      600
tcgtgaatgt ttaactttac atgactgcaa tgtagacaaa ctaccatgga tgaacatttt      660
gtgcactaac actgaacgtc ggtagctgga aggagtaaaa aacacagtac caataccagc      720
tattttttcc acaaggcaac atcgaaatat tgagggccat gttacacatg atctgacttt      780
tcaatttagg ctggatacat gactagttgg atactgctgc tgcct                     825

<210> SEQ ID NO 28
<211> LENGTH: 776
<212> TYPE: DNA
<213> ORGANISM: Oryza Sativa

<400> SEQUENCE: 28
aatgctgcta tccaacaggt ggagaaattc ggtgaacagg gtagggtatt tcagaaagtt       60
tttagcatga gaacactggt ggaacagagt ttttgttcat ctataggctc tcggcggtta      120
attccgacca tctgttatct aagctatcat aaatcttgtg actcatgtct gttccaacat      180
atgctataaa tgaatgactc gctaaagatc tacaagattt tggtgccatt tccttaccaa      240
ttcctttgtg tcgttgcagt atgctgtagt gtatcggcgt tgctgttccc agactcgagt      300
gttgttgtgt tctgtcttct gttgcttggg cttgttatgt atgattgagt ttatagtatt      360
ctctctcgtg tggcttggtc agccagtttg ctggccactc aaacaacact cgagttgtac      420
atatggacat atatggttct gttgtacatg gtggtgatag agcattacgg gcttcagtgc      480
ttcacactgt cgttgcattg ccatgaggac caaggagaat ttagtgagat ggcaatttat      540
agcttctgaa atcgcagaag gccaaattat tctttatgcc aaaacagtct gaatgaattt      600
agtgtacaga tctcatttta cctcaattct catcacctta tgtaacgcag cctttgctac      660
aaactagtat tacaggcaca caaaaactca tctcgtgaag aaaagaagaa acgagttccc      720
tcaacagtca acacatggat gatggacaga cagacaacag aacctagacc tcactc         776

<210> SEQ ID NO 29
<211> LENGTH: 881
<212> TYPE: DNA
<213> ORGANISM: Oryza Sativa

<400> SEQUENCE: 29
tgacatctta tagtctgcaa cctctcgtgt ctgaattcct atctttatca agtgttattg       60
cttccacgac tataggacag ctttcgtcga aagcttttgc tcatgtgatc tcgaaggatt      120
catctagtct gatttttcgt gacttgtatc ggttttattg gattcatcca acatatatca      180
ataaaaaatg agttgtgttt cctttcttcc tagttcagtt aaaattattt ccctcctgcg      240
cttgtgctat aattgtctgt gtacctgttg tttgtgactg tgttagttcc cttggatatg      300
atttcgtatt tgatatgtac atggagatag cttagcttca ttattggagt atgaagttag      360
tatgacatag tcactctcct ggaaaattga cactgcaaac catattttta ttctgaacca      420
```

| | | |
|---|---|---|
| caaatcctag tcagtccgct ggcatatgcc gtccgtttgc tgaatccaga acgtgggttt | 480 |
| ggagatgtac ggctgagatg cctctatgcg aagggyattt cgtggtgaaa cgagatggga | 540 |
| gtagagcaac gcccgtggaa gatgcttcaa acttccacac ttttgagcaa cgatcggcag | 600 |
| tagtaaggta gacgatttca agatcaaagc atatgaagat aaacaacatc aacaacaaaa | 660 |
| tttgttgggg ttctatagag agaaacagag ctacatacat acactgtttt gtatctacca | 720 |
| tctgagatga tgaaaagatg aaaaactaaa gaatgccccg cgccaacgc caggacacgc | 780 |
| cgcgcgcgcg tcacccgagc catctcttga cccagccggc gctgtatatt tacacacgtt | 840 |
| gcagcatcga tcaccacctg ttcgatcgcg tcgccgtcac c | 881 |

<210> SEQ ID NO 30
<211> LENGTH: 772
<212> TYPE: DNA
<213> ORGANISM: Oryza Sativa

<400> SEQUENCE: 30

| | |
|---|---|
| atgaaccagc gtaagtactc aactgctgag atcgcatcct tttggagcat catctatctt | 60 |
| gtcaagctta tttgcaaata gctaagccgt ctctctatgt gtggtctgta atattaaccg | 120 |
| tgccgtaaacc agtggcaaga agtccctgtc cgtgtcatgg ttatcgagtc tgtctactta | 180 |
| ataacgtgtg ataccaggca ttgtgcctgt attttaacag taaaaattgg gtacgttgtt | 240 |
| tgtgttttgta tatatattgg agttggttta cctcagctgg atggagtacc ctacattcgc | 300 |
| attgtactgc ctacgtttta tattacaagt cattttaact ttttttttgaa gttaaacttt | 360 |
| tatatgttta atcaagttta tagaaaaaca tagtaatata tttaacacaa acaaaaaaa | 420 |
| aatcaaaata tgtttaatgt tagatgtaat gaaattaatt tagtgttata agcgtcgtta | 480 |
| tattttttct ataaattta tcaaactttc aggaaattta acttgaaaaa aaagtaattt | 540 |
| ataatatgat ggagtgtact aactttgtat gagtgcaagt gtgcaaccat ttgagaatgc | 600 |
| aaggcattgg cagtacgatg cagatcattc atcactcata acaaaactat cgataactaa | 660 |
| acgtcgttta ctcatgtagt gatacaaata tacaagggca aaaataatga aatagctgta | 720 |
| ccattctacc ttgctattag tatgtgccaa agcatgacag ccattgccac gg | 772 |

<210> SEQ ID NO 31
<211> LENGTH: 827
<212> TYPE: DNA
<213> ORGANISM: Oryza Sativa

<400> SEQUENCE: 31

| | |
|---|---|
| tacttgtagc aatacaaaat tacagtagca ttgtacacta ctgccgtgcc agctccatgc | 60 |
| atagtcagca gctggccact ctctagctat atctagatgc gagagaattt taaggatgta | 120 |
| aatcatgcct tcacatgaat aaatcgttcg tccgtgcgtt gtgtattcat gtaaattttg | 180 |
| acggatggtc aagtaaaaat aacaatggca aattaattta gggaagaatc aaatatgttt | 240 |
| gcgttccttt tctgagccgt ggatgttgtt aatcagttct accaatcgct atttgtaaaa | 300 |
| agtttcttaa agaaatttcc ttcttgacat caatcaaagt actatatata aatcttcagg | 360 |
| ataaggcacg tcgccgacca aacagcatgc aaaccgccag aatctgatac tccattccta | 420 |
| accaacactg gacaatttaa attattagtc gaaaggataa accggccgac gacattcaca | 480 |
| ggctcgattc catgtcctgg aaagctcaga aaagcaatca aaagcaagca ctggacttaa | 540 |
| aatggtacca cagcttaagg caaaatagag agagaaccgc tgaatacaat aatagcaagt | 600 |

```
tgatatgtga cccacagaac attaatatga aggatcttat gccatacagt accctctcta    660
caaatcatcc aaacacaatc cctgtatggg acaagtacgc acgataaacg tccagcgata    720
gatgtaaggc atcaaaagaa gctaacgatg gagctgttcg gcagatgata cggcttgtgt    780
ttgtagcgca gccgtggcaa caaacaagcg cagacagcag gtggtgt                  827

<210> SEQ ID NO 32
<211> LENGTH: 770
<212> TYPE: DNA
<213> ORGANISM: Oryza Sativa

<400> SEQUENCE: 32
tttgtctctc ggccattgtg tattttttcct ctcaagttgt atatgttcgc cccggaggaa    60 aagtttttgtt tcttctttcg ctgcctcttt tgtacctgtg gtttccctgg cgtgagagcc   120
agtctgttgc acgcctgatc cctcttttat cgggagaaag gttcaacgtt cgggtgctag   180
atacaaaatg ggttcctaga gcccttcttg gtcgtttata tttagtgtac tattagtgat   240
aattggtgta aattagtttt ccccagtttc cttttttagaa ctcatgtaga ctttcttgca   300
tctgatgtta gtaaaatttt gctctaggtg tgctggctat tcttatcctt agcctgactt   360
catgatgttt cttctttgt gagcatgttt ccaccggtat gtttatgact ctgtgtgaat    420
tactgaacaa cgaacaggaa aagaattcat tcatcccaaa cgggacaagt aaaattattt   480
caggcgcagc catgggcgca tttcatatga aaaagtcat tccacgaac gtgtgacgga    540 aacagatgtc tgaaaactat gaacgaaatc accattaaaa aaaactcctg atgtaacaca   600
caagatacac agcattgctt tgcatatcac tgcttgtctt tgaaaacggc acgagtattg   660
gagcgtacac taacgagaaa attcccagca tacaggaatg cggtttattc agtttcataa   720
cagtgggtat cgaaatcaga tatgctcata acagataacc aaatttcagc                770

<210> SEQ ID NO 33
<211> LENGTH: 814
<212> TYPE: DNA
<213> ORGANISM: Oryza Sativa

<400> SEQUENCE: 33
aggccaaggc gatctgtgac tatgtgatga acaaacagag cccttccagt ctgatggctc    60
atggctgtgt gaccctgtga atccagcatt gtgtgtgcgc gcgcgcgtca tgaattgtca   120
aaaattatgg ctggaaaacc aagtggtttc tggcaatatg tgttgtaccg cttgtatgta   180
aatgttggta aaaacaaagt aacatcgctt atctctgaat ctctaacgta agtggttgct   240
taacaaaagc tgctttgccc cgctgtaagc ctgctacact agcgtggttt cttacatttt   300
tgcctgctat aaattctgtt caatttcaag gggttccaag ctatgtttcc aacgttgggt   360
gagtttggat taaaaaaaaa aagagagaa gttggattag gagatccgcg agtcaggatc   420
aaacggatga tggtgaagaa gaaaactacc ggcatatggt ttggctcaca gtgacgaagc   480
gaccagtgac taacccaaaa accttaaaaa catgagaaca atcagccaca gcgcaaacag   540
agaacaagaa cgatcatcca cagagagaac caagtggaag actactgaca attaccatga   600
gctaattcaa caactcaagg attaaataac caggtaaaaa cttctttagg tggaatgtag   660
aatccagacc atgaccacga aaactgcgaa cattcatcac aaatgtgacc agagtaccaa   720
gcaaaaagca cgaccatact ggaatacatg tcctttaatc tagcgatgat aagcatggta   780
gcgaatatgg atagtagcaa caataagtaa cact                                 814
```

<210> SEQ ID NO 34
<211> LENGTH: 834
<212> TYPE: DNA
<213> ORGANISM: Oryza Sativa

<400> SEQUENCE: 34

```
ttcatttcgt catgcatcat atcaccctaa atatgcatgc gccaataaaa acaagtcttg      60
attttatttt gttcattgct ccatcttcag tcagtgtcca ctggtttgtc tgtcatgcat     120
ggatcatttt tactcttcaa ttcagttctg catttcagtt gagctgttca gctgagtgcc     180
ttgatttgta ccacctatct gccttgttac aaatttatgt caaagtcttc ttgctctggt     240
acagttttac gttttcttct gcaatactag tacgcacagg aagctaagct gacaccttcc     300
aactcttcaa gaaaacgaaa gctgcaacaa gtgtagcacg attcacgacc ccgagcatga     360
gctaggttag gcaaaacaaa caaatcagca gggtcggatg actttactta ctggtcelttt     420
tcataatcaa ccgggccaca atcagagaaa aaacacacgc agcgagccag cgaaaaaatg     480
ttcactagct tcagatgact cagcttttca tccacgcaag cagacagtgc cctgttgctc     540
caacaaagca gctcaccgcc aagtgcaatt gggtctacaa tttgccgtac cacttgtaaa     600
gagtagctga accgttttgt catatttta acgagtcaca ctatataccc atccaagaaa      660
gcattctacc acaatatcaa tttaaaccgt gaaccagagt ctgaaataca agtgaatatc     720
cttctagctc tagatatgaa tgaaatatta caattggtat gtagcacatc aaatatcatc     780
gactgtatct tcttgcccct tccattttc ctaccagagt gggtaggctg ccaa            834
```

<210> SEQ ID NO 35
<211> LENGTH: 740
<212> TYPE: DNA
<213> ORGANISM: Oryza Sativa

<400> SEQUENCE: 35

```
tgaaatcaat actgttggct ggtgtttgca tagagaaaca atcacaatta cttagtgagt      60
cacatcctaa attctaacta gaacggcaca tgcccgaaat tttgactgca aattgctttg     120
ttggattgtg ttacacggct tcagagcggt tgccaaaagt tcatttagaa gaaaggctgt     180
cagaagttat cctataaatt taaaaatagt gcgcttccaa accaagcgcc ttttcagtt     240
gttcggtaca tcaaatatgt attgtatacc ttggaggctt ggaatataaa tatgggcacg     300
ctagtgctac agccatttgc tactgatgta ccagcaacca ttggtttgta ccttgattaa     360
ttcatgacga tggtctaatt ctgttgtcct cttttgcaa attctgctga actaaccatg     420
gtaattacaa ttcagcatgc acagtcctac ctctacggct ctaccactta tggtgggtta     480
cacgatactt caccgtgctt tgtttatcgt ttattctctg aaaaataatc agttgatgca     540
gcagcgtttc atcatcaagg agaagcaaac aggaagactc atacttcaac atgcattatt     600
cttaattgta aaagagccaa caacatacag ggagaactgt ggtgcaaata gcgtacaaag     660
ctcacgtggt tacaaaacat ttgaattctc tacattgtac tcatgtggtt atagaaatct     720
gatcatctat atggaacacc                                                  740
```

<210> SEQ ID NO 36
<211> LENGTH: 330
<212> TYPE: DNA
<213> ORGANISM: Solanum tuberosum

<400> SEQUENCE: 36

```
cctcggtgac gtggggcaac ctagacttgt ccatcttctg gattggccaa cttaattaat      60
```

```
gtatgaaata aaaggatgca cacatagtga catgctaatc actataatgt gggcatcaaa    120
gttgtgtgtt atgtgtaatt actagttatc tgaataaaag agaaagagat catccatatt    180
tcttatccta aatgaatgtc acgtgtcttt ataattcttt gatgaaccag atgcatttca    240
ttaaccaaat ccatatacat ataaatatta atcatatata attaatatca attgggttag    300
caaaacaaat ctagtctagg tgtgttttgc                                     330

<210> SEQ ID NO 37
<211> LENGTH: 40
<212> TYPE: DNA
<213> ORGANISM: Artificial Sequence
<220> FEATURE:
<223> OTHER INFORMATION: T1 fwd primer

<400> SEQUENCE: 37
aggcaaacaa ggtacctaaa cttgaagtct gttaaatttg                            40

<210> SEQ ID NO 38
<211> LENGTH: 42
<212> TYPE: DNA
<213> ORGANISM: Artificial Sequence
<220> FEATURE:
<223> OTHER INFORMATION: T1 rev primer

<400> SEQUENCE: 38
gccatggatc ggtaccatac ttttaataac actttcaatt tg                         42

<210> SEQ ID NO 39
<211> LENGTH: 41
<212> TYPE: DNA
<213> ORGANISM: Artificial Sequence
<220> FEATURE:
<223> OTHER INFORMATION: T2 fwd primer

<400> SEQUENCE: 39
aggcaaacaa ggtaccttat ggagatttta agtatctttt g                          41

<210> SEQ ID NO 40
<211> LENGTH: 37
<212> TYPE: DNA
<213> ORGANISM: Artificial Sequence
<220> FEATURE:
<223> OTHER INFORMATION: T2 rev primer

<400> SEQUENCE: 40
gccatggatc ggtacctgtg aaaccaatct ggatatc                               37

<210> SEQ ID NO 41
<211> LENGTH: 39
<212> TYPE: DNA
<213> ORGANISM: Artificial Sequence
<220> FEATURE:
<223> OTHER INFORMATION: T3 fwd primer

<400> SEQUENCE: 41
aggcaaacaa ggtaccgaga tgaagaaatt gctcttatg                             39

<210> SEQ ID NO 42
<211> LENGTH: 38
<212> TYPE: DNA
<213> ORGANISM: Artificial Sequence
<220> FEATURE:
<223> OTHER INFORMATION: T3 rev primer

<400> SEQUENCE: 42
```

```
gccatggatc ggtaccaaaa gaaatgtctt taggtgac                                    38
```

<210> SEQ ID NO 43
<211> LENGTH: 39
<212> TYPE: DNA
<213> ORGANISM: Artificial Sequence
<220> FEATURE:
<223> OTHER INFORMATION: T4 fwd primer

<400> SEQUENCE: 43

```
aggcaaacaa ggtaccaact gagatggaag aagaagttg                                   39
```

<210> SEQ ID NO 44
<211> LENGTH: 38
<212> TYPE: DNA
<213> ORGANISM: Artificial Sequence
<220> FEATURE:
<223> OTHER INFORMATION: T4 rev primer

<400> SEQUENCE: 44

```
gccatggatc ggtacctcac tcaagtcaaa ttgtcttg                                    38
```

<210> SEQ ID NO 45
<211> LENGTH: 36
<212> TYPE: DNA
<213> ORGANISM: Artificial Sequence
<220> FEATURE:
<223> OTHER INFORMATION: T5 fwd primer

<400> SEQUENCE: 45

```
aggcaaacaa ggtacctgcg gtatacttgg catttg                                      36
```

<210> SEQ ID NO 46
<211> LENGTH: 38
<212> TYPE: DNA
<213> ORGANISM: Artificial Sequence
<220> FEATURE:
<223> OTHER INFORMATION: T5 rev primer

<400> SEQUENCE: 46

```
gccatggatc ggtaccagag atagattgat tgatggac                                    38
```

<210> SEQ ID NO 47
<211> LENGTH: 39
<212> TYPE: DNA
<213> ORGANISM: Artificial Sequence
<220> FEATURE:
<223> OTHER INFORMATION: T6 fwd primer

<400> SEQUENCE: 47

```
aggcaaacaa ggtaccgttg gtttcatctt attttctgc                                   39
```

<210> SEQ ID NO 48
<211> LENGTH: 40
<212> TYPE: DNA
<213> ORGANISM: Artificial Sequence
<220> FEATURE:
<223> OTHER INFORMATION: T6 rev primer

<400> SEQUENCE: 48

```
gccatggatc ggtaccttct caaagctttg acatgtaaag                                  40
```

<210> SEQ ID NO 49
<211> LENGTH: 37
<212> TYPE: DNA

<213> ORGANISM: Artificial Sequence
<220> FEATURE:
<223> OTHER INFORMATION: T7 fwd primer

<400> SEQUENCE: 49
aggcaaacaa ggtacctaac atcaaagagc aggaagt                          37

<210> SEQ ID NO 50
<211> LENGTH: 36
<212> TYPE: DNA
<213> ORGANISM: Artificial Sequence
<220> FEATURE:
<223> OTHER INFORMATION: T7 rev primer

<400> SEQUENCE: 50
gccatggatc ggtacctagc actcatggaa gtcaag                           36

<210> SEQ ID NO 51
<211> LENGTH: 42
<212> TYPE: DNA
<213> ORGANISM: Artificial Sequence
<220> FEATURE:
<223> OTHER INFORMATION: T8 fwd primer

<400> SEQUENCE: 51
aggcaaacaa ggtaccatac ttttaataac actttcaatt tg                    42

<210> SEQ ID NO 52
<211> LENGTH: 40
<212> TYPE: DNA
<213> ORGANISM: Artificial Sequence
<220> FEATURE:
<223> OTHER INFORMATION: T8 rev primer

<400> SEQUENCE: 52
gccatggatc ggtacctaaa cttgaagtct gttaaatttg                       40

<210> SEQ ID NO 53
<211> LENGTH: 39
<212> TYPE: DNA
<213> ORGANISM: Artificial Sequence
<220> FEATURE:
<223> OTHER INFORMATION: T9 fwd primer

<400> SEQUENCE: 53
aggcaaacaa ggtacctgtg aaaccaatct ggatatccc                        39

<210> SEQ ID NO 54
<211> LENGTH: 38
<212> TYPE: DNA
<213> ORGANISM: Artificial Sequence
<220> FEATURE:
<223> OTHER INFORMATION: T9 rev primer

<400> SEQUENCE: 54
gccatggatc ggtaccttat ggagatttta agtatctt                         38

<210> SEQ ID NO 55
<211> LENGTH: 40
<212> TYPE: DNA
<213> ORGANISM: Artificial Sequence
<220> FEATURE:
<223> OTHER INFORMATION: T10 fwd primer

<400> SEQUENCE: 55
aggcaaacaa ggtaccaaaa gaaatgtctt taggtgacag                       40

<210> SEQ ID NO 56
<211> LENGTH: 39
<212> TYPE: DNA
<213> ORGANISM: Artificial Sequence
<220> FEATURE:
<223> OTHER INFORMATION: T10 rev primer

<400> SEQUENCE: 56
gccatggatc ggtaccgaga tgaagaaatt gctcttatg                              39

<210> SEQ ID NO 57
<211> LENGTH: 39
<212> TYPE: DNA
<213> ORGANISM: Artificial Sequence
<220> FEATURE:
<223> OTHER INFORMATION: T11 fwd primer

<400> SEQUENCE: 57
aggcaaacaa ggtacctcac tcaagtcaaa ttgtcttgg                              39

<210> SEQ ID NO 58
<211> LENGTH: 40
<212> TYPE: DNA
<213> ORGANISM: Artificial Sequence
<220> FEATURE:
<223> OTHER INFORMATION: T11 rev primer

<400> SEQUENCE: 58
gccatggatc ggtaccaact gagatggaag aagaagttgc                             40

<210> SEQ ID NO 59
<211> LENGTH: 39
<212> TYPE: DNA
<213> ORGANISM: Artificial Sequence
<220> FEATURE:
<223> OTHER INFORMATION: T12 fwd primer

<400> SEQUENCE: 59
aggcaaacaa ggtaccagag atagattgat tgatggact                              39

<210> SEQ ID NO 60
<211> LENGTH: 38
<212> TYPE: DNA
<213> ORGANISM: Artificial Sequence
<220> FEATURE:
<223> OTHER INFORMATION: T12 rev primer

<400> SEQUENCE: 60
gccatggatc ggtacctgcg gtatacttgg catttggt                               38

<210> SEQ ID NO 61
<211> LENGTH: 37
<212> TYPE: DNA
<213> ORGANISM: Artificial Sequence
<220> FEATURE:
<223> OTHER INFORMATION: T13 fwd primer

<400> SEQUENCE: 61
aggcaaacaa ggtaccttct caaagctttg acatgta                                37

<210> SEQ ID NO 62
<211> LENGTH: 39
<212> TYPE: DNA
<213> ORGANISM: Artificial Sequence
<220> FEATURE:

<223> OTHER INFORMATION: T13 rev primer

<400> SEQUENCE: 62
gccatggatc ggtaccgttg gtttcatctt attttctgc                39

<210> SEQ ID NO 63
<211> LENGTH: 36
<212> TYPE: DNA
<213> ORGANISM: Artificial Sequence
<220> FEATURE:
<223> OTHER INFORMATION: T14 fwd primer

<400> SEQUENCE: 63
aggcaaacaa ggtacctagc actcatggaa gtcaag                36

<210> SEQ ID NO 64
<211> LENGTH: 36
<212> TYPE: DNA
<213> ORGANISM: Artificial Sequence
<220> FEATURE:
<223> OTHER INFORMATION: T14 rev primer

<400> SEQUENCE: 64
gccatggatc ggtacctaac atcaaagagc aggaag                36

<210> SEQ ID NO 65
<211> LENGTH: 38
<212> TYPE: DNA
<213> ORGANISM: Artificial Sequence
<220> FEATURE:
<223> OTHER INFORMATION: T15 fwd primer

<400> SEQUENCE: 65
aggcaaacaa ggtaccgcat tgttttgatg ctgctacc                38

<210> SEQ ID NO 66
<211> LENGTH: 38
<212> TYPE: DNA
<213> ORGANISM: Artificial Sequence
<220> FEATURE:
<223> OTHER INFORMATION: T15 rev primer

<400> SEQUENCE: 66
gccatggatc ggtaccaaga aaggaaaatg agtcctgc                38

<210> SEQ ID NO 67
<211> LENGTH: 38
<212> TYPE: DNA
<213> ORGANISM: Artificial Sequence
<220> FEATURE:
<223> OTHER INFORMATION: T16 fwd primer

<400> SEQUENCE: 67
aggcaaacaa ggtaccaggc agcagcagta tccaacta                38

<210> SEQ ID NO 68
<211> LENGTH: 38
<212> TYPE: DNA
<213> ORGANISM: Artificial Sequence
<220> FEATURE:
<223> OTHER INFORMATION: T16 rev primer

<400> SEQUENCE: 68
gccatggatc ggtaccgctt cactccagtt ccctatct                38

```
<210> SEQ ID NO 69
<211> LENGTH: 38
<212> TYPE: DNA
<213> ORGANISM: Artificial Sequence
<220> FEATURE:
<223> OTHER INFORMATION: T17 fwd primer

<400> SEQUENCE: 69
aggcaaacaa ggtaccgagt gaggtctagg ttctgttg                              38

<210> SEQ ID NO 70
<211> LENGTH: 38
<212> TYPE: DNA
<213> ORGANISM: Artificial Sequence
<220> FEATURE:
<223> OTHER INFORMATION: T17 rev primer

<400> SEQUENCE: 70
gccatggatc ggtaccaatg ctgctatcca acaggtgg                              38

<210> SEQ ID NO 71
<211> LENGTH: 38
<212> TYPE: DNA
<213> ORGANISM: Artificial Sequence
<220> FEATURE:
<223> OTHER INFORMATION: T18 fwd primer

<400> SEQUENCE: 71
aggcaaacaa ggtaccggtg acggcgacgc gatcgaac                              38

<210> SEQ ID NO 72
<211> LENGTH: 40
<212> TYPE: DNA
<213> ORGANISM: Artificial Sequence
<220> FEATURE:
<223> OTHER INFORMATION: T18 rev primer

<400> SEQUENCE: 72
gccatggatc ggtacctgac atcttatagt ctgcaacctc                            40

<210> SEQ ID NO 73
<211> LENGTH: 36
<212> TYPE: DNA
<213> ORGANISM: Artificial Sequence
<220> FEATURE:
<223> OTHER INFORMATION: T19 fwd primer

<400> SEQUENCE: 73
aggcaaacaa ggtaccccgt ggcaatggct gtcatg                                36

<210> SEQ ID NO 74
<211> LENGTH: 39
<212> TYPE: DNA
<213> ORGANISM: Artificial Sequence
<220> FEATURE:
<223> OTHER INFORMATION: T19 rev primer

<400> SEQUENCE: 74
gccatggatc ggtaccatga accagcgtaa gtactcaac                             39

<210> SEQ ID NO 75
<211> LENGTH: 38
<212> TYPE: DNA
<213> ORGANISM: Artificial Sequence
<220> FEATURE:
<223> OTHER INFORMATION: T20 fwd primer
```

<400> SEQUENCE: 75
aggcaaacaa ggtaccacac cacctgctgt ctgcgctt                                    38

<210> SEQ ID NO 76
<211> LENGTH: 41
<212> TYPE: DNA
<213> ORGANISM: Artificial Sequence
<220> FEATURE:
<223> OTHER INFORMATION: T20 rev primer

<400> SEQUENCE: 76
gccatggatc ggtacctact tgtagcaata caaaattaca g                                41

<210> SEQ ID NO 77
<211> LENGTH: 38
<212> TYPE: DNA
<213> ORGANISM: Artificial Sequence
<220> FEATURE:
<223> OTHER INFORMATION: T21 fwd primer

<400> SEQUENCE: 77
aggcaaacaa ggtaccgctg aaatttggtt atctgtta                                    38

<210> SEQ ID NO 78
<211> LENGTH: 38
<212> TYPE: DNA
<213> ORGANISM: Artificial Sequence
<220> FEATURE:
<223> OTHER INFORMATION: T21 rev primer

<400> SEQUENCE: 78
gccatggatc ggtacctttg tctctcggcc attgtgta                                    38

<210> SEQ ID NO 79
<211> LENGTH: 39
<212> TYPE: DNA
<213> ORGANISM: Artificial Sequence
<220> FEATURE:
<223> OTHER INFORMATION: T22 fwd primer

<400> SEQUENCE: 79
aggcaaacaa ggtaccagtg ttacttattg ttgctacta                                   39

<210> SEQ ID NO 80
<211> LENGTH: 38
<212> TYPE: DNA
<213> ORGANISM: Artificial Sequence
<220> FEATURE:
<223> OTHER INFORMATION: T22 rev primer

<400> SEQUENCE: 80
gccatggatc ggtaccaggc caaggcgatc tgtgacta                                    38

<210> SEQ ID NO 81
<211> LENGTH: 38
<212> TYPE: DNA
<213> ORGANISM: Artificial Sequence
<220> FEATURE:
<223> OTHER INFORMATION: T23 fwd primer

<400> SEQUENCE: 81
aggcaaacaa ggtaccttgg cagcctaccc actctggt                                    38

<210> SEQ ID NO 82
<211> LENGTH: 38

-continued

<212> TYPE: DNA
<213> ORGANISM: Artificial Sequence
<220> FEATURE:
<223> OTHER INFORMATION: T23 rev primer

<400> SEQUENCE: 82
gccatggatc ggtaccttca tttcgtcatg catcatat                              38

<210> SEQ ID NO 83
<211> LENGTH: 38
<212> TYPE: DNA
<213> ORGANISM: Artificial Sequence
<220> FEATURE:
<223> OTHER INFORMATION: T24 fwd primer

<400> SEQUENCE: 83
aggcaaacaa ggtaccggtg ttccatatag atgatcag                              38

<210> SEQ ID NO 84
<211> LENGTH: 38
<212> TYPE: DNA
<213> ORGANISM: Artificial Sequence
<220> FEATURE:
<223> OTHER INFORMATION: T24 rev primer

<400> SEQUENCE: 84
gccatggatc ggtacctgaa atcaatactg ttggctgg                              38

<210> SEQ ID NO 85
<211> LENGTH: 38
<212> TYPE: DNA
<213> ORGANISM: Artificial Sequence
<220> FEATURE:
<223> OTHER INFORMATION: T25 fwd primer

<400> SEQUENCE: 85
aggcaaacaa ggtaccaaga aaggaaaatg agtcctgc                              38

<210> SEQ ID NO 86
<211> LENGTH: 38
<212> TYPE: DNA
<213> ORGANISM: Artificial Sequence
<220> FEATURE:
<223> OTHER INFORMATION: T25 rev primer

<400> SEQUENCE: 86
gccatggatc ggtaccgcat tgttttgatg ctgctacc                              38

<210> SEQ ID NO 87
<211> LENGTH: 38
<212> TYPE: DNA
<213> ORGANISM: Artificial Sequence
<220> FEATURE:
<223> OTHER INFORMATION: T26 fwd primer

<400> SEQUENCE: 87
aggcaaacaa ggtaccgctt cactccagtt ccctatct                              38

<210> SEQ ID NO 88
<211> LENGTH: 38
<212> TYPE: DNA
<213> ORGANISM: Artificial Sequence
<220> FEATURE:
<223> OTHER INFORMATION: T26 rev primer

<400> SEQUENCE: 88
gccatggatc ggtaccaggc agcagcagta tccaacta                              38

<210> SEQ ID NO 89
<211> LENGTH: 38
<212> TYPE: DNA
<213> ORGANISM: Artificial Sequence
<220> FEATURE:
<223> OTHER INFORMATION: T27 fwd primer

<400> SEQUENCE: 89
aggcaaacaa ggtaccaatg ctgctatcca acaggtgg                              38

<210> SEQ ID NO 90
<211> LENGTH: 38
<212> TYPE: DNA
<213> ORGANISM: Artificial Sequence
<220> FEATURE:
<223> OTHER INFORMATION: T27 rev primer

<400> SEQUENCE: 90
gccatggatc ggtaccgagt gaggtctagg ttctgttg                              38

<210> SEQ ID NO 91
<211> LENGTH: 38
<212> TYPE: DNA
<213> ORGANISM: Artificial Sequence
<220> FEATURE:
<223> OTHER INFORMATION: T28 fwd primer

<400> SEQUENCE: 91
aggcaaacaa ggtacctgac atcttatagt ctgcaacc                              38

<210> SEQ ID NO 92
<211> LENGTH: 36
<212> TYPE: DNA
<213> ORGANISM: Artificial Sequence
<220> FEATURE:
<223> OTHER INFORMATION: T28 rev primer

<400> SEQUENCE: 92
gccatggatc ggtaccggtg acggcgacgc gatcga                                36

<210> SEQ ID NO 93
<211> LENGTH: 38
<212> TYPE: DNA
<213> ORGANISM: Artificial Sequence
<220> FEATURE:
<223> OTHER INFORMATION: T29 fwd primer

<400> SEQUENCE: 93
aggcaaacaa ggtaccatga accagcgtaa gtactcaa                              38

<210> SEQ ID NO 94
<211> LENGTH: 36
<212> TYPE: DNA
<213> ORGANISM: Artificial Sequence
<220> FEATURE:
<223> OTHER INFORMATION: T29 rev primer

<400> SEQUENCE: 94
gccatggatc ggtaccccgt ggcaatggct gtcatg                                36

<210> SEQ ID NO 95
<211> LENGTH: 40
<212> TYPE: DNA
<213> ORGANISM: Artificial Sequence

```
<220> FEATURE:
<223> OTHER INFORMATION: T30 fwd primer

<400> SEQUENCE: 95
aggcaaacaa ggtacctact tgtagcaata caaaattaca                           40

<210> SEQ ID NO 96
<211> LENGTH: 38
<212> TYPE: DNA
<213> ORGANISM: Artificial Sequence
<220> FEATURE:
<223> OTHER INFORMATION: T30 rev primer

<400> SEQUENCE: 96
gccatggatc ggtaccacac cacctgctgt ctgcgctt                             38

<210> SEQ ID NO 97
<211> LENGTH: 38
<212> TYPE: DNA
<213> ORGANISM: Artificial Sequence
<220> FEATURE:
<223> OTHER INFORMATION: T31 fwd primer

<400> SEQUENCE: 97
aggcaaacaa ggtacctttg tctctcggcc attgtgta                             38

<210> SEQ ID NO 98
<211> LENGTH: 40
<212> TYPE: DNA
<213> ORGANISM: Artificial Sequence
<220> FEATURE:
<223> OTHER INFORMATION: T31 rev primer

<400> SEQUENCE: 98
gccatggatc ggtaccgctg aaatttggtt atctgttatg                           40

<210> SEQ ID NO 99
<211> LENGTH: 38
<212> TYPE: DNA
<213> ORGANISM: Artificial sequence
<220> FEATURE:
<223> OTHER INFORMATION: T32 fwd primer

<400> SEQUENCE: 99
aggcaaacaa ggtaccaggc caaggcgatc tgtgacta                             38

<210> SEQ ID NO 100
<211> LENGTH: 40
<212> TYPE: DNA
<213> ORGANISM: Artificial sequence
<220> FEATURE:
<223> OTHER INFORMATION: T32 rev primer

<400> SEQUENCE: 100
gccatggatc ggtaccagtg ttacttattg ttgctactat                           40

<210> SEQ ID NO 101
<211> LENGTH: 38
<212> TYPE: DNA
<213> ORGANISM: Artificial sequence
<220> FEATURE:
<223> OTHER INFORMATION: T33 fwd primer

<400> SEQUENCE: 101
aggcaaacaa ggtaccttca tttcgtcatg catcatat                             38
```

<210> SEQ ID NO 102
<211> LENGTH: 38
<212> TYPE: DNA
<213> ORGANISM: Artificial sequence
<220> FEATURE:
<223> OTHER INFORMATION: T33 rev primer

<400> SEQUENCE: 102
gccatggatc ggtaccttgg cagcctaccc actctggt         38

<210> SEQ ID NO 103
<211> LENGTH: 38
<212> TYPE: DNA
<213> ORGANISM: Artificial sequence
<220> FEATURE:
<223> OTHER INFORMATION: T34 fwd primer

<400> SEQUENCE: 103
aggcaaacaa ggtacctgaa atcaatactg ttggctgg         38

<210> SEQ ID NO 104
<211> LENGTH: 38
<212> TYPE: DNA
<213> ORGANISM: Artificial sequence
<220> FEATURE:
<223> OTHER INFORMATION: T34 rev primer

<400> SEQUENCE: 104
gccatggatc ggtaccggtg ttccatatag atgatcag         38

<210> SEQ ID NO 105
<211> LENGTH: 36
<212> TYPE: DNA
<213> ORGANISM: Artificial sequence
<220> FEATURE:
<223> OTHER INFORMATION: PinII fwd primer

<400> SEQUENCE: 105
aggcaaacaa ggtaccctc ggtgacgtgg ggcaac            36

<210> SEQ ID NO 106
<211> LENGTH: 36
<212> TYPE: DNA
<213> ORGANISM: Artificial sequence
<220> FEATURE:
<223> OTHER INFORMATION: Pin II rev primer

<400> SEQUENCE: 106
gccatggatc ggtaccgcaa aacacaccta gactag           36

<210> SEQ ID NO 107
<211> LENGTH: 24
<212> TYPE: DNA
<213> ORGANISM: Artificial Sequence
<220> FEATURE:
<223> OTHER INFORMATION: GUS forward primer for RTPCR

<400> SEQUENCE: 107
atggtccgtc ctgtagaaac ccca                        24

<210> SEQ ID NO 108
<211> LENGTH: 24
<212> TYPE: DNA
<213> ORGANISM: Artificial sequence
<220> FEATURE:
<223> OTHER INFORMATION: GUS reverse primer for RT-PCR

```
<400> SEQUENCE: 108
tcattgtttg cctccctgct gcgg                                           24

<210> SEQ ID NO 109
<211> LENGTH: 20
<212> TYPE: DNA
<213> ORGANISM: Artificial sequence
<220> FEATURE:
<223> OTHER INFORMATION: GUS iF primer

<400> SEQUENCE: 109
caccgcgtct ttgatcgcgt                                                20

<210> SEQ ID NO 110
<211> LENGTH: 20
<212> TYPE: DNA
<213> ORGANISM: Artificial sequence
<220> FEATURE:
<223> OTHER INFORMATION: DsRed iR primer for amplicon B

<400> SEQUENCE: 110
atgtcccagg cgaagggcag                                                20

<210> SEQ ID NO 111
<211> LENGTH: 20
<212> TYPE: DNA
<213> ORGANISM: Artificial sequence
<220> FEATURE:
<223> OTHER INFORMATION: DsRed iR primer for amplicon C

<400> SEQUENCE: 111
ggaagttcac gccgatgaac                                                20

<210> SEQ ID NO 112
<211> LENGTH: 21
<212> TYPE: DNA
<213> ORGANISM: Artificial sequence
<220> FEATURE:
<223> OTHER INFORMATION: DsRed iR priemr for amplicon D

<400> SEQUENCE: 112
ggaacaggtg gtggcggccc t                                              21

<210> SEQ ID NO 113
<211> LENGTH: 21
<212> TYPE: DNA
<213> ORGANISM: Artificial sequence
<220> FEATURE:
<223> OTHER INFORMATION: PinII primer for amplicon E

<400> SEQUENCE: 113
acacacaact ttgatgccca c                                              21

<210> SEQ ID NO 114
<211> LENGTH: 23
<212> TYPE: DNA
<213> ORGANISM: Artificial Sequence
<220> FEATURE:
<223> OTHER INFORMATION: GUS probe

<400> SEQUENCE: 114
aacgtgctga tggtgcacga cca                                            23

<210> SEQ ID NO 115
```

```
<211> LENGTH: 21
<212> TYPE: DNA
<213> ORGANISM: Artificial Sequence
<220> FEATURE:
<223> OTHER INFORMATION: forward primer for GUS qRTPCR

<400> SEQUENCE: 115
cttacgtggc aaaggattcg a                                              21

<210> SEQ ID NO 116
<211> LENGTH: 20
<212> TYPE: DNA
<213> ORGANISM: Artificial Sequence
<220> FEATURE:
<223> OTHER INFORMATION: reverse primer for GUS qRTPCR

<400> SEQUENCE: 116
gccccaatcc agtccattaa                                                20

<210> SEQ ID NO 117
<211> LENGTH: 21
<212> TYPE: DNA
<213> ORGANISM: Artificial Sequence
<220> FEATURE:
<223> OTHER INFORMATION: DsRed probe

<400> SEQUENCE: 117
cggcgtgaac ttcccctccg a                                              21

<210> SEQ ID NO 118
<211> LENGTH: 20
<212> TYPE: DNA
<213> ORGANISM: Artificial Sequence
<220> FEATURE:
<223> OTHER INFORMATION: fwd primer DsRed qRTPCR

<400> SEQUENCE: 118
aggacggctc cttcatctac                                                20

<210> SEQ ID NO 119
<211> LENGTH: 20
<212> TYPE: DNA
<213> ORGANISM: Artificial Sequence
<220> FEATURE:
<223> OTHER INFORMATION: rev primer DsRed qRTPCR

<400> SEQUENCE: 119
gtcttcttct gcattacggg                                                20

<210> SEQ ID NO 120
<211> LENGTH: 22
<212> TYPE: DNA
<213> ORGANISM: Artificial Sequence
<220> FEATURE:
<223> OTHER INFORMATION: MOPAT probe

<400> SEQUENCE: 120
accgtgaact tccgcaccga gc                                             22

<210> SEQ ID NO 121
<211> LENGTH: 21
<212> TYPE: DNA
<213> ORGANISM: Artificial Sequence
<220> FEATURE:
<223> OTHER INFORMATION: fwd primer MOPAT qRTPCR

<400> SEQUENCE: 121
```

```
cgtgaaccac tacatcgaga c                                              21

<210> SEQ ID NO 122
<211> LENGTH: 18
<212> TYPE: DNA
<213> ORGANISM: Artificial Sequence
<220> FEATURE:
<223> OTHER INFORMATION: rev primer MOPAT qRTPCR

<400> SEQUENCE: 122
gtcgatccac tcctgcgg                                                  18

<210> SEQ ID NO 123
<211> LENGTH: 17
<212> TYPE: DNA
<213> ORGANISM: Artificial Sequence
<220> FEATURE:
<223> OTHER INFORMATION: Gr5 probe sequence

<400> SEQUENCE: 123
ttgaagtcac aaagcca                                                   17

<210> SEQ ID NO 124
<211> LENGTH: 21
<212> TYPE: DNA
<213> ORGANISM: Artificial Sequence
<220> FEATURE:
<223> OTHER INFORMATION: fwd primer Gr5 qRTPCR

<400> SEQUENCE: 124
ggcagtttgg ttgatgctca t                                              21

<210> SEQ ID NO 125
<211> LENGTH: 26
<212> TYPE: DNA
<213> ORGANISM: Artificial Sequence
<220> FEATURE:
<223> OTHER INFORMATION: rev primer Gr5 qRTPCR

<400> SEQUENCE: 125
tgctgtatat ctttgctttg aaccat                                         26

<210> SEQ ID NO 126
<211> LENGTH: 39
<212> TYPE: DNA
<213> ORGANISM: Artificial Sequence
<220> FEATURE:
<223> OTHER INFORMATION: primer for polyA mapping

<400> SEQUENCE: 126
gcgacacgac ggcacggttt tttttttttt tttttttt                            39

<210> SEQ ID NO 127
<211> LENGTH: 20
<212> TYPE: DNA
<213> ORGANISM: Artificial Sequence
<220> FEATURE:
<223> OTHER INFORMATION: primer for polyA mapping

<400> SEQUENCE: 127
caccgcgtct ttgatcgcgt                                                20

<210> SEQ ID NO 128
<211> LENGTH: 20
<212> TYPE: DNA
```

```
<213> ORGANISM: Artificial Sequence
<220> FEATURE:
<223> OTHER INFORMATION: primer for polyA mapping

<400> SEQUENCE: 128
gcgacacgac ggcacggttt                                              20

<210> SEQ ID NO 129
<211> LENGTH: 313
<212> TYPE: DNA
<213> ORGANISM: Arabidopsis thaliana

<400> SEQUENCE: 129
taaacttgaa gtctgttaaa tttgatgaca cctctcggta ccaatcgaag aaatctagtg     60
aatttccggg attttagat atctgattct gttgcgaagt ttttttatcc ttattagtgt    120
ctgttgagtg tagattgctt ggcgagtagc ccacaataaa gaaataaaaa tggcgaatct    180
ttagctttat ttactctgtt tttcatcgaa acagattcag taatatatac tctgtttttt    240
catcttacat ttgtttgcaa aaccgatatt atcaacttct cagtaacaca attcgttcct    300
gaaagagtgc aaa                                                      313

<210> SEQ ID NO 130
<211> LENGTH: 296
<212> TYPE: DNA
<213> ORGANISM: Arabidopsis thaliana

<400> SEQUENCE: 130
ttatggagat tttaagtatc ttttgatgat agtttacaca ctttgaataa gctgattcta     60
ctttatttct ctctgtttgt ttactgcttc agtgttttaa gtcttctctt tgtgtttgtt    120
gctgttgtgt ctttgatgga tttttgtgat ccgatttaat aaaagaagtg tgttcaaagt    180
aattctctag tctctttatt tgaaattccg gggatagcag attggtttcc gcaacattga    240
ctccaagttt ataatgatct tgatgatggt ctaaaagttt gaataagct gactct         296

<210> SEQ ID NO 131
<211> LENGTH: 314
<212> TYPE: DNA
<213> ORGANISM: Arabidopsis thaliana

<400> SEQUENCE: 131
gagatgaaga aattgctctt atggttctga aaacttctaa tatgtcgagt tgttctgagt     60
tttaagattt tccaaaatgt cttgtctt tttttttatat ctttagagtt acttgaacat    120
tgtgactact tctagggttg ggtttgtgtc aggtctgtta tatcgtgtgg tgggtctgtc    180
taatactgat tcaagttttt gttattcagc taaggaactt ttcttgtttc tgaacaaatc    240
ttttggttcc ctagagtaaa acttgacttc caaaagatag acttcctaag atcactggaa    300
tagataggag tgac                                                     314

<210> SEQ ID NO 132
<211> LENGTH: 346
<212> TYPE: DNA
<213> ORGANISM: Arabidopsis thaliana

<400> SEQUENCE: 132
aactgagatg gaagaagaag ttgcaatagt tttttaaaac tagtttcttt ctacgtactc     60
tgttttttct ctgcttggtt catggtttga gtgggcaact actgatcttt cccatttcc    120 tgccggattt gtagaagaat aaaaaggttg aaaatgatca tcttgagatg gtgatgaaac    180
```

```
tcttaagatc ctcctcttct gcttctcttt ttatttgccg tgtcataatg aaaattgcat    240
attcagatgg gcctgtgtgt tgagtaagtg gacctgtgtc cagagagttg attgagatgg    300
gcttcatttt aggcccacat gtttatcgat caggttcatt ctcttc                  346
```

<210> SEQ ID NO 133
<211> LENGTH: 333
<212> TYPE: DNA
<213> ORGANISM: Arabidopsis thaliana

<400> SEQUENCE: 133

```
tgcggtatac ttggcatttg gttttgctgt acccttcga aatctttatg tcgttgttta    60
gtttgttgta ttcgactatc ttcttagact ttgctgaaat tctcaagaga ttttttttact 120 caaacatcag tccacttgtg attggcattt atatttcaaa ctattgcctt agttacatct   180
tcaatagtcc acttatgaac gatctttagt aaattctctt attcactcgc ttactaagaa   240
ttaaacctaa agagaataca gaagaattcc ctagagtaag gatttggtgt agtgtaaaac   300
agactcttcc ctctttgtat tgttcagatt ctg                                333
```

<210> SEQ ID NO 134
<211> LENGTH: 219
<212> TYPE: DNA
<213> ORGANISM: Arabidopsis thaliana

<400> SEQUENCE: 134

```
gttggtttca tcttattttc tgcgattttt gtacttgctg gatttggaat ccatttgttt    60
tagctctctc gtataagatt gtctcatctt tgcttgttaa ctctatattt tgaatcatca   120
agatatggtt ttgctgttaa tcattgacct tcgatatttt tttgccaatc cgttctctct   180
accaacctaa gaaaaaatca ctaatatctc acattagag                          219
```

<210> SEQ ID NO 135
<211> LENGTH: 243
<212> TYPE: DNA
<213> ORGANISM: Arabidopsis thaliana

<400> SEQUENCE: 135

```
taacatcaaa gagcaggaag tttttaacaa ggaatctggt cgagacatcc atgttctgga    60
ccagacagtt ttttggttta gccttaaaat tccaaggttg tataagaaga acacactgtt   120
tgttattctt tgcggttggt aaccaatata gtaatatcag tatttcgtct caatctctct   180
tgttcttata ataatagaat gagaaatcga atggaatttt tcatgtgaag tggattagta   240
aca                                                                 243
```

<210> SEQ ID NO 136
<211> LENGTH: 244
<212> TYPE: DNA
<213> ORGANISM: Arabidopsis thaliana

<400> SEQUENCE: 136

```
atacttttaa taacactttc aatttggttt ctttttcgca cttgtgcttc ttctccgctt    60
tcatcttagt tatggactgt tcctaagctt gccatgaata aaactgtgaa taataaagct   120
tttaatgttc tgtttcttac tttaagtcag acaataaact tttaacactt gtgatcatga   180
atccttggcc ttcagtgtat gattgatgct cttaacactt ctggtgttgt agaggaacat   240
tttt                                                                244
```

<210> SEQ ID NO 137
<211> LENGTH: 277
<212> TYPE: DNA
<213> ORGANISM: Arabidopsis thaliana

<400> SEQUENCE: 137

| | | |
|---|---|---|
| tgtgaaacca atctggatat ccctgaaatt tgaataaggt tatgttgtga gtttatgaag | 60 |
| ttgtggtcta gtgttgtatt ttgttttttct taaggataat gcatctgtgt gctttgctta | 120 |
| tctaaaatct aaataaagtg ggtttctgca ttgtgacttt gcacaaactt cttttgttaa | 180 |
| aatgaataag aaatcacatc aagaaaacag aacaagacca caacgagaag acttgaaact | 240 |
| ctctgaaggt atataaacaa acagaaccta gtaaatt | 277 |

<210> SEQ ID NO 138
<211> LENGTH: 319
<212> TYPE: DNA
<213> ORGANISM: Arabidopsis thaliana

<400> SEQUENCE: 138

| | | |
|---|---|---|
| aaaagaaatg tctttaggtg acagtaagac catggaggag ttttcagctt taaattttgc | 60 |
| ttttgtaatt cagattccgg aatccttcat aatctctatc tgagtttagt tttgttgttg | 120 |
| aatcaaacat ccgatttaaa gttatgttca ttccatcttc tctcccctttt tcgagcatgc | 180 |
| gagaatatga ttcccccctat tgaacaaatc aatcaacctt taagcgataa caaattggtg | 240 |
| ttgtgaaaat tattaacttc ttgatctcgt tttgtcagat ctaaaattac tatagccaag | 300 |
| ctacctttca cgtcaagtt | 319 |

<210> SEQ ID NO 139
<211> LENGTH: 293
<212> TYPE: DNA
<213> ORGANISM: Arabidopsis thaliana

<400> SEQUENCE: 139

| | | |
|---|---|---|
| tcactcaagt caaattgtct tggtcgtctc tttatatatt tttgtatctt cttattaaaa | 60 |
| aggtaaattt gacttttaat ataatggtgt gcttattgtg atttgtcatt atgtttgtac | 120 |
| ctatctcttt tgtgagttgt gtgatagata tactttgtat ttttttcttaa aagtcaatat | 180 |
| aaatttctgt ttgcgagaga aaaatcgaat ctttgaatag tgaactttgt ggcgataaac | 240 |
| taatataatg attaatgaag agaatgttgc gatataggac actttcatat aat | 293 |

<210> SEQ ID NO 140
<211> LENGTH: 352
<212> TYPE: DNA
<213> ORGANISM: Arabidopsis thaliana

<400> SEQUENCE: 140

| | | |
|---|---|---|
| agagatagat tgattgatgg acttgtgatg agtgaataaa acagggagta gcattactca | 60 |
| ttcctcccctt gtgagacact ttggaatcaa atcttacgtt gctgctactc tctttgagtc | 120 |
| ttttcttttg tttttgttac ttgacacagt ttttttttgt ttccggtttg ttgacattta | 180 |
| gtttctcaat ctaaactcca gagacttatt ttcgctctct tttgatcaga attaggtata | 240 |
| tctttattcg gataatcctt cccatccaaa ctgaaattgt tagtaccaac attttttta | 300 |
| tcagaacata tctcgagtac tgtgttgatt ggattcacat atcttatgtt tc | 352 |

<210> SEQ ID NO 141
<211> LENGTH: 243

```
<212> TYPE: DNA
<213> ORGANISM: Arabidopsis thaliana

<400> SEQUENCE: 141
ttctcaaagc tttgacatgt aaagataaat aaatactttc tgcttgatgc agtctcatga      60
gttttgtaca aatcatgtga acatataaat gcgctttata agtaaatgag tgtcttgttc     120
aatgaatcat atgaaagaat ttgtatgact cagaaaattg acaatgata tagaccttcc      180 aaattttgca ccctctaatg tgagatatta gtgattttt cttaggttgg tagagagaac      240
gga                                                                   243

<210> SEQ ID NO 142
<211> LENGTH: 286
<212> TYPE: DNA
<213> ORGANISM: Arabidopsis thaliana

<400> SEQUENCE: 142
tagcactcat ggaagtcaag aagctctttg agatgaggat gacagggtgg tttaaaaaag      60
tatcgctttt tcattttgt tgttgttttc cgttttcatt tgtgatctct agttccgta      120 caaaacgaat tgtgaggtta attcaacttc tattttaact gatagccgag aaagcttgtc     180
tagttattta caaatgtttt atcaattgtg ataatgttac taatccactt cacatgaaaa     240
ttccatttcg atttctcatt ctattattat aagaacaaga gagatt                    286

<210> SEQ ID NO 143
<211> LENGTH: 402
<212> TYPE: DNA
<213> ORGANISM: Oryza sativa

<400> SEQUENCE: 143
gcattgtttt gatgctgcta cctataaaag tatgagcttc agatgagaat ttagagagct      60
cccctgaggc aatgggttat gactttgtta tcatcttagt actactccta tctaagggac     120
ggtgtaaggc tgtaatctat gtgcggtgca atgataaggc tatcctttct gcgtttgatc     180
atgacatctc atcgctgttc gattctttct cgctggcgtc tgttatgttg aatgatgcaa     240
ttcttctgta agattccgcc tttaccgaaa tatctctagt atcaaattta aattggagta     300
cggatcctct ttgaacatac ggatctattt gagataattt tgtctgatca tcaacgagaa     360
ctcggaagcg tgccaacctt gtgggtcaat tgtaacgata aa                        402

<210> SEQ ID NO 144
<211> LENGTH: 482
<212> TYPE: DNA
<213> ORGANISM: Oryza sativa

<400> SEQUENCE: 144
aggcagcagc agtatccaac tagtcatgta ccagcctaa attgaaaagt cagatcatgt       60
gtaacatggc cctcaatatt tcgatgttgc cttgtggaaa aaatagctgg tattggtact     120 gtgttttta ctccttccag ctaccgacgt tcagtgttag tgcacaaaat gttcatccat      180
ggtagtttgt ctacattgca gtcatgtaaa gttaaacatt cacgatttct gtacttttgc     240
atgtgtaact aaatgaaatg gtgtgttaca ttcattcctt caatcaaata atccatagaa     300
acaaactggt ttgtaactat tgtaactagt cgctagtgtc catggtattt tcgattgtgg     360
aacataatta gtttaatctg cttcagtata acttaagccg gctttatcct gtgtatgcat     420
cagcttcgct ccattgaaca tccaaacatc agtataagca ttttgtggcg actaatcatc     480
``` cg                                                                      482

<210> SEQ ID NO 145
<211> LENGTH: 396
<212> TYPE: DNA
<213> ORGANISM: Oryza sativa

<400> SEQUENCE: 145
gagtgaggtc taggttctgt tgtctgtctg tccatcatcc atgtgttgac tgttgaggga      60
actcgtttct tcttttcttc acgagatgag ttttttgtgtg cctgtaatac tagtttgtag    120
caaaggctgc gttacataag gtgatgagaa ttgaggtaaa atgagatctg tacactaaat    180
tcattcagac tgttttggca taaagaataa tttggccttc tgcgatttca gaagctataa    240
attgccatct cactaaattc tccttggtcc tcatggcaat gcaacgacag tgtgaagcac    300
tgaagcccgt aatgctctat caccaccatg tacaacagaa ccatatatgt ccatatgtac    360
aactcgagtg ttgtttgagt ggccagcaaa ctggct                              396

<210> SEQ ID NO 146
<211> LENGTH: 415
<212> TYPE: DNA
<213> ORGANISM: Oryza sativa

<400> SEQUENCE: 146
ggtgacggcg acgcgatcga acaggtggtg atcgatgctg caacgtgtgt aaatatacag      60
cgccggctgg gtcaagagat ggctcgggtg acgcgcgcgc ggcgtgtcct ggcgttggcg    120
ccggggcatt ctttagtttt tcatcttttc atcatctcag atggtagata caaaacagtg    180
tatgtatgta gctctgtttc tctctataga accccaacaa attttgttgt tgatgttgtt    240
tatcttcata tgctttgatc ttgaaatcgt ctaccttact actgccgatc gttgctcaaa    300
agtgtggaag tttgaagcat cttccacggg cgttgctcta ctcccatctc gtttcaccac    360
gaaatcccct tcgcatagag gcatctcagc cgtacatctc caaacccacg ttctg         415

<210> SEQ ID NO 147
<211> LENGTH: 290
<212> TYPE: DNA
<213> ORGANISM: Oryza sativa

<400> SEQUENCE: 147
ccgtggcaat ggctgtcatg cttttggcaca tactaatagc aaggtagaat ggtacagcta    60
tttcattatt tttgcccttg tatatttgta tcactcatg agtaaacgac gtttagttat    120
cgatagtttt gttatgagtg atgaatgatc tgcatcgtac tgccaatgcc ttgcattctc    180
aaatggttgc acacttgcac tcatacaaag ttagtacact ccatcatatt ataaattact    240
tttttttcaa gttaaatttc ctgaaagttt gataaaattt atagaaaaaa               290

<210> SEQ ID NO 148
<211> LENGTH: 443
<212> TYPE: DNA
<213> ORGANISM: Oryza sativa

<400> SEQUENCE: 148
acaccacctg ctgtctgcgc ttgtttgttg ccacggctgc gctacaaaca caagccgtat     60
catctgccga acagctccat cgttagcttc ttttgatgcc ttacatctat cgctggacgt   120
ttatcgtgcg tacttgtccc atacagggat tgtgtttgga tgatttgtag agagggtact   180
gtatggcata agatccttca tattaatgtt ctgtgggtca catatcaact tgctattatt   240

```
gtattcagcg gttctctctc tattttgcct taagctgtgg taccatttta agtccagtgc    300
ttgcttttga ttgcttttct gagctttcca ggacatggaa tcgagcctgt gaatgtcgtc    360
ggccggttta tcctttcgac taataattta aattgtccag tgttggttag aatggagta     420 tcagattctg gcggtttgca tgc                                            443

<210> SEQ ID NO 149
<211> LENGTH: 405
<212> TYPE: DNA
<213> ORGANISM: Oryza sativa

<400> SEQUENCE: 149
gctgaaattt ggttatctgt tatgagcata tctgatttcg ataccactg ttatgaaact     60 gaataaaccg cattcctgta tgctgggaat tttctcgtta gtgtacgctc caatactcgt    120
gccgttttca aagacaagca gtgatatgca aagcaatgct gtgtatcttg tgtgttacat    180
caggagtttt ttttaatggt gatttcgttc atagttttca gacatctgtt tccgtcacac    240
gttcgtggga atgactttt tcatatgaaa tgcgcccatg gctgcgcctg aaataatttt    300
acttgtcccg tttgggatga atgaattctt ttcctgttcg ttgttcagta attcacacag    360
agtcataaac ataccggtgg aaacatgctc acaaagaaag aaaca                   405

<210> SEQ ID NO 150
<211> LENGTH: 431
<212> TYPE: DNA
<213> ORGANISM: Oryza sativa

<400> SEQUENCE: 150
agtgttactt attgttgcta ctatccatat tcgctaccat gcttatcatc gctagattaa    60
aggacatgta ttccagtatg gtcgtgcttt ttgcttggta ctctggtcac atttgtgatg    120
aatgttcgca gttttcgtgg tcatggtctg gattctacat tccacctaaa gaagttttta    180
cctggttatt taatccttga gttgttgaat tagctcatgg taattgtcag tagtcttcca    240
cttggtctct ctgtggatg atcgttcttg ttctctgttt gcgctgtggc tgattgttct     300 catgtttta aggtttttgg gttagtcact ggtcgcttcg tcactgtgag ccaaaccata    360
tgccggtagt tttcttcttc accatcatcc gtttgatcct gactcgcgga tctcctaatc    420
caacttctct c                                                         431

<210> SEQ ID NO 151
<211> LENGTH: 423
<212> TYPE: DNA
<213> ORGANISM: Oryza sativa

<400> SEQUENCE: 151
ttggcagcct acccactctg gtaggaaaaa tggaaggggc aagaagatac agtcgatgat    60
atttgatgtg ctacatacca attgtaatat ttcattcata tctagagcta gaaggatatt    120
cacttgtatt tcagactctg gttcacggtt taaattgata ttgtggtaga atgctttctt    180
ggatgggtat atagtgtgac tcgttaaaaa tatgacaaaa cggttcagct actctttaca    240
agtggtacgg caaattgtag acccaattgc acttggcggt gagctgcttt gttggagcaa    300
cagggcactg tctgcttgcg tggatgaaaa gctgagtcat ctgaagctag tgaacatttt    360
ttcgctggct cgctgcgtgt gttttttctc tgattgtggc ccggttgatt atgaaaatga    420
cca                                                                  423
```

<210> SEQ ID NO 152
<211> LENGTH: 349
<212> TYPE: DNA
<213> ORGANISM: Oryza sativa

<400> SEQUENCE: 152

| | | | | | |
|---|---|---|---|---|---|
| ggtgttccat | atagatgatc | agatttctat | aaccacatga | gtacaatgta | gagaattcaa | 60 |
| atgttttgta | accacgtgag | ctttgtacgc | tatttgcacc | acagttctcc | ctgtatgttg | 120 |
| ttggctcttt | tacaattaag | aataatgcat | gttgaagtat | gagtcttcct | gtttgcttct | 180 |
| ccttgatgat | gaaacgctgc | tgcatcaact | gattatttt | cagagaataa | acgataaaca | 240 |
| aagcacggtg | aagtatcgtg | taacccacca | taagtggtag | agccgtagag | gtaggactgt | 300 |
| gcatgctgaa | ttgtaattac | catggttagt | tcagcagaat | ttgcaaaaa | | 349 |

<210> SEQ ID NO 153
<211> LENGTH: 380
<212> TYPE: DNA
<213> ORGANISM: Oryza sativa

<400> SEQUENCE: 153

| | | | | | |
|---|---|---|---|---|---|
| aagaaaggaa | aatgagtcct | gcggattctc | ccttggtatg | taaatatgat | ggatgtgtag | 60 |
| ataaataaaa | tccagtttgt | tgttgtgttt | cctgctgtgt | gaggcgttaa | gagaacttct | 120 |
| ggcgtgcttt | gatttggagc | agttaccatg | actgttggac | tggttttgt | atgtattgat | 180 |
| ggacaaagct | agtaagcatt | aatctatgag | ctgcagttgt | tttccttgat | caatgattat | 240 |
| atatcagctg | ctgttgtatt | ggttatagtg | gattctgact | ttctgatacc | atttcagtct | 300 |
| tcaccaaaac | agcaggctca | actacacttc | tcctgccatt | tcatcatcag | aggaaaaagg | 360 |
| gggaactata | ttctccctgc | | | | | 380 |

<210> SEQ ID NO 154
<211> LENGTH: 343
<212> TYPE: DNA
<213> ORGANISM: Oryza sativa

<400> SEQUENCE: 154

| | | | | | |
|---|---|---|---|---|---|
| gcttcactcc | agttccctat | cttggaaact | tttgcatccg | tgcaaatgta | atctctgctc | 60 |
| tcgtgttagc | ttgtacggag | tagtgttctg | attatggcaa | agacgttgat | gtaagcactc | 120 |
| ggcacctctt | tatcgatgtg | gatttttcc | cggttggtat | ttgaccagat | gttcttgttc | 180 |
| aagaatatgc | tacgttacat | tgtaattact | gtgccatgat | gctctagctt | tcagtgagt | 240 |
| ggtcgaatcc | ttccccaact | tcttactaat | atgcgaaatt | tgcattccat | ctcacagcat | 300 |
| cacgtctcta | ctcttcagtt | ggtagaaagc | attgccctat | ctc | | 343 |

<210> SEQ ID NO 155
<211> LENGTH: 380
<212> TYPE: DNA
<213> ORGANISM: Oryza sativa

<400> SEQUENCE: 155

| | | | | | |
|---|---|---|---|---|---|
| aatgctgcta | tccaacaggt | ggagaaattc | ggtgaacagg | gtagggtatt | tcagaaagtt | 60 |
| tttagcatga | gaacactggt | ggaacagagt | ttttgttcat | ctataggctc | tcggcggtta | 120 |
| attccgacca | tctgttatct | aagctatcat | aaatcttgtg | actcatgtct | gttccaacat | 180 |
| atgctataaa | tgaatgactc | gctaaagatc | tacaagattt | tggtgccatt | tccttaccaa | 240 |
| ttcctttgtg | tcgttgcagt | atgctgtagt | gtatcggcgt | tgctgttccc | agactcgagt | 300 |

```
gttgttgtgt tctgtcttct gttgcttggg cttgttatgt atgattgagt ttatagtatt    360
ctctctcgtg tggcttggtc                                                380

<210> SEQ ID NO 156
<211> LENGTH: 466
<212> TYPE: DNA
<213> ORGANISM: Oryza sativa

<400> SEQUENCE: 156
tgacatctta tagtctgcaa cctctcgtgt ctgaattcct atctttatca agtgttattg     60
cttccacgac tataggacag ctttcgtcga aagcttttgc tcatgtgatc tcgaaggatt   120
catctagtct gattttcgt gacttgtatc ggttttattg gattcatcca acatatatca    180
ataaaaaatg agttgtgttt cctttcttcc tagttcagtt aaaattattt ccctcctgcg   240
cttgtgctgt aattgtctgt gtacctgttg tttgtgactg tgttagttcc cttggatatg   300
atttcgtatt tgatatgtac atggagatag cttagcttca ttattggagt atgaagttag   360
tatgacatag tcactctcct ggaaaattga cactgcaaac catattttta ttctgaacca   420
caaatcctag tcagtccgct ggcatatgcc gtccgtttgc tgaatc                  466

<210> SEQ ID NO 157
<211> LENGTH: 482
<212> TYPE: DNA
<213> ORGANISM: Oryza sativa

<400> SEQUENCE: 157
atgaaccagc gtaagtactc aactgctgag atcgcatcct tttggagcat catctatctt    60
gtcaagctta tttgcaaata gctaagccgt ctctctatgt gtggtctgta atattaaccg   120
tgcgtaaacc agtggcaaga agtccctgtc cgtgtcatgg ttatcgagtc tgtctactta   180
ataacgtgtg ataccaggca ttgtgcctgt attttaacag taaaaattgg gtacgttgtt   240
tgtgtttgta tatatattgg agttggttta cctcagctgg atggagtacc ctacattcgc   300
attgtactgc ctacgtttta tattacaagt cattttaact tttttttgaa gttaaacttt   360
tatatgttta atcaagttta tagaaaaaca tagtaatata tttaacacaa aacaaaaaaa   420
aatcaaaata tgtttaatgt tagatgtaat gaaattaatt tagtgttata agcgtcgtta   480
ta                                                                 482

<210> SEQ ID NO 158
<211> LENGTH: 384
<212> TYPE: DNA
<213> ORGANISM: Oryza sativa

<400> SEQUENCE: 158
tacttgtagc aatacaaaat tacagtagca ttgtacacta ctgccgtgcc agctccatgc    60
atagtcagca gctggccact ctctagctat atctagatgc gagagaattt taaggatgta   120
aatcatgcct tcacatgaat aaatcgttcg tccgtgcgtt gtgtattcat gtaaattttg   180
acggatggtc aagtaaaaat aacaatggca aattaattta gggaagaatc aaatatgttt   240
gcgttccttt tctgagccgt ggatgttgtt aatcagttct accaatcgct atttgtaaaa   300
agtttcttaa agaaatttcc ttcttgacat caatcaaagt actatatata aatcttcagg   360
ataaggcacg tcgccgacca aaca                                          384

<210> SEQ ID NO 159
```

<211> LENGTH: 445
<212> TYPE: DNA
<213> ORGANISM: Oryza sativa

<400> SEQUENCE: 159

```
tttgtctctc ggccattgtg tattttcct ctcaagttgt atatgttcgc cccggaggaa      60
aagttttgtt tcttctttcg ctgcctcttt tgtacctgtg gtttccctgg cgtgagagcc     120
agtctgttgc acgcctgatc cctcttttat cgggagaaag gttcaacgtt cgggtgctag    180
atacaaaatg ggttcctaga gcccttcttg gtcgtttata tttagtgtac tattagtgat    240
aattggtgta aattagtttt ccccagtttc ctttttagaa ctcatgtaga ctttcttgca    300
tctgatgtta gtaaaatttt gctctaggtg tgctggctat tcttatcctt agcctgactt    360
catgatgttt ctttctttgt gagcatgttt ccaccggtat gtttatgact ctgtgtgaat    420
tactgaacaa cgaacaggaa aagaa                                           445
```

<210> SEQ ID NO 160
<211> LENGTH: 371
<212> TYPE: DNA
<213> ORGANISM: Oryza sativa

<400> SEQUENCE: 160

```
aggccaaggc gatctgtgac tatgtgatga acaaacagag cccttccagt ctgatggctc      60
atggctgtgt gaccctgtga atccagcatt gtgtgtgcgc gcgcgcgtca tgaattgtca    120
aaaattatgg ctggaaaacc aagtggtttc tggcaatatg tgttgtaccg cttgtatgta    180
aatgttggta aaaacaaagt aacatcgctt atctctgaat ctctaacgta agtggttgct    240
taacaaaagc tgctttgccc cgctgtaagc ctgctacact agcgtggttt cttacatttt    300
tgcctgctat aaattctgtt caatttcaag gggttccaag ctatgtttcc aacgttgggt    360
gagtttggat t                                                          371
```

<210> SEQ ID NO 161
<211> LENGTH: 411
<212> TYPE: DNA
<213> ORGANISM: Oryza sativa

<400> SEQUENCE: 161

```
ttcatttcgt catgcatcat atcaccctaa atatgcatgc gccaataaaa acaagtcttg      60
attttatttt gttcattgct ccatcttcag tcagtgtcca ctggtttgtc tgtcatgcat    120
ggatcatttt tactcttcaa ttcagttctg catttcagtt gagctgttca gctgagtgcc    180
ttgatttgta ccacctatct gccttgttac aaatttatgt caaagtcttc ttgctctggt    240
acagttttac gttttcttct gcaatactag tacgcacagg aagctaagct gacaccttcc    300
aactcttcaa gaaacgaaa gctgcaacaa gtgtagcacg attcacgacc ccgagcatga    360
gctaggttag gcaaaacaaa caaatcagca gggtcggatg actttactta c             411
```

<210> SEQ ID NO 162
<211> LENGTH: 519
<212> TYPE: DNA
<213> ORGANISM: Oryza sativa

<400> SEQUENCE: 162

```
tgaaatcaat actgttggct ggtgtttgca tagagaaaca atcacaatta cttagtgagt      60
cacatcctaa attctaacta gaacggcaca tgcccgaaat tttgactgca aattgctttg    120
ttggattgtg ttacacggct tcagagcggt tgccaaaagt tcatttagaa gaaaggctgt    180
```

```
cagaagttat cctataaatt taaaaatagt gcgcttccaa accaagcgcc tttttcagtt      240
gttcggtaca tcaaatatgt attgtatacc ttggaggctt ggaatataaa tatgggcacg      300
ctagtgctac agccatttgc tactgatgta ccagcaacca ttggtttgta ccttgattaa      360
ttcatgacga tggtctaatt ctgttgtcct cttttttgcaa attctgctga actaaccatg    420
gtaattacaa ttcagcatgc acagtcctac ctctacggct ctaccactta tggtgggtta    480
cacgatactt caccgtgctt tgtttatcgt ttattctct                            519
```

PLANT TERMINATOR SEQUENCES

CROSS REFERENCE TO RELATED APPLICATIONS

This application claims priority to U.S. application Ser. No. 16/032,228, filed on Jul. 11, 2018, now U.S. Patent No. 11, 248, 233, issued Feb. 15, 2022, which claims priority to U.S. application Ser. No. 14/129,551, filed on Dec. 27, 2013, now U.S. Pat. No. 10,059,953, issued Aug. 28, 2018, which is a 371 (National Stage) of PCT/US2012/046686, filed on Jul. 13, 2012, which claims the benefit of Indian Provisional Application No. 2001/DEL/2011, filed Jul. 15, 2011, and U.S. Provisional Application No. 61/557,433, filed Nov. 9, 2011, the entire contents of each is herein incorporated by reference.

FIELD OF INVENTION

The present invention relates to the field of plant molecular biology and plant genetic engineering. More specifically, it relates to novel plant terminator sequences and their use to regulate gene expression in plants.

BACKGROUND

Recent advances in plant genetic engineering have opened new doors to engineer plants to have improved characteristics or traits. These transgenic plants characteristically have recombinant DNA constructs in their genome that have a protein-coding region operably linked to multiple regulatory regions that allow accurate expression of the transgene. A few examples of regulatory elements that help regulate gene expression in transgenic plants are promoters, introns, terminators, enhancers and silencers.

Plant genetic engineering has advanced to introducing multiple traits into commercially important plants, also known as gene stacking. This can be accomplished by multigene transformation, where multiple genes are transferred to create a transgenic plant that might express a complex phenotype, or multiple phenotypes. But it is important to modulate or control the expression of each transgene optimally. The regulatory elements need to be diverse, to avoid introducing into the same transgenic plant repetitive sequences, which have been correlated with undesirable negative effects on transgene expression and stability (Peremarti et al (2010) *Plant Mol Biol* 73:363-378; Mette et al (1999) EMBO J 18:241-248; Mette et al (2000) EMBO J 19:5194-5201; Mourrain et al (2007) Planta 225:365-379, U.S. Pat. Nos. 7,632,982, 7,491,813, 7,674,950, PCT Application No. PCT/US2009/046968). Therefore it is important to discover and characterize novel regulatory elements that can be used to express heterologous nucleic acids in important crop species. Diverse regulatory regions can be used to control the expression of each transgene optimally.

Regulatory sequences located downstream of protein-coding regions contain signals required for transcription termination and 3' mRNA processing, and are called terminator sequences. The terminator sequences play a key role in mRNA processing, localization, stability and translation (Proudfoot, N, (2004) *Curr Opin Cell Biol* 16272-278; Gilmartin, G. M. (2005) *Genes Dev.* 19:2517-2521). The 3' regulatory sequences contained in terminator sequences can affect the level of expression of a gene. Optimal expression of a chimeric gene in plant cells has been found to be dependent on the presence of appropriate 3' sequences (Ingelbrecht et al. (1989) *Plant Cell* 1:671-680). Read-through transcription through a leaky terminator of a gene can cause unwanted transcription of one transgene from the promoter of another one. Also, bidirectional, convergent transcription of transgenes in transgenic plants that have leaky transcription termination of the convergent genes can lead to overlapping transcription of the convergent genes. Convergent, overlapping transcription can decrease transgene expression, or generate antisense RNA (Bieri, S. et al (2002) *Molecular Breeding* 10:107-117). This underlines the importance of discovering novel and efficient transcriptional terminators.

SUMMARY

Regulatory sequences for modulating gene expression in plants are described. Specifically, regulatory sequences that are transcription terminator sequences are described. Recombinant DNA constructs comprising terminator sequences are provided.

One embodiment is a recombinant construct comprising an isolated polynucleotide comprising (a) a nucleotide sequence as set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (b) a nucleotide sequence with at least 95% sequence identity to the sequence set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (c) a functional fragment of either (a) or (b); wherein the isolated polynucleotide functions as a transcriptional terminator in a plant cell. In another embodiment, the isolated polynucleotide is operably linked to the 3' end of a heterologous polynucleotide which is operably linked to a promoter.

One embodiment is a recombinant construct comprising an isolated polynucleotide comprising (a) a nucleotide sequence as set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (b) a nucleotide sequence with at least 95% sequence identity to the sequence set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (c) a functional fragment of either (a) or (b); wherein the isolated polynucleotide functions as a bidirectional transcriptional terminator in a plant cell. Another embodiment is the recombinant construct wherein the bidirectional transcriptional terminator is operably linked to (a) the 3' end of a first heterologous polynucleotide which is operably linked to a first promoter; and (b) the 3' end of a second heterologous polynucleotide which is operably linked to a second promoter; wherein the first and the second heterologous polynucleotides are transcribed in a convergent manner.

One embodiment is a method of expressing a heterologous polynucleotide in a plant, comprising the steps of (a) introducing into a regenerable plant cell a recombinant construct wherein the recombinant construct comprises an isolated polynucleotide comprising (i) a nucleotide sequence as set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (ii) a nucleotide sequence with at least 95% sequence identity to the sequence set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (iii) a functional fragment of either (i) or (ii); wherein the isolated polynucleotide functions as a transcriptional terminator in a plant cell and further wherein the isolated polynucleotide is operably linked to the 3' end of a heterologous polynucleotide which is operably linked to a promoter; (b) regenerating a transgenic plant from the regenerable plant cell of (a), wherein the transgenic plant comprises in its genome the recombinant construct; and (c) obtaining a progeny plant from the transgenic plant of step (b), wherein the progeny plant comprises in its genome the recombinant DNA construct and exhibits expression of the heterologous polynucleotide.

Another embodiment provides for a method of regulating the expression of two heterologous polynucleotides in a plant, comprising the steps of: (a) introducing into a regenerable plant cell a recombinant construct, wherein the recombinant construct comprises an isolated polynucleotide comprising (i) a nucleotide sequence as set forth in SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (ii) a nucleotide sequence with at least 95% sequence identity to the sequence set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (iii) a functional fragment of either (i) or (ii); wherein the isolated polynucleotide functions as a bidirectional transcriptional terminator in a plant cell and further wherein the bidirectional transcriptional terminator is operably linked to the 3' end of a first heterologous polynucleotide which is operably linked to a first promoter and the 3' end of a second heterologous polynucleotide which is operably linked to a second promoter; wherein the first and the second heterologous polynucleotides are transcribed in a convergent manner; (b) regenerating a transgenic plant from the regenerable plant cell of (a), wherein the transgenic plant comprises in its genome the recombinant construct; and (c) obtaining a progeny plant from the transgenic plant of step (b), wherein the progeny plant comprises in its genome the recombinant DNA construct and exhibits expression of both the first heterologous polynucleotide and the second heterologous polynucleotide.

Another embodiment is a vector, cell, microorganism, plant, or seed comprising a recombinant DNA construct comprising a terminator sequences described herein.

Another embodiment is a regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the terminator sequences described herein is selected from the group consisting of: Arabidopsis, maize, soybean, sunflower, sorghum, canola, mustard, wheat, alfalfa, cotton, rice, barley, millet, sugar cane and switchgrass.

In one embodiment, the plant comprising the terminator sequences described herein is a monocotyledenous plant. In another embodiment, the plant comprising the terminator sequences described herein is a rice plant.

BRIEF DESCRIPTION OF THE DRAWINGS AND SEQUENCE LISTING

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

FIG. 1 is a schematic representation of the binary plant transformation vector, the Terminator Test Vector (TTV; PHP49597) used for testing terminators carrying the GUS reporter gene driven by the Maize Ubiquitin promoter. GUSINT is the β-glucuronidase gene with an intron inserted at SnaBI site to prevent bacterial expression. The Acc65I site used for cloning of putative terminator sequences to be tested is also shown.

Figure 1:
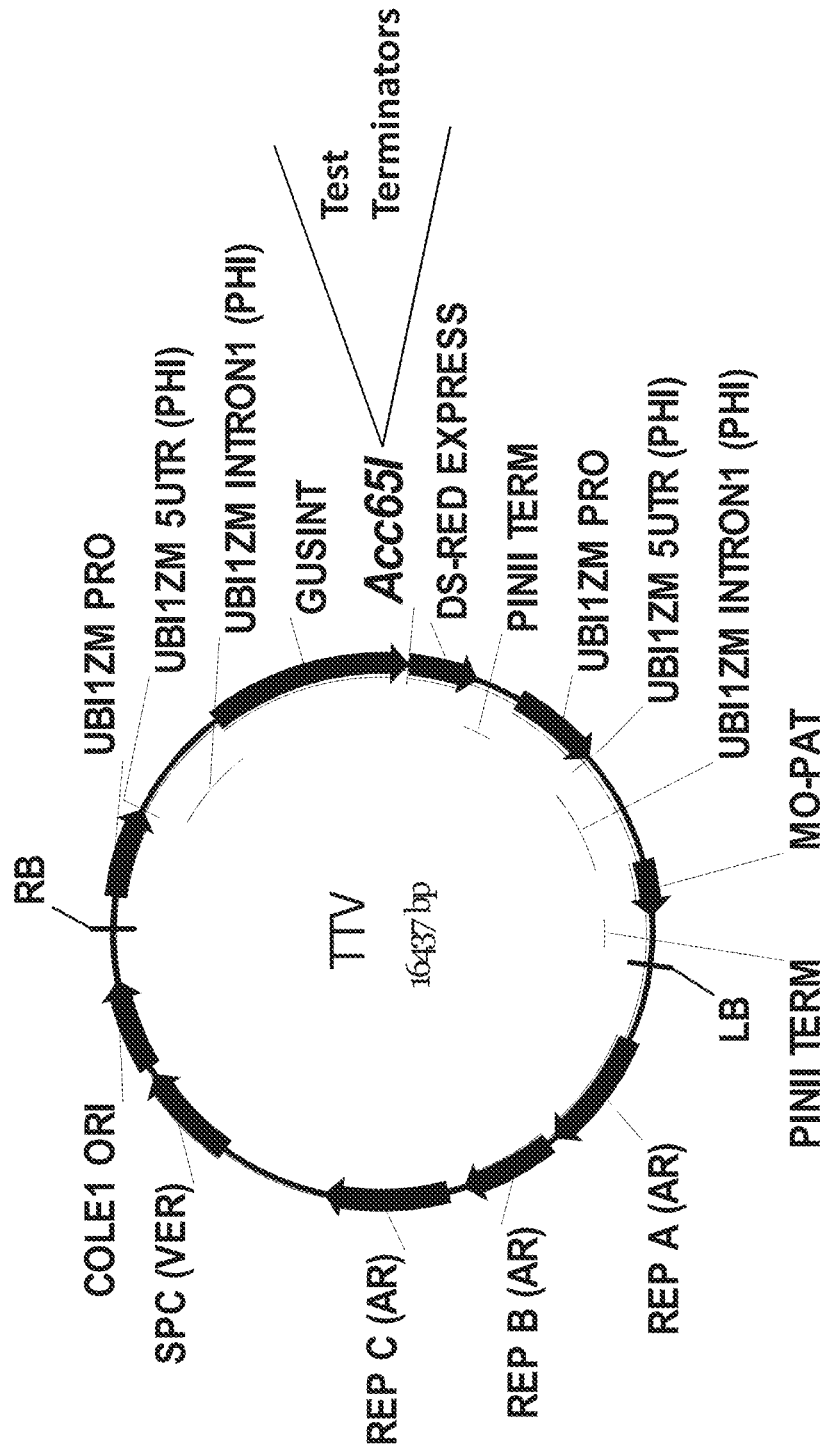

SEQ ID NO:1 is the sequence of the terminator test vector (TTV; PHP49597) carrying GUS (β-glucuronidase) reporter gene driven by the maize ubiquitin promoter.

SEQ ID NO:2-35 are the sequences of the candidate terminator sequences from Arabidopsis thaliana and Oryza sativa, as given in Table 1.

TABLE 1

| SEQ ID NO | Name | Species |
|---|---|---|
| 2 | T1 | Arabidopsis thaliana |
| 3 | T2 | Arabidopsis thaliana |
| 4 | T3 | Arabidopsis thaliana |
| 5 | T4 | Arabidopsis thaliana |
| 6 | T5 | Arabidopsis thaliana |
| 7 | T6 | Arabidopsis thaliana |
| 8 | T7 | Arabidopsis thaliana |
| 9 | T8 | Arabidopsis thaliana |
| 10 | T9 | Arabidopsis thaliana |
| 11 | T10 | Arabidopsis thaliana |
| 12 | T11 | Arabidopsis thaliana |
| 13 | T12 | Arabidopsis thaliana |
| 14 | T13 | Arabidopsis thaliana |
| 15 | T14 | Arabidopsis thaliana |
| 16 | T15 | Oryza sativa |
| 17 | T16 | Oryza sativa |
| 18 | T17 | Oryza sativa |
| 19 | T18 | Oryza sativa |
| 20 | T19 | Oryza sativa |
| 21 | T20 | Oryza sativa |
| 22 | T21 | Oryza sativa |
| 23 | T22 | Oryza sativa |
| 24 | T23 | Oryza sativa |
| 25 | T24 | Oryza sativa |
| 26 | T25 | Oryza sativa |
| 27 | T26 | Oryza sativa |
| 28 | T27 | Oryza sativa |
| 29 | T28 | Oryza sativa |
| 30 | T29 | Oryza sativa |
| 31 | T30 | Oryza sativa |
| 32 | T31 | Oryza sativa |
| 33 | T32 | Oryza sativa |
| 34 | T33 | Oryza sativa |
| 35 | T34 | Oryza sativa |

SEQ ID NO:36 is the sequence of the PINII terminator.
SEQ ID NOS:37-106 are the primers used for amplifying the candidate terminator sequences and the PINII terminator sequence, as given in Table 2.

SEQ ID NOS:107-113 are the primer sequences used for RT-PCR to determine read through transcription for the candidate terminator sequences.

SEQ ID NOS:114-125 are the sequences of the probes and primers used for qRT-PCR (quantitative reverse transcriptase PCR) for testing the candidate terminator sequences, as given in Table 4.

SEQ ID NOS:126-128 are the sequences of the primers used for polyA mapping.

SEQ ID NOS:129-162 are the sequences of the shorter terminator sequences.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein. A monocot includes the *Gramineae*.

The terms "dicot" and "dicotyledonous plant" are used interchangeably herein. A dicot includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Propagule" includes all products of meiosis and mitosis able to propagate a new plant, including but not limited to, seeds, spores and parts of a plant that serve as a means of vegetative reproduction, such as corms, tubers, offsets, or runners. Propagule also includes grafts where one portion of a plant is grafted to another portion of a different plant (even one of a different species) to create a living organism. Propagule also includes all plants and seeds produced by cloning or by bringing together meiotic products, or allowing meiotic products to come together to form an embryo or fertilized egg (naturally or with human intervention).

"Progeny" comprises any subsequent generation of a plant.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to the portion of a messenger RNA (or the corresponding portion of another nucleic acid molecule such as a DNA molecule) which encodes a protein or polypeptide. "Non-coding region" refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein.

The terms "entry clone" and "entry vector" are used interchangeably herein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

Promoters that cause a gene to be expressed in most cell types at most times are commonly referred to as "constitutive promoters".

Inducible promoters selectively express an operably linked DNA sequence in response to the presence of an endogenous or exogenous stimulus, for example by chemical compounds (chemical inducers) or in response to environmental, hormonal, chemical, and/or developmental signals. Examples of inducible or regulated promoters include, but are not limited to, promoters regulated by light, heat, stress, flooding or drought, pathogens, phytohormones, wounding, or chemicals such as ethanol, jasmonate, salicylic acid, or safeners.

"Enhancer sequences" refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

"Transcription terminator", "termination sequences", or "terminator" refer to DNA sequences located downstream of a protein-coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., *Plant Cell* 1:671-680 (1989). A polynucleotide sequence with "terminator activity" refers to a polynucleotide sequence that, when operably linked to the 3' end of a second polynucleotide sequence that is to be expressed, is capable of terminating transcription from the second polynucleotide sequence and facilitating efficient 3' end processing of the messenger RNA resulting in addition of poly A tail. Transcription termination is the process by which RNA synthesis by RNA polymerase is stopped and both the processed messenger RNA and the enzyme are released from the DNA template.

Improper termination of an RNA transcript can affect the stability of the RNA, and hence can affect protein expression. Variability of transgene expression is sometimes attributed to variability of termination efficiency (Bieri et al (2002) *Molecular Breeding* 10: 107-117). As used herein, the terms "bidirectional transcriptional terminator" and "bidirectional terminator" refer to a transcription terminator sequence that has the capability of terminating transcription in both 5' to 3', and 3' to 5' orientations. A single sequence element that acts as a bidirectional transcriptional terminator can terminate transcription initiated from two convergent promoters.

The present invention encompasses functional fragments and variants of the terminator sequences disclosed herein.

A "functional fragment" herein is defined as any subset of contiguous nucleotides of the terminator sequence disclosed herein, that can perform the same, or substantially similar function as the full length promoter sequence disclosed herein. A "functional fragment" with substantially similar function to the full length terminator disclosed herein refers to a functional fragment that retains the ability to terminate transcription largely to the same level as the full-length terminator sequence. A recombinant construct comprising a heterologous polynucleotide operably linked to a "functional fragment" of the terminator sequence disclosed herein exhibits levels of heterologous polynucleotide expression substantially similar to a recombinant construct comprising a heterologous polynucleotide operably linked to the full-length terminator sequence.

A "variant", as used herein, is the sequence of the terminator or the sequence of a functional fragment of a terminator containing changes in which one or more nucleotides of the original sequence is deleted, added, and/or substituted, while substantially maintaining terminator function. One or more base pairs can be inserted, deleted, or substituted internally to a terminator, without affecting its activity. Fragments and variants can be obtained via methods such as site-directed mutagenesis and synthetic construction.

These terminator functional fragments may comprise at least 50 contiguous nucleotides, at least 75 contiguous nucleotides, at least 100 contiguous nucleotides, at least 150 contiguous nucleotides, at least 200 contiguous nucleotides, at least 250 contiguous nucleotides, at least 300 contiguous nucleotides, at least 350 contiguous nucleotides, at least 400 contiguous nucleotides, at least 450 contiguous nucleotides, at least 500 contiguous nucleotides, at least 550 contiguous nucleotides, at least 600 contiguous nucleotides, at least 650 contiguous nucleotides, at least 700 contiguous nucleotides, at least 750 contiguous nucleotides or at least 800 contiguous nucleotides of the particular terminator nucleotide sequence disclosed herein. Such fragments may be obtained by use of restriction enzymes to cleave the naturally occurring terminator nucleotide sequences disclosed herein; by synthesizing a nucleotide sequence from the naturally occurring terminator DNA sequence; or may be obtained through the use of PCR technology. See particularly, Mullis et al., *Methods Enzymol.* 155:335-350 (1987), and Higuchi, R. In PCR Technology: Principles and Applications for DNA Amplifications; Erlich, H. A., Ed.; Stockton Press Inc.: New York, 1989. Again, variants of these terminator fragments, such as those resulting from site-directed mutagenesis, are encompassed by the compositions of the present invention.

The terms "substantially similar" and "corresponding substantially" as used herein refer to nucleic acid fragments, particularly terminator sequences, wherein changes in one or more nucleotide bases do not substantially alter the ability of the terminator to terminate transcription. These terms also refer to modifications, including deletions and variants, of the nucleic acid sequences of the instant invention by way of deletion or insertion of one or more nucleotides that do not substantially alter the functional properties of the resulting terminator relative to the initial, unmodified terminator. It is therefore understood, as those skilled in the art will appreciate, that the invention encompasses more than the specific exemplary sequences.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, WI). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, *CABIOS.* 5:151-153 (1989); Higgins, D. G. et al., *Comput. Appl. Biosci.* 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

As will be evident to one of skill in the art, any heterologous polynucleotide of interest can be operably linked to the terminator sequences described in the current invention. Examples of polynucleotides of interest that can be operably linked to the terminator sequences described in this invention include, but are not limited to, polynucleotides comprising regulatory elements such as introns, enhancers, promoters, translation leader sequences, protein-coding regions from disease and insect resistance genes, genes conferring nutritional value, genes conferring yield and heterosis increase, genes that confer male and/or female sterility, antifungal, antibacterial or antiviral genes, selectable marker genes, herbicide resistance genes and the like. Likewise, the terminator sequences described in the current invention can be used to terminate transcription of any nucleic acid that controls gene expression. Examples of nucleic acids that could be used to control gene expression include, but are not limited to, antisense oligonucleotides, suppression DNA constructs, or nucleic acids encoding transcription factors.

A recombinant DNA construct (including a suppression DNA construct) of the present invention may comprise at least one regulatory sequence. In an embodiment of the present invention, the regulatory sequences disclosed herein can be operably linked to any other regulatory sequence.

Embodiments Include the Following

One embodiment is a polynucleotide comprising: (i) a nucleic acid sequence of at least 90%, 91%, 92%, 93%, 94%, 95%, 96%, 97%, 98%, 99%, or 100% sequence identity, based on the Clustal V method of alignment, when compared to SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (ii) a nucleic acid sequence of at least 90%, 91%, 92%, 93%, 94%, 95%, 96%, 97%, 98%, 99% or 100% sequence identity, based on the Clustal V method of alignment, when compared to a functional fragment of SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (iii) a full complement of the nucleic acid sequence of (i) or (ii), wherein the polynucleotide acts as a terminator in a plant cell.

One embodiment is an isolated polynucleotide comprising a nucleotide sequence, wherein the nucleotide sequence corresponds to an allele of a terminator described herein.

Recombinant DNA constructs comprising terminator sequences are also provided.

One embodiment is a recombinant construct comprising an isolated polynucleotide comprising (a) a nucleotide sequence as set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (b) a nucleotide sequence with at least 95% sequence identity to the sequence set forth in SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (c) a functional fragment of either (a) or (b); wherein the isolated polynucleotide functions as a transcriptional terminator in a plant cell. In another embodiment, the isolated polynucleotide is operably linked to the 3' end of a heterologous polynucleotide which is operably linked to a promoter.

One embodiment is a recombinant construct comprising an isolated polynucleotide comprising (a) a nucleotide sequence as set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (b) a nucleotide sequence with at least 95% sequence identity to the sequence set forth in SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; (c) a functional fragment of either (a) or (b); wherein the isolated polynucleotide functions as a bidirectional transcriptional terminator in a plant cell. Another embodiment of the current invention is the recombinant construct wherein the bidirectional transcriptional terminator is operably linked to (a) the 3' end of a first heterologous polynucleotide which is operably linked to a first promoter; and (b) the 3' end of a second heterologous polynucleotide which is operably linked to a second promoter; wherein the first and the second heterologous polynucleotides are transcribed in a convergent manner.

One embodiment is a method of expressing a heterologous polynucleotide in a plant, comprising the steps of (a) introducing into a regenerable plant cell a recombinant construct wherein the recombinant construct comprises an isolated polynucleotide comprising (i) a nucleotide sequence as set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (ii) a nucleotide sequence with at least 95% sequence identity to the sequence set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (iii) a functional fragment of either (i) or (ii); wherein the isolated polynucleotide functions as a transcriptional terminator in a plant cell and further wherein the isolated polynucleotide is operably linked to the 3' end of a heterologous polynucleotide which is operably linked to a promoter; (b) regenerating a transgenic plant from the regenerable plant cell of (a), wherein the transgenic plant comprises in its genome the recombinant DNA construct and exhibits expression of the heterologous polynucleotide.

One embodiment is a method of expressing a heterologous polynucleotide in a plant, comprising the steps of (a) introducing into a regenerable plant cell a recombinant construct wherein the recombinant construct comprises an isolated polynucleotide comprising (i) a nucleotide sequence as set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (ii) a nucleotide sequence with at least 95% sequence identity to the sequence set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (iii) a functional fragment of either (i) or (ii); wherein the isolated polynucleotide functions as a transcriptional terminator in a plant cell and further wherein the isolated polynucleotide is operably linked to the 3' end of a heterologous polynucleotide which is operably linked to a promoter; (b) regenerating a transgenic plant from the regenerable plant cell of (a), wherein the transgenic plant comprises in its genome the recombinant construct; and (c) obtaining a progeny plant from the transgenic plant of step (b), wherein the progeny plant comprises in its genome the recombinant DNA construct and exhibits expression of the heterologous polynucleotide.

Another embodiment provides for a method of regulating the expression of two heterologous polynucleotides in a plant, comprising the steps of: (a) introducing into a regenerable plant cell a recombinant construct, wherein the recombinant construct comprises an isolated polynucleotide comprising (i) a nucleotide sequence as set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (ii) a nucleotide sequence with at least 95% sequence identity to the sequence set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (iii) a functional fragment of either (i) or (ii); wherein the isolated polynucleotide functions as a bidirectional transcriptional terminator in a plant cell and further wherein the bidirectional transcriptional terminator is operably linked to the 3' end of a first heterologous polynucleotide which is operably linked to a first promoter and the 3' end of a second heterologous polynucleotide which is operably linked to a second promoter; wherein the first and the second heterologous polynucleotides are transcribed in a convergent manner; (b) regenerating a transgenic plant from the regenerable plant cell of (a), wherein the transgenic plant comprises in its genome the recombinant DNA construct and exhibits expression of both the first heterologous polynucleotide and the second heterologous polynucleotide.

Another embodiment provides for a method of regulating the expression of two heterologous polynucleotides in a plant, comprising the steps of: (a) introducing into a regenerable plant cell a recombinant construct, wherein the recombinant construct comprises an isolated polynucleotide comprising (i) a nucleotide sequence as set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (ii) a nucleotide sequence with at least 95% sequence identity to the sequence set forth in SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 129-161 or 162; or (iii) a functional fragment of either (i) or (ii); wherein the isolated polynucleotide functions as a bidirectional transcriptional terminator in a plant cell and further wherein the bidirectional transcriptional terminator is operably linked to the 3' end of a first heterologous polynucleotide which is operably linked to a first promoter and the 3' end of a second heterologous polynucleotide which is operably linked to a second promoter; wherein the first and the second heterologous polynucleotides are transcribed in a convergent manner; (b) regenerating a transgenic plant from the regenerable plant cell of (a), wherein the transgenic plant comprises in its genome the recombinant DNA construct; and (c) obtaining a progeny plant from the transgenic plant of step (b), wherein the progeny plant comprises in its genome the recombinant DNA construct and exhibits expression of both the first heterologous polynucleotide and the second heterologous polynucleotide.

Another embodiment is a vector, cell, microorganism, plant, or seed comprising a recombinant DNA construct comprising a terminator sequence described herein.

Another embodiment encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the terminator sequences described in the present invention is selected from the group consisting of: *Arabidopsis*, maize, soybean, sunflower, sorghum, canola, mustard, wheat, alfalfa, cotton, rice, barley, millet, sugar cane and switchgrass.

In one embodiment, the plant comprising the terminator sequences described in the present invention is a monocotyledenous plant. In another embodiment, the plant comprising the terminator sequences described in the present invention is a rice plant.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Identification of Novel Terminator Sequences

The computational strategy to identify convergent gene pairs with high co-expression frequency involved the following steps:
Analysis of *Arabidopsis* and rice genomes for identification of convergent gene pairs.
Analysis of their transcriptomes for identification of convergent genes with high expression.
Identification of samples in which both genes from a convergent pair showed high expression.
Identification of Candidate *Arabidopsis* Terminators:
For identification of convergent gene pairs, the *Arabidopsis* genome GFF (General File Format) file was analyzed to identify adjacent gene models in the convergent orientation with an intergenic distance ranging from 20 bp-1000 bp between them. A total of 3535 convergent gene pairs were identified and their nucleotide sequences were then retrieved. For the transcriptomics analysis, publicly available Affymetrix® array data from the Nottingham *Arabidopsis* Stock Center (NASC's international Affymetrix® service) were downloaded along with their metadata including sample annotations. Samples were scaled to a mean signal value of 100 and those with poor quality and no metadata were discarded. Finally, 3000 samples were selected for this analysis. For each gene in the shortlisted convergent gene pairs, probes on the Affymetrix® array were identified and only those probes that uniquely mapped to the selected genes were selected for further analysis. Z-scores for each of the samples were calculated using median-centering; if the z-score of a probe in a given sample was greater than two, it was considered as having high expression in that sample. Finally gene pairs were shortlisted based on the criteria that both members of the gene pairs showed high expression in at least one sample. From this analysis, 89 such pairs were identified and they were further shortlisted to 24 gene pairs that showed high co-expression in at least 10 samples. Gene annotation and tissue level expression pattern were also included as additional data for the selected gene pairs. The *Arabidopsis* transcriptome tiling array (Salk Institute Genomic Analysis Laboratory; Yamada et al., 2003, Science, 302 (5646): 842-846) was used to independently evaluate the co-expression data of the 24 gene pairs. Based on a combination of the number of common samples in which a gene pair was showing co-expression and correlation between the expression analyses and the tiling array, 7 gene pairs were finally selected for experimental analysis. The nucleotide sequence between stop codons of each gene pair including the 3'UTRs of both genes and the intergenic region was identified and cloned for testing.
Identification of Candidate Rice Terminators:
A similar approach was used for identifying novel terminators from rice. The entire rice genome was obtained from the MSU Rice Genome Annotation Project Database and was analyzed to identify 2892 convergent gene pairs with an intergenic distance range of 20-1000 bp. Public Affymetrix® microarray data was downloaded from the NCBI expression repository, Gene Expression Omnibus, and good quality samples were selected for analysis. For calculating high expression, the $95^{th}$ percentile value of signal intensity in each sample was calculated, i.e. only 5% of the genes on the entire chip exhibited signal intensity values greater than this threshold for the given sample. For each gene pair the samples in which both genes were above the 95th percentile were identified. From this analysis, 82 gene pairs were identified as showing high co-expression in at least one sample; of these, 34 gene pairs showed high co-expression in at least 10 samples and were shortlisted for further experimental analysis. Out of these, the top 10 candidate pairs based on the number of samples in which the gene pairs showed co-expression and presence of a valid gene model were selected for testing. The nucleotide sequence between stop codons of each gene pair including the 3'UTRs of both genes and the intergenic region was identified and used for testing as transcription terminators in plant cells.

Example 2

Amplification and Cloning of *Arabidopsis* and Rice Terminator Sequences

We constructed a terminator test vector (TTV) (PHP49597; FIG. 1; SEQ ID NO:1) carrying GUS (β-glucuronidase) reporter gene driven by the maize ubiquitin promoter using standard molecular biology techniques (Sambrook et al.). A promoterless Ds-RED coding sequence was included downstream of the GUS gene for measurement of read-through transcription. The Ds-Red sequence was followed by a PinII terminator to enable termination and polyadenlylation of all read-through transcripts, so we could detect them by reverse-transcription-PCR (RT-PCR) using oligo-dT primer. The Terminator test vector also carried a monocot-optimized phosphinothricin acetyltransferase (MOPAT) gene as a plant selectable marker.

Genomic DNA was isolated from *Arabidopsis thaliana* and *Oryza sativa* leaf tissue using the QIAGEN® DNEASY® Plant Maxi Kit (QIAGEN Inc.) according to the manufacturer's instructions. Candidate terminator sequences were amplified from genomic DNA with PHUSION® DNA polymerase (New England Biolabs Inc.), using the primer sequences listed in Table 2. T1 to T14 sequences (SEQ ID NOS:2-15) were amplified from *Arabidopsis thaliana* and T15 to T34 (SEQ ID NOS:16-35) were amplified from *Oryza sativa* L. var. Nipponbare. T1 to T7 (SEQ ID NOS:2-8) are complementary to sequences T8 to T14 (SEQ ID NOS:9-15) and T15 to T24 (SEQ ID NOS: 16-25) are complementary to T25 to T34 (SEQ ID NOS: 26-35) (Table 3). The resulting DNA fragments were cloned into the terminator test vector at Acc65I restriction site using In-FUSION™ cloning (Clontech Inc.) and sequenced completely. As a positive control we cloned the potato PINII terminator (SEQ ID NO:36; Keil et al. (1986) *Nucleic Acids Res.* 14:5641-5650) at the same location as the test terminators to produce the plasmid PHP49598.

All constructs were transformed into *Agrobacterium* (LBA4404/pSB1) and selected on spectinomycin and tetracycline. Integrity of the plasmids in *Agrobacterium* was confirmed by restriction digestion analysis from retransformed *E. coli*.

TABLE 2

| Primer ID | Terminator | Amplicon Size (bp) | Construct |
|---|---|---|---|
| TETO-1028 F (SEQ ID NO: 37) | T1 | 557 | PHP49622 |
| TETO-1029 R (SEQ ID NO: 38) | (SEQ ID NO: 2) | | |
| TETO-1207 F (SEQ ID NO: 39) | T2 | 573 | PHP51066 |
| TETO-1208 R (SEQ ID NO: 40) | (SEQ ID NO: 3) | | |
| TETO-1209 F (SEQ ID NO: 41) | T3 | 633 | PHP51067 |
| TETO-1210 R (SEQ ID NO: 42) | (SEQ ID NO: 4) | | |
| TETO-1211 F (SEQ ID NO: 43) | T4 | 639 | PHP51068 |
| TETO-1212 R (SEQ ID NO: 44) | (SEQ ID NO: 5) | | |
| TETO-1213 F (SEQ ID NO: 45) | T5 | 685 | PHP51069 |
| TETO-1214 R (SEQ ID NO: 46) | (SEQ ID NO: 6) | | |
| TETO-1215 F (SEQ ID NO: 47) | T6 | 411 | PHP51070 |
| TETO-1216 R (SEQ ID NO: 48) | (SEQ ID NO: T7) | | |
| TETO-1030 F (SEQ ID NO: 49) | T7 | 457 | PHP49623 |
| TETO-1031 R (SEQ ID NO: 50) | (SEQ ID NO: 8) | | |
| TETO-1032 F (SEQ ID NO: 51) | T8 | 557 | PHP49624 |
| TETO-1033 R (SEQ ID NO: 52) | (SEQ ID NO: 9) | | |
| TETO-1034 F (SEQ ID NO: 53) | T9 | 573 | PHP49625 |
| TETO-1035 R (SEQ ID NO: 54) | (SEQ ID NO: 10) | | |
| TETO-1217 F (SEQ ID NO: 55) | T10 | 633 | PHP51071 |
| TETO-1218 R (SEQ ID NO: 56) | (SEQ ID NO: 11) | | |
| TETO-1219 F (SEQ ID NO: 57) | T11 | 639 | PHP51072 |
| TETO-1220 R (SEQ ID NO: 58) | (SEQ ID NO: 12) | | |
| TETO-1036 F (SEQ ID NO: 59) | T12 | 685 | PHP49626 |
| TETO-1037 R (SEQ ID NO: 60) | (SEQ ID NO: 13) | | |
| TETO-1038 F (SEQ ID NO: 61) | T13 | 411 | PHP49627 |
| TETO-1039 R (SEQ ID NO: 62) | (SEQ ID NO: 14) | | |
| TETO-1040 F (SEQ ID NO: 63) | T14 | 457 | PHP49628 |
| TETO-1041 R (SEQ ID NO: 64) | (SEQ ID NO: 15) | | |
| TETO-986 F (SEQ ID NO: 65) | T15 | 782 | PHP51073 |
| TETO-987 R (SEQ ID NO: 66) | (SEQ ID NO: 16) | | |
| TETO-988 F (SEQ ID NO: 67) | T16 | 825 | PHP51074 |
| TETO-989 R (SEQ ID NO: 68) | (SEQ ID NO: 17) | | |
| TETO-990 F (SEQ ID NO: 69) | T17 | 776 | PHP51075 |
| TETO-991 R (SEQ ID NO: 70) | (SEQ ID NO: 18) | | |
| TETO-992 F (SEQ ID NO: 71) | T18 | 881 | PHP51076 |
| TETO-993 R (SEQ ID NO: 72) | (SEQ ID NO: 19) | | |
| TETO-994 F (SEQ ID NO: 73) | T19 | 772 | PHP51077 |
| TETO-995 R (SEQ ID NO: 74) | (SEQ ID NO: 20) | | |
| TETO-996 F (SEQ ID NO: 75) | T20 | 827 | PHP51078 |
| TETO-997 R (SEQ ID NO: 76) | (SEQ ID NO: 21) | | |
| TETO-998 F (SEQ ID NO: 77) | T21 | 770 | PHP51079 |
| TETO-999 R (SEQ ID NO: 78) | (SEQ ID NO: 22) | | |
| TETO-1000 F (SEQ ID NO: 79) | T22 | 814 | PHP51080 |
| TETO-1001 R (SEQ ID NO: 80) | (SEQ ID NO: 23) | | |
| TETO-1002 F (SEQ ID NO: 81) | T23 | 834 | PHP51081 |
| TETO-1003 R (SEQ ID NO: 82) | (SEQ ID NO: 24) | | |
| TETO-1004 F (SEQ ID NO: 83) | T24 | 740 | PHP51082 |
| TETO-1005 R (SEQ ID NO: 84) | (SEQ ID NO: 25) | | |
| TETO-1006 F (SEQ ID NO: 85) | T25 | 782 | PHP51083 |
| TETO-1007 R (SEQ ID NO: 86) | (SEQ ID NO: 26) | | |
| TETO-1008 F (SEQ ID NO: 87) | T26 | 825 | PHP51084 |
| TETO-1009 R (SEQ ID NO: 88) | (SEQ ID NO: 27) | | |
| TETO-1010 F (SEQ ID NO: 89) | T27 | 776 | PHP51085 |
| TETO-1011 R (SEQ ID NO: 90) | (SEQ ID NO: 28) | | |
| TETO-1012 F (SEQ ID NO: 91) | T28 | 881 | PHP51086 |
| TETO-1013 R (SEQ ID NO: 92) | (SEQ ID NO: 29) | | |
| TETO-1014 F (SEQ ID NO: 93) | T29 | 772 | |
| TETO-1015 R (SEQ ID NO: 94) | (SEQ ID NO: 30) | | |
| TETO-1016 F (SEQ ID NO: 95) | T30 | 827 | PHP51088 |
| TETO-1017 R (SEQ ID NO: 96) | (SEQ ID NO: 31) | | |
| TETO-1018 F (SEQ ID NO: 97) | T31 | 770 | PHP51089 |
| TETO-1019 R (SEQ ID NO: 98) | (SEQ ID NO: 32) | | |
| TETO-1020 F (SEQ ID NO: 99) | T32 | 814 | |
| TETO-1021 R (SEQ ID NO: 100) | (SEQ ID NO: 33) | | |
| TETO-1022 F (SEQ ID NO: 101) | T33 | 834 | |
| TETO-1023 R (SEQ ID NO: 102) | (SEQ ID NO: 34) | | |
| TETO-1024 F (SEQ ID NO: 103) | T34 | 740 | PHP51092 |
| TETO-1025 R (SEQ ID NO: 104) | (SEQ ID NO: 35) | | |
| TETO-420 F (SEQ ID NO: 105) | Pin II | 330 | PHP49598 |
| TETO-421 R (SEQ ID NO: 106) | (SEQ ID NO: 36) | | |

TABLE 3

Terminator Sequences in Inverse Orientations

| Orientation 1 | Orientation 2 | Species |
|---|---|---|
| T1 (SEQ ID NO: 2) | T8 (SEQ ID NO: 9) | Arabidopsis thaliana |
| T2 (SEQ ID NO: 3) | T9 (SEQ ID NO: 10) | Arabidopsis thaliana |
| T3 (SEQ ID NO: 4) | T10 (SEQ ID NO: 11) | Arabidopsis thaliana |
| T4 (SEQ ID NO: 5) | T11 (SEQ ID NO: 12) | Arabidopsis thaliana |
| T5 (SEQ ID NO: 6) | T12 (SEQ ID NO: 13) | Arabidopsis thaliana |
| T6 (SEQ ID NO: 7) | T13 (SEQ ID NO: 14) | Arabidopsis thaliana |
| T7 (SEQ ID NO: 8) | T14 (SEQ ID NO: 15) | Arabidopsis thaliana |
| T15 (SEQ ID NO: 16) | T25 (SEQ ID NO: 26) | Oryza sativa |
| T16 (SEQ ID NO: 17) | T26 (SEQ ID NO: 27) | Oryza sativa |
| T17 (SEQ ID NO: 18) | T27 (SEQ ID NO: 28) | Oryza sativa |
| T18 (SEQ ID NO: 19) | T28 (SEQ ID NO: 29) | Oryza sativa |
| T19 (SEQ ID NO: 20) | T29 (SEQ ID NO: 30) | Oryza sativa |
| T20 (SEQ ID NO: 21) | T30 (SEQ ID NO: 31) | Oryza sativa |
| T21 (SEQ ID NO: 22) | T31 (SEQ ID NO: 32) | Oryza sativa |
| T22 (SEQ ID NO: 23) | T32 (SEQ ID NO: 33) | Oryza sativa |
| T23 (SEQ ID NO: 24) | T33 (SEQ ID NO: 34) | Oryza sativa |
| T24 (SEQ ID NO: 25) | T34 (SEQ ID NO: 35) | Oryza sativa |

Example 3

Rice Transformation with Candidate Terminator Sequences

The candidate terminator sequences T1-T34 (SEQ ID NOS:2-35) can be transformed into rice plants by Agrobacterium-mediated transformation by using Agrobacterium containing the constructs described in Table 2.

Transformation and Regeneration of Rice Callus Via Agrobacterium Infection:

O. sativa spp. japonica rice var. Nipponbare seeds are sterilized in absolute ethanol for 10 minutes then washed 3 times with water and incubated in 70% Sodium hypochlorite [Fisher Scientific-27908] for 30 minutes. The seeds are then washed 5 times with water and dried completely. The dried seeds are inoculated into NB-CL media [CHU(N6) basal salts (PhytoTechnology-C416) 4 g/l; Eriksson's vitamin solution (1000× PhytoTechnology-E330) 1 ml/l; Thiamine HCl (Sigma-T4625) 0.5 mg/l; 2,4-Dichloro phenoxyacetic acid (Sigma-D7299) 2.5 mg/l; BAP (Sigma-B3408) 0.1 mg/l; L-Proline (PhytoTechnology-P698) 2.5 g/l; Casein acid hydrolysate vitamin free (Sigma-C7970) 0.3 g/l; Myo-inositol (Sigma-I3011) 0.1 g/l; Sucrose (Sigma-S5390) 30 g/l; GELRITE® (Sigma-G1101.5000) 3 g/l; pH 5.8) and kept at 28° C. in dark for callus proliferation.

A single Agrobacterium colony containing a desired insert with the candidate terminator sequences (SEQ ID NOS:2-35) or PINII terminator (SEQ ID NO:36) from a freshly streaked plate can be inoculated in YEB liquid media [Yeast extract (BD Difco-212750) 1 g/l; Peptone (BD Difco-211677) 5 g/l; Beef extract (Amresco-0114) 5 g/l; Sucrose (Sigma-55390) 5 g/l; Magnesium Sulfate (Sigma-M8150) 0.3 g/l at pH-7.0] supplemented with Tetracycline (Sigma-T3383) 5 mg/l, Rifamysin 10 mg/l and Spectinomycin (Sigma-5650) 50 mg/l. The cultures are grown overnight at 28° C. in dark with continuous shaking at 220 rpm. The following day the cultures are adjusted to 0.5 Absorbance at 550 nm in PHI-A(CHU(N6) basal salts (PhytoTechnology-C416) 4 g/l; Eriksson's vitamin solution (1000× PhytoTechnology-E330) 1 ml/l; Thiamine HCl (Sigma-T4625) 0.5 mg/l; 2,4-Dichloro phenoxyacetic acid (Sigma-D7299) 2.5 mg/l, L-Proline (PhytoTechnology-P698) 0.69 mg/l; Sucrose (Sigma-S5390) 68.5 g/l; Glucose-36 g/l (Sigma-G8270); pH 5.8);) media supplemented with 200 µM Acetosyringone (Sigma-D134406) and incubated for 1 hour at 28° C. with continuous shaking at 220 rpm.

17-21 day old proliferating calli are transferred to a sterile culture flask and Agrobacterium solution prepared as described above was added to the flask. The suspension is incubated for 20 minutes with gentle shaking every 2 minutes. The Agrobacterium suspension is decanted carefully and the calli are placed on WHATMAN® filter paper No-4. The calli are immediately transferred to NB-CC medium [NB-CL supplemented with 200 µM Acetosyringone (Sigma-D134406) and incubated at 21° C. for 72 hrs.

Culture Termination and Selection:

The co-cultivated calli are placed in a dry, sterile, culture flask and washed with 1 liter of sterile distilled water containing Cefotaxime (Duchefa-00111.0025) 0.250 g/l and Carbenicillin (Sigma-00109.0025) 0.4 g/l. The washes are repeated 4 times or until the solution appeared clear. The water is decanted carefully and the calli are placed on WHATMAN® filter paper No-4 and dried for 30 minutes at room temperature. The dried calli are transferred to NB-RS medium [NB-CL supplemented with Cefotaxime (Duchefa-00111.0025) 0.25 g/l; and Carbenicillin (Sigma-00109.0025) 0.4 g/l and incubated at 28° C. for 4 days.

The calli are then transferred to NB-SB media [NB-RS supplemented with Bialaphos (Meiji Seika K. K., Tokyo, Japan) 5 mg/l and incubated at 28° C. and subcultured into fresh medium every 14 days. After 40-45 days on selection, proliferating, Bialaphos-resistant callus events are easily observable.

Regeneration of Stably Transformed Rice Plants from Transformed Rice Calli:

Transformed callus events are transferred to NB-RG media [CHU(N6) basal salts (PhytoTechnology-C416) 4 g/l; N6 vitamins 1000×1 ml {Glycine (Sigma-47126) 2 g/l; Thiamine HCl (Sigma-T4625) 1 g/l; acid; Kinetin (Sigma-K0753) 0.5 mg/l; Casein acid hydrolysate vitamin free (Sigma-C7970) 0.5 g/l; Sucrose (Sigma-S5390) 20 g/l; Sorbitol (Sigma-S1876) 30 g/l, pH was adjusted to 5.8 and 4 g/l GELRITE® (Sigma-G1101.5000) was added. Post-sterilization 0.1 ml/l of CuSo4 (100 mM concentration, Sigma-C8027) and 100 ml/l 10× AA Amino acids pH free {Glycine (Sigma-G7126) 75 mg/l; L-Aspartic acid (Sigma-A9256) 2.66 g/l; L-Arginine (Sigma-A5006) 1.74 g/l; L-Glutamine (Sigma-G3126) 8.76 g/l} and incubated at 32° C. in light. After 15-20 days, regenerating plantlets can be transferred to magenta boxes or tubes containing NB-RT media [MS basal salts (PhytoTechnology-M524) 4.33 g/L; B5 vitamins 1 ml/l from 1000× stock {Nicotinic acid (Sigma-G7126) 1 g/l, Thiamine HCl (Sigma-T4625) 10 g/l)}; Myo-inositol (Sigma-I3011) 0.1 g/l; Sucrose (Sigma-55390) 30 g/l; and IBA (Sigma-I5386) 0.2 mg/l; pH adjusted to 5.8]. Rooted plants obtained after 10-15 days can be hardened in liquid Y media [1.25 ml each of stocks A-F and water sufficient to make 1000 ml. Composition of individual stock solutions: Stock (A) Ammonium Nitrate (HIMEDIA-RM5657) 9.14 g/l, (B) Sodium hydrogen Phosphate (HIMEDIA-58282) 4.03 g, (C) Potassium Sulphate (HIMEDIA-29658-4B) 7.14 g, (D) Calcium Chloride (HIMEDIA-05080) 8.86 g, (E) Magnesium Sulphate (HIMEDIA-RM683) 3.24 g, (F) (Trace elements) Magnesium chloride tetra hydrate (HIMEDIA-10149) 15 mg, Ammonium Molybdate (HIMEDIA-271974B) 6.74 mg/l, Boric acid (Sigma-136768) 9.34 g/l, Zinc sulphate heptahydrate (HiMedia-RM695) 0.35 mg/l, Copper Sulphate heptahydrate (HIMEDIA-C8027) 0.31 mg/l, Ferric chloride hexahydrate (Sigma-236489) 0.77 mg/l, Citric acid monohydrate (HIMEDIA-C4540) 0.119 g/l] at 28° C. for 10-15 days before transferring to greenhouse. Leaf samples are collected for histochemical GUS staining with 5-bromo-4-chloro-3-indolyl-β-D-glucuronide (X-Gluc), using standard protocols (Janssen and Gardner, *Plant Mal. Biol.* (1989)14:61-72).

Transgenic plants are analyzed for copy number by southern blotting using standard procedure. All single copy events are transferred to individual pots and further analysis is performed only on these. For all the analysis leaf material from three independent one month old single copy $T_0$ events are taken.

Example 4

Rice Transformation with Candidate Rice Terminator Sequences

The candidate rice terminator sequences (SEQ ID NOS: 16-35) were tested for their efficacy to function as transcription terminators by transformation into rice plants by *Agrobacterium*-mediated transformation as described in Example 3. The constructs for generating the transgenic plants are described in Table 2.

Example 5A

Assays for Testing of Candidate Rice Terminator Sequences in Stably Transformed Rice Tissues ReverseTranscriptase-PCR (RT-PCR) as well as quantitative RT-PCR (qRT-PCR) can be done from stably transformed rice plant tissues, to test the ability of candidate terminator sequences to stop transcription (i.e., prevent read-through transcription). QRT-PCR is the preferred way of testing the candidate terminator sequences. SEQ ID NOS:100-113 can be used for doing RT-PCR to determine read-through transcription from the candidate terminator sequences.

Histochemical and Fluorometric GUS Analysis:

Leaf samples from each construct can be used for histochemical GUS staining with 5-bromo-4-chloro-3-indolyl-β-D-glucuronide (X-Gluc), using standard protocols (Janssen and Gardner, *Plant Mol. Biol.* (1989)14:61-72) and three pools of leaf samples from three independent single copy events per construct may be used for quantitative MUG assay using standard protocols (Jefferson, R. A., Nature. 342, 837-8 (1989); Jefferson, R. A., Kavanagh, T. A. & Bevan, M. W. EMBO J. 6, 3901-3907 (1987).

Example 5B

Figure 2:
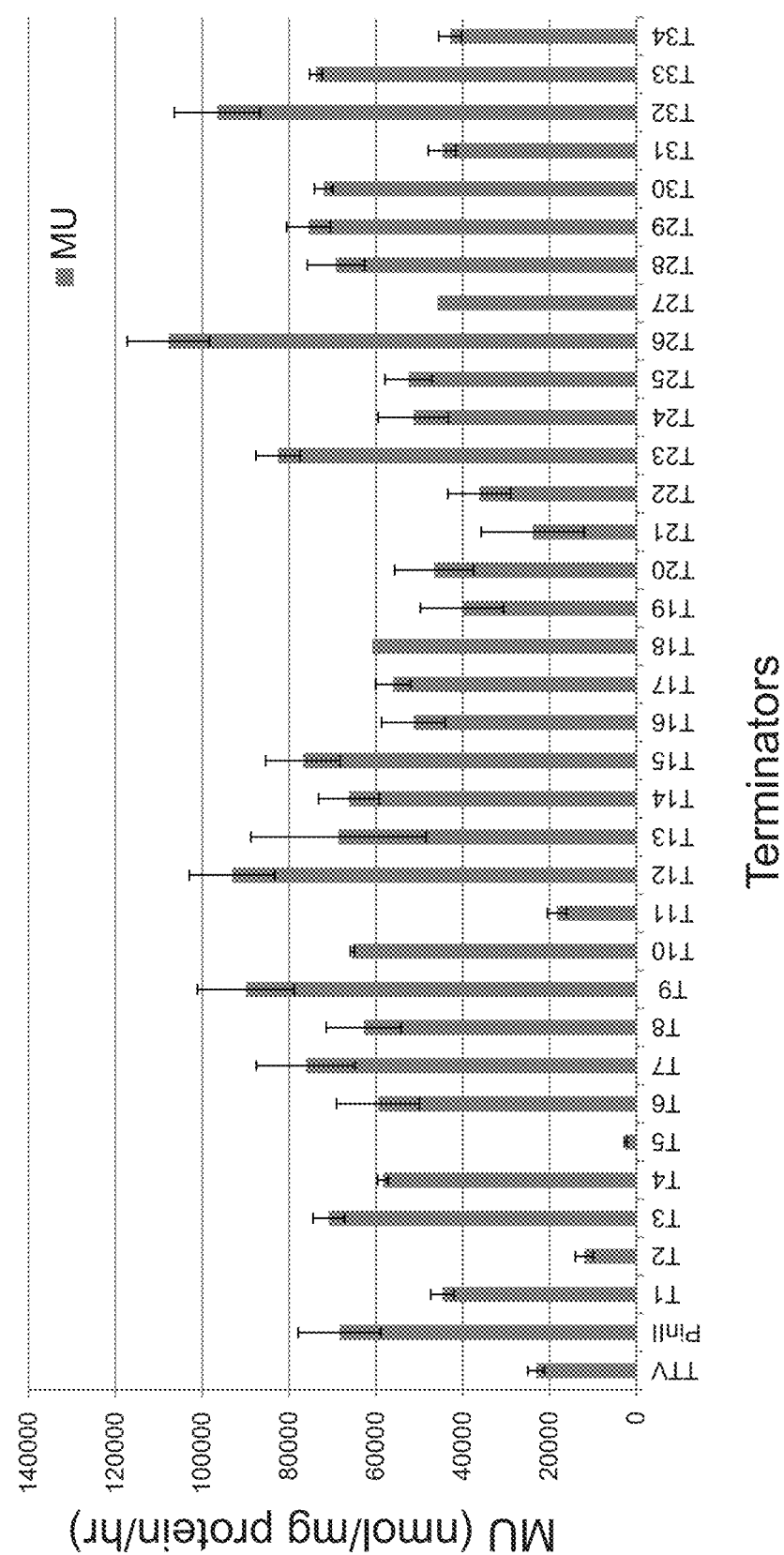
FIG. 2 depicts the GUS quantitative assay of leaf samples of single-copy stable rice events harboring the constructs.

Testing of Candidate Rice Terminator Sequences in Stably Transformed Rice Tissues GUS Fluorometric Analysis of Rice Tissues Stably Transformed with Candidate Rice Terminator Sequences:

When compared with TTV, we observed higher GUS protein expression with PIN II as well as test sequences T15, T16, T17, T18, T19, T20, T22, T23, T24, T25, T26, T27, T28, T29, T30, T31, T32, T33 and T34 (SEQ ID NOS:16-21, 23-35 respectively). However, T21 (SEQ ID NO:22) had the same level of GUS expression as TTV (FIG. 2).

Quantitative Reverse Transcriptase PCR (qRT-PCR) to Determine Read Through Transcription Through Test Terminator:

qRT-PCR was performed with leaf tissue from stable transformants. The stably transformed plants were tested for the presence of read-through transcript that had passed through the PINII terminator and the test terminators. To assess presence of products that would indicate that transcription was continuing past the terminator, amplification was targeted downstream of the terminator being tested. A primer set was designed downstream of the PINII or test terminators, in the filler sequence (Ds Red). The read-through can be measured by the ratio of DsRed to GUS.

At least three pools of leaf samples from three independent single copy events were tested for each construct. The primers and probes are listed in Table 4.

TABLE 4

| Probe (SEQ ID NO) | Primer Sequence (SEQ ID NO) | Fluor | qPCR Assay Type |
|---|---|---|---|
| GUS (SEQ ID NO: 114) | GUSFwd primer (SEQ ID NO: 115) GUS Rev primer (SEQ ID NO: 116) | FAM | TAQMAN® |
| DsRed (SEQ ID NO: 117) | DsRed Fwd primer (SEQ ID NO: 118) DsRed Rev primer (SEQ ID NO: 119) | FAM | TAQMAN® |

Figure 3:
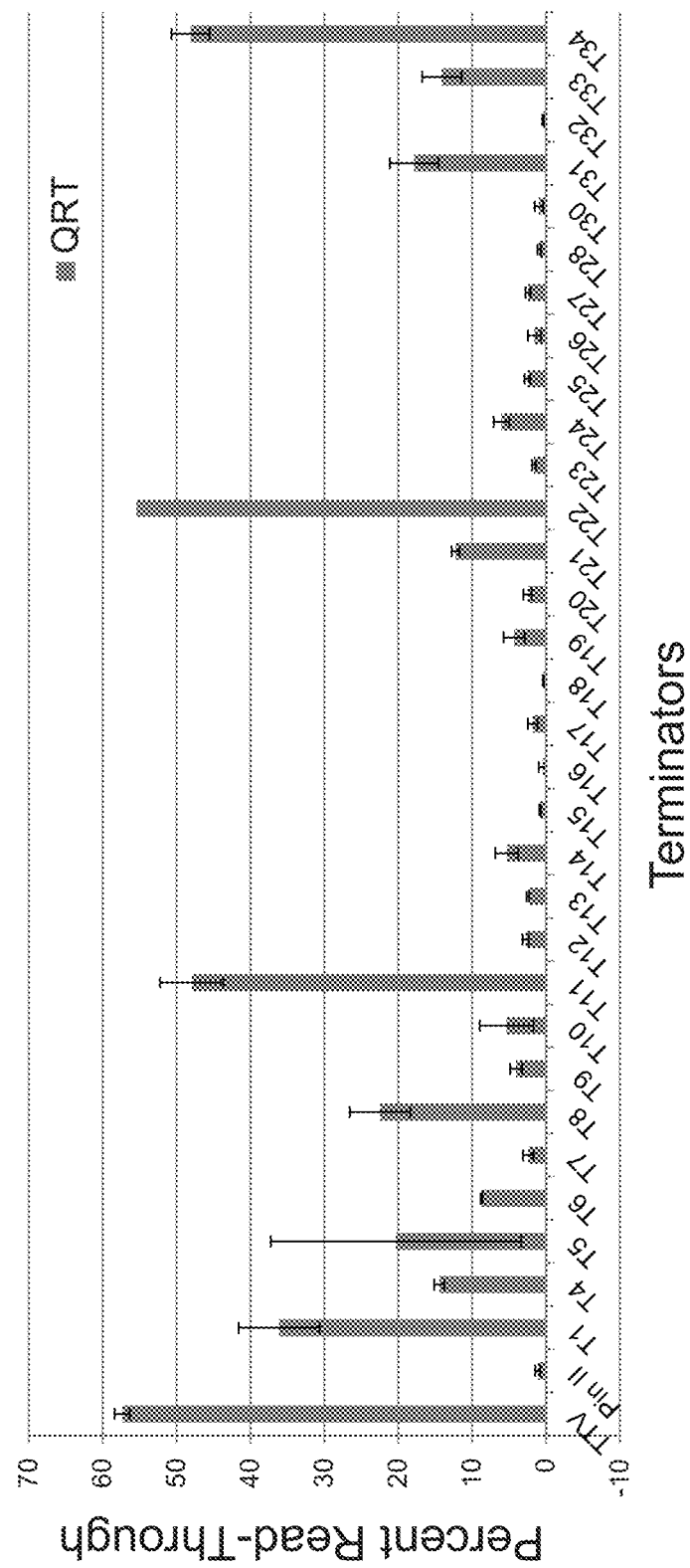
FIG. 3 shows the qRT-PCR data of single-copy stable rice events harboring TTV constructs containing the candidate terminator sequences: No terminator control (TTV), PINII terminator, T1 (SEQ ID NO:2), T4-T28 (SEQ ID NOS:5-29), T30-T34 (SEQ ID NOS:31-35).

Read-Through Transcription from Candidate Rice Sequences:

As expected, read-through transcription was observed in the terminator test vector (TTV (SEQ ID NO:1; PHP49597) as depicted in FIG. 3. The PHP49598 construct with the PINII terminator (SEQ ID NO:36) reduced the transcription read-through significantly (FIG. 3). Candidate terminator sequences from *Oryza sativa* T15, T16, T17, T18, T20, T23, T25, T26, T27, T28, T30 and T32 (SEQ ID NOS:16-19, 21, 24, 26-29, 31 and 33 respectively) were able to terminate transcription efficiently as evidenced by the very low level of read-through transcripts (FIG. 3), comparable to the PINII terminator. As can be seen from Table 3, T14 and T25 (SEQ ID NOS:15 and 26 respectively); T16 and T26 (SEQ ID NOS:17 and 27 respectively); T17 and T27 (SEQ ID NOS: 18 and 28 respectively); T18 and T28 (SEQ ID NOS:19 and 29 respectively); T20 and T30 (SEQ ID NOS:21 and 31 respectively) are the same nucleotide sequence but cloned in inverted orientation. Hence these can function as bi-directional terminator sequences. Candidate terminator sequences T19, T21 and T24 (SEQ ID NOS:20, 22 and 25 respectively) also showed less read through compared to the TTV terminator (FIG. 3)

Example 6

Rice Transformation with Candidate *Arabidopsis* Terminator Sequences

The candidate *Arabidopsis* terminator sequences (SEQ ID NOS:2-15) can be transformed into rice plants by *Agrobacterium*-mediated transformation as described in Example 3, to test their efficacy to function as transcription terminators. The constructs are described in Table 2.

Example 7

Testing of Candidate *Arabidopsis* Terminator Sequences in Stably Transformed Rice Tissues QRT-PCR was done from stably transformed rice plant tissues, to test the ability of candidate *Arabidopsis* terminator sequences (SEQ ID NOS:2-15) to stop transcription (that is prevent transcription read-through transcription) and to compare GUS expression as compared to that with PINII terminator, as described in Example 5.

23

Read-Through Transcription from Candidate *Arabidopsis* Sequences:

Terminator sequences from *Arabidopsis thaliana* T7, T9, T10, T12, T13, (SEQ ID NOS:8, 10, 11, 13 and 14 respectively) were able to terminate transcription efficiently as evidenced by the very low level of read-through transcripts (FIG. 3), comparable to the PINII terminator. Terminator sequences T4, T5 and T6 also showed less read through compared to the TTV terminator (FIG. 3).

GUS Fluorometric Analysis of Rice Tissues Stably Transformed with Candidate *Arabidopsis* Terminator Sequences When compared with TTV, we observed higher GUS protein expression with PINII as well as test sequences T1, T3, T4, T6, T7, T8, T9, T10, T12, T13, and T14 (SEQ ID NOS:2, 4, 5, 7, 8, 10, 13, 14 and 15 respectively). However, T2, T5 and T11 (SEQ ID NOS:3, 6 and 12) had the same level of GUS expression as TTV (FIG. 2).

Example 8

Identification of Shorter Terminator Sequences

Each candidate bidirectional transcriptional terminator might be comprised of two convergent constituent transcriptional terminators. To identify these constituent terminator sequences, polyadenylation sites were mapped as described below.

Mapping Polyadenylation Sites in Terminator Sequences

RNA was extracted from leaf tissue of $T_0$ single copy event for each construct. cDNA was synthesized using SuperScript® III First-Strand Synthesis System from INVITROGEN™ using adapter ligated oligodT primer (TETO-1527; SEQ ID NO:126) and PCR was performed with GUS internal primer (TET0-1172; SEQ ID NO:127) and adapter reverse primers (TETO-1528; SEQ ID NO:128). The amplified products were cloned using Zero Blunt® TOPO® PCR cloning kit (INVITROGEN™). For each terminator, 40 clones were sequenced. The sequence analysis revealed multiple polyA sites. The sequences of the shorter terminator sequences corresponding to the longer terminator sequences are given in SEQ ID NOS:129-162 and in Table 6.

TABLE 5

| Primer Name | SEQ ID NO | Primer ID |
|---|---|---|
| TETO-1527 | 126 | Adap-dT |
| TETO-1172 | 127 | GUS iF |
| TETO-1528 | 128 | Adap R |

24

TABLE 6

| Orientation 1 | Orientation 2 | Species | 5' terminator | 3' terminator |
|---|---|---|---|---|
| T1 (SEQ ID NO: 2) | T8 (SEQ ID NO: 9) | Arabidopsis thaliana | T1s (SEQ ID NO: 129) | T8s (SEQ ID NO: 136) |
| T2 (SEQ ID NO: 3) | T9 (SEQ ID NO: 10) | Arabidopsis thaliana | T2s (SEQ ID NO: 130) | T9s (SEQ ID NO: 137) |
| T3 (SEQ ID NO: 4) | T10 (SEQ ID NO: 11) | Arabidopsis thaliana | T3s (SEQ ID NO: 131) | T10s (SEQ ID NO: 138) |
| T4 (SEQ ID NO: 5) | T11 (SEQ ID NO: 12) | Arabidopsis thaliana | T4s (SEQ ID NO: 132) | T11s (SEQ ID NO: 139) |
| T5 (SEQ ID NO: 6) | T12 (SEQ ID NO: 13) | Arabidopsis thaliana | T5s (SEQ ID NO: 133) | T12s (SEQ ID NO: 140) |
| T6 (SEQ ID NO: 7) | T13 (SEQ ID NO: 14) | Arabidopsis thaliana | T6s (SEQ ID NO: 134) | T13s (SEQ ID NO: 141) |
| T7 (SEQ ID NO: 8) | T14 (SEQ ID NO: 15) | Arabidopsis thaliana | T7s (SEQ ID NO: 135) | T14s (SEQ ID NO: 142) |
| T15 (SEQ ID NO: 16) | T25 (SEQ ID NO: 26) | Oryza sativa | T15s (SEQ ID NO: 143) | T25s (SEQ ID NO: 153) |
| T16 (SEQ ID NO: 17) | T26 (SEQ ID NO: 27) | Oryza sativa | T16s (SEQ ID NO: 144) | T26s (SEQ ID NO: 154) |
| T17 (SEQ ID NO: 18) | T27 (SEQ ID NO: 28) | Oryza sativa | T17s (SEQ ID NO: 145) | T27s (SEQ ID NO: 155) |
| T18 (SEQ ID NO: 19) | T28 (SEQ ID NO: 29) | Oryza sativa | T18s (SEQ ID NO: 146) | T28s (SEQ ID NO: 156) |
| T19 (SEQ ID NO: 20) | T29 (SEQ ID NO: 30) | Oryza sativa | T19s (SEQ ID NO: 147) | T29 (SEQ ID NO: 157) |
| T20 (SEQ ID NO: 21) | T30 (SEQ ID NO: 31) | Oryza sativa | T20s (SEQ ID NO: 148) | T30 (SEQ ID NO: 158) |
| T21 (SEQ ID NO: 22) | T31 (SEQ ID NO: 32) | Oryza sativa | T21s (SEQ ID NO: 149) | T31s (SEQ ID NO: 159) |
| T22 (SEQ ID NO: 23) | T32 (SEQ ID NO: 33) | Oryza sativa | T22s (SEQ ID NO: 150) | T32s (SEQ ID NO: 160) |
| T23 (SEQ ID NO: 24) | T33 (SEQ ID NO: 34) | Oryza sativa | T23s (SEQ ID NO: 151) | T33s (SEQ ID NO: 161) |
| T24 (SEQ ID NO: 25) | T34 (SEQ ID NO: 35) | Oryza sativa | T24s (SEQ ID NO: 152) | T34s (SEQ ID NO: 162) |

Example 9

Testing of Truncated Terminator Sequences in Stably Transformed *Arabidopsis* Tissue Based on the polyA data obtained as described in Example 8, the terminators can be truncated and cloned as described in the Example 2.

The truncated terminators (SEQ ID NOS:129-162) can be transformed into *Arabidopsis thaliana* by floral dip method (Kim J Y et al (2003) Development 130: 4351-4362). QRT-PCR and MUG analysis can be done to test the efficiency of the truncated terminators in T1 *Arabidopsis* leaf tissue as described in Example 5.

We claim:

1. A recombinant construct comprising a polynucleotide comprising:
   (a) a nucleotide sequence as set forth in SEQ ID NO: 18 or 28; or
   (b) a functional fragment of at least 200 contiguous nucleotides of SEQ ID NO: 18 or 28 having terminator activity;
   wherein the polynucleotide functions as a bidirectional transcriptional terminator in a plant cell, wherein the polynucleotide is operably linked to:
   (b) the 3' end of a first heterologous polynucleotide which is operably linked to a first promoter; and
   (c) the 3' end of a second heterologous polynucleotide which is operably linked to a second promoter;
   wherein the first and the second heterologous polynucleotides are transcribed in a convergent manner.

2. A plant comprising in its genome the recombinant construct of claim 1.

3. A seed from the plant of claim 2, wherein the seed comprises said recombinant construct.

4. The plant of claim 2, wherein said plant is selected from the group consisting of: *Arabidopsis*, maize, soybean, sunflower, sorghum, canola, mustard, wheat, alfalfa, cotton, rice, barley, millet, sugar cane and switchgrass.

5. The seed of claim 3, wherein said seed is selected from the group consisting of: *Arabidopsis*, maize, soybean, sunflower, sorghum, canola, mustard, wheat, alfalfa, cotton, rice, barley, millet, sugar cane and switchgrass.

6. A method of regulating the expression of two heterologous polynucleotides in a plant, comprising the steps of:
   (a) introducing into a regenerable plant cell the recombinant construct of claim 1;
   (b) regenerating a transgenic plant from the regenerable plant cell of (a), wherein the transgenic plant comprises in its genome the recombinant construct of claim 1; and
   (c) obtaining a progeny plant from the transgenic plant of step (b), wherein the progeny plant comprises in its genome the recombinant construct of claim 1 and exhibits expression of both the first heterologous polynucleotide and the second heterologous polynucleotide.

7. The method of claim 6, wherein said plant is selected from the group consisting of: *Arabidopsis*, maize, soybean, sunflower, sorghum, canola, mustard, wheat, alfalfa, cotton, rice, barley, millet, sugar cane and switchgrass.

* * * * *